(12) United States Patent
Hibberd et al.

(10) Patent No.: US 9,260,720 B2
(45) Date of Patent: Feb. 16, 2016

(54) TRANSGENIC PLANTS COMPRISING CONSTRUCTS ENCODING PHOSPHOENOLPYRUVATE CARBOXYKINASE AND/OR PYRUVATE ORTHOPHOSPHATE DIKINASE

(75) Inventors: Julian Michael Hibberd, Cambridge (GB); Lucy Elisabeth Taylor, Cambridge (GB); Anna Elizabeth Leiss, Cambridge (GB)

(73) Assignee: BRITISH AMERICAN TOBACCO (INVESTMENTS) LIMITED, London (GB)

( * ) Notice: Subject to any disclaimer, the term of this patent is extended or adjusted under 35 U.S.C. 154(b) by 953 days.

(21) Appl. No.: 13/203,686

(22) PCT Filed: Feb. 25, 2010

(86) PCT No.: PCT/GB2010/050321
§ 371 (c)(1),
(2), (4) Date: Feb. 8, 2012

(87) PCT Pub. No.: WO2010/097623
PCT Pub. Date: Sep. 2, 2010

(65) Prior Publication Data
US 2012/0125355 A1 May 24, 2012

(30) Foreign Application Priority Data

Feb. 27, 2009 (GB) .................................. 0903346.5

(51) Int. Cl.
| | |
|---|---|
| A01H 5/00 | (2006.01) |
| A01H 5/12 | (2006.01) |
| A01H 1/00 | (2006.01) |
| C12N 15/82 | (2006.01) |
| A24B 15/10 | (2006.01) |
| A24B 15/24 | (2006.01) |
| C07H 21/04 | (2006.01) |
| C07K 14/415 | (2006.01) |
| C12N 15/00 | (2006.01) |
| C12N 15/63 | (2006.01) |

(52) U.S. Cl.
CPC .............. *C12N 15/8266* (2013.01); *A01H 5/12* (2013.01); *A24B 15/10* (2013.01); *A24B 15/245* (2013.01)

(58) Field of Classification Search
None
See application file for complete search history.

(56) References Cited

U.S. PATENT DOCUMENTS

| | | | |
|---|---|---|---|
| 5,689,042 A | 11/1997 | Amasino et al. | |
| 5,912,156 A * | 6/1999 | Ohta et al. | ........... 435/194 |
| 6,610,913 B1 * | 8/2003 | Arai et al. | ........... 800/320.2 |
| 7,396,977 B2 * | 7/2008 | Usami et al. | ........... 800/278 |
| 2003/0150009 A1 * | 8/2003 | Gallie et al. | ........... 800/278 |
| 2003/0221219 A1 | 11/2003 | Arai et al. | |

FOREIGN PATENT DOCUMENTS

| | | |
|---|---|---|
| EP | 0116718 A1 | 8/1984 |
| EP | 0242246 A1 | 10/1987 |
| EP | 0270822 A1 | 6/1988 |
| EP | 0369637 A2 | 5/1990 |
| EP | 0874056 A1 | 10/1998 |
| EP | 0916725 A1 | 5/1999 |
| EP | 1586645 * | 10/2005 |
| GB | 2197653 A | 5/1988 |
| RU | 2159813 C2 | 11/2000 |
| RU | 2312144 C2 | 12/2007 |
| WO | 98/35030 A1 | 8/1998 |
| WO | 03018766 A1 | 3/2003 |
| WO | 2008122767 A2 | 10/2008 |

OTHER PUBLICATIONS

Alexandrov et al., Geneseq Database, Acc. No. ALJ69489, EP1586645, Oct. 19, 2005, Seq ID No. 36742.*
Noh, Yoo-Sun et al., "Identification of a promoter region responsible for the senesence-specfic expression of SAG12," Plant Molecular Biology, 1999, vol. 41, pp. 181-194.
Office Action issued Jun. 10, 2014 in corresponding Japanese Patent Application No. 2011-551528 [citing Plant Molecular Biology, 1999, vol. 41, pp. 181-194, and WO 98/35030] [with machine translation into English].
Trejo-Tellez, L.I., "Metabolische Rolle des Enzyms Pyruvat, Phosphat Dikinase in transgenen Tabakpflanzen", Dissertation zur Erlangung des akademischen Grades des Doktors der Naturwissenschaften, Nov. 2004, pp. 1-143, XP007912978, Retrieved from the Internet: URL: http://www.diss.fu-berlin.de/diss/servlets/MCRFileNodeServlet/FUDISS_derivate_000000001382/?hosts=> (retrieved on May 6, 2010) pp. 1, 2, 4-11, 13-15, 49, 52, 55, 69, 71, 81, 83-86, 102-112, 116, 117, 122-125.
Sheriff, A. et al., "The influence of plant pyruvate, orthophosphate dikinase on a $C_3$ plant with respect to the intracellular location of the enzyme", *Plant Science*, vol. 136, No. 1, Aug. 7, 1998, pp. 43-57, XP007912979.

(Continued)

*Primary Examiner* — Phuong Bui
(74) *Attorney, Agent, or Firm* — McKee, Voorhees & Sease, PLC

(57) ABSTRACT

The invention provides genetic constructs which comprise a senescence-specific promoter operably linked to at least one coding sequence, which encodes at least one polypeptide having phosphoenolpyruvate carboxykinase (PCK) activity and/or pyruvate orthophosphate dikinase (PPDK) activity. The constructs have the ability to cause, in transgenic plants, remobilisation of nitrogen during leaf senescence, such that nitrogen can be transported from the leaves to other regions of the plants. The invention provides plant cells and plants transformed with such constructs, methods of producing transgenic plants, and methods of increasing the rate of nitrogen remobilisation and growth rate in senescent plants. The invention also provides harvested plant leaves, such as tobacco leaves, that have been transformed with the genetic constructs, and to smoking articles comprising such harvested plant leaves.

13 Claims, 11 Drawing Sheets

(56) References Cited

OTHER PUBLICATIONS

Chen, Zhi-Hui et al., "Are Isocitrate Lyase and Phosphoenolpyruvate Carboxykinase Involved in Gluconeogenesis during Senescence of Barley Leaves and Cucumber Cotyledons?", *Plant and Cell Physiology*, vol. 41, No. 8, Aug. 2000, pp. 960-967.

Lin, Ji-Feng et al., "Molecular events in senescing Arabidopsis leaves", *The Plant Journal*, vol. 39, No. 4, Aug. 1, 2004, pp. 612-628, XP002541477.

Gepstein, S. et al., "Large-scale identification of leaf senescence-associated genes", *The Plant Journal*, vol. 36, No. 5, Dec. 1, 2003, pp. 629-642, XP002553434.

Taylor, L. et al., "Cytosolic pyruvate, orthophosphate dikinase functions in nitrogen remobilization during leaf senescence and limits individual seed growth and nitrogen content," The Plant Journal, Feb. 24, 2010, XP007912980; Retrieved from the Internet: URL: http://www3.interscience.wiley.com/jouurnal/123301890/abstract?CRETRY=1&SRETRY=o> (retrieved on May 6, 2010).

International Search Report and Written Opinion, mailed May 26, 2010, for PCT International Application No. PCT/GB2010/050321, filed Feb. 25, 2010.

International Preliminary Report on Patentability, mailed Apr. 1, 2011, for PCT International Application No. PCT/GB2010/050321, filed Feb. 25, 2010.

Genbank accession No. U37336.1, Gan S., et al., Dec. 30, 1995.
Genbank accession No. AK221969.1, Totoki Y., et al., Sep. 17, 2005.
Genbank accession No. AK230049.1, Totoki Y., et al., Jul. 27, 2006.
EC 2.7.9.1 Pyruvate. 1972. IUBMB Nomenclature.
EC 4.1.1.49 PEPCK or PCK. 1972. IUBMB Nomenclature.
Bubner B & Baldwin. Use of real-time PCR for determining copy number and zygosity in transgenic plants. 2004. Plant Cell Reports. 23:263-271.

Carroll et al. Determination of the catalytic pathway of C4-leaf pyruvate, orthophosphate dikinase from maize. 1990. Federation of European Biochemical Societies Letters. 274(1-2):178-180.

Chastain et al. Pyruvate, Orthophosphate Dikinase in Leaves and Chloroplasts of C3 Plants Undergoes Light-/Dark-induced Reversible Phosphorylation. 2002. Plant Physiology, 128:1368-1378.

Gan & Amasino. Making Sence of Senescence. 1997. Plant Physiology, 113:313-319.

Harrison et al. A rapid and robust method of identiftying transformed Arabidopsis thaliana seedlings following floral dip transformation. 2006. Plant Methods. 2:19.

Hatch & Slack. A new enzyme for the interconversion of pyruvate and phosphopyruvate and its role in the C4 dicarboxylic acid pathway of photosynthesis. 1968. Biochemical Journal, 106:141-146.

Horsch et al. A simple and general method for transferring genes into plants. 1985. Science. 227:1229-1231.

Jones et al. Measuring plant protein with the Bradford assay. 1989. Journal of Chemical Ecology. 15:979-992.

Pocalyko et al. Analysis of sequence homologies in plant and bacterial pyruvate phosphate dikinase, enzyme I of the bacterial phospoenolpyruvate:sugar phosphotransferase system and other PEP-utilizing enzymes. Identification of potential catalytic and regulatory motifs. 1990. Biochemistry. 29:10757-10765.

Thompson et al. CLUSTAL W: improving the sensitivity of progressive multiple sequence alignment through sequence weighting, position-specific gap penalties and weight matrix choice. 1994. Nucleic Acids Research. 22:4673-4680.

Thompson et al. The CLUSTAL_X windows interface: flexible strategies for multiple sequence alignment aided by quality analysis tools. 1997. Nucleic Acids Research. 24:4876-4882.

van Engelen et al, pBINPLUS: an improved plant transformation vector based on pBIN19. 1995. Transgenic Research. 4:288-290.

\* cited by examiner

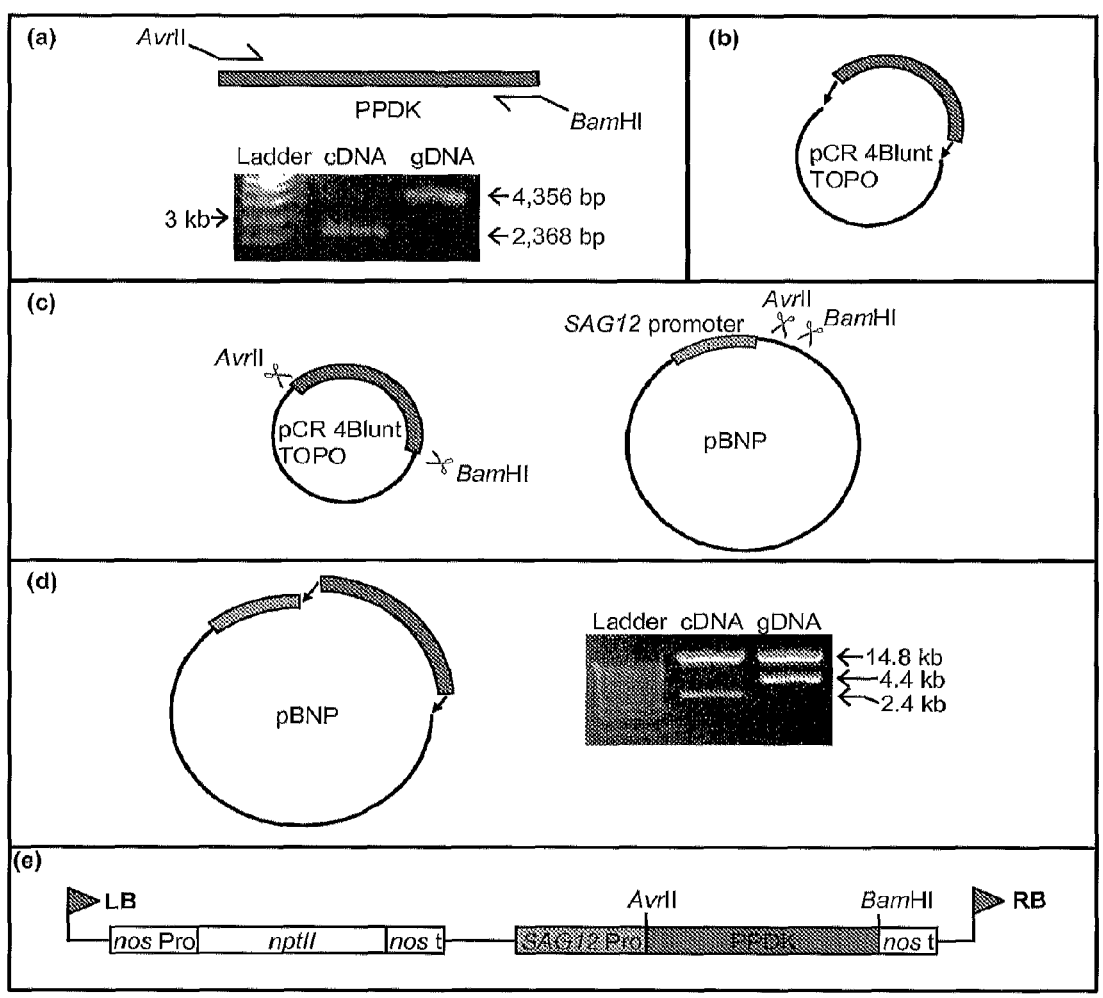
Figure: 1

Figure: 2a

| 5' Site | Insert | 3' Site | Construct Name |
|---|---|---|---|
| AvrII | Arabidopsis PPDK cDNA (cytosolic isoform) | BamHI | TOPO-PPDKcDNA |
| AvrII | Arabidopsis PPDK genomic DNA (cytosolic isoform) | BamHI | TOPO-PPDKgDNA |

Figure: 3a
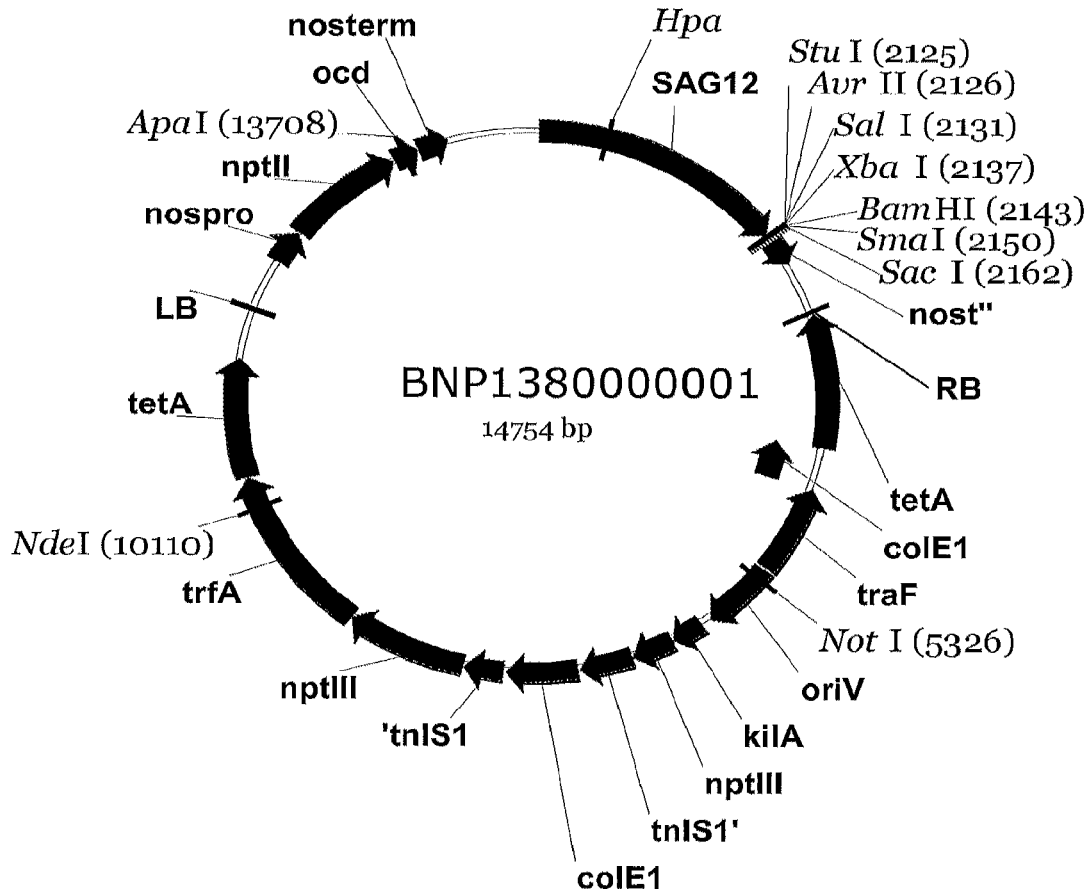
Figure: 3b
| Insert | Location | Construct Name |
|---|---|---|
| Arabidopsis PPDK cDNA (cytosolic isoform) | AvrII-BamHI | BNP-PPDKcDNA |
| Arabidopsis PPDK gDNA (cytosolic isoform) | AvrII-BamHI | BNP-PPDKgDNA |
| Arabidopsis PCK cDNA | XbaI-SacI | pALBNP1 |
| Arabidopsis PCK gDNA | XbaI-SacI | pALBNP2 |

Figure: 4
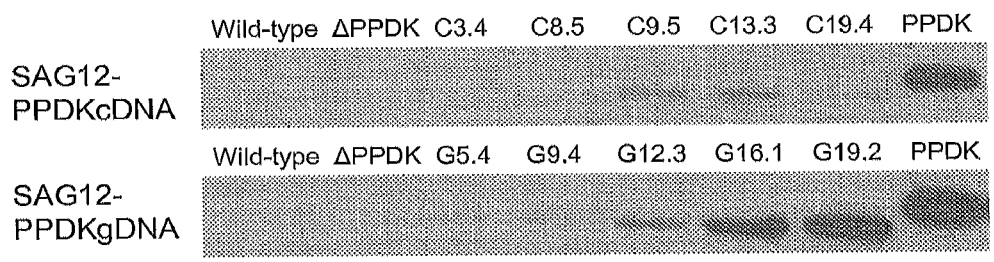
Figure: 5
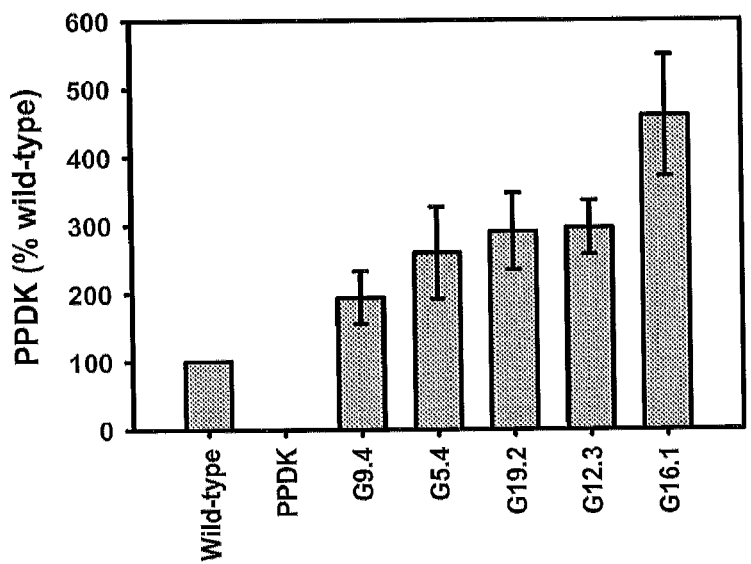

Figure: 6
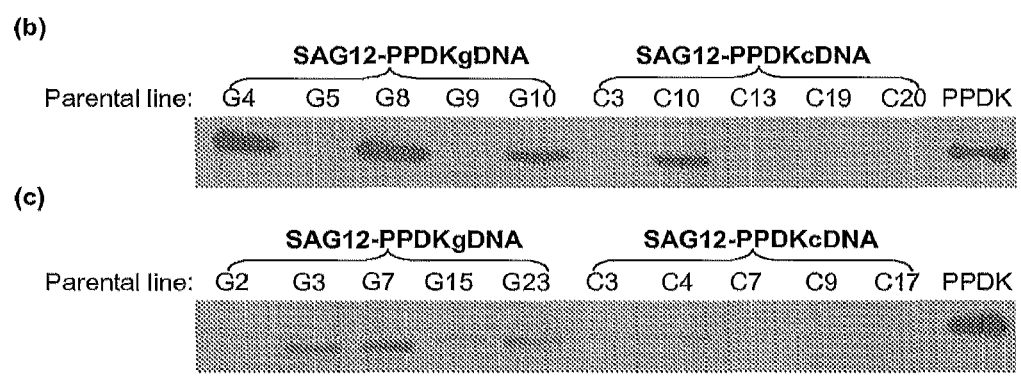
Figure: 7
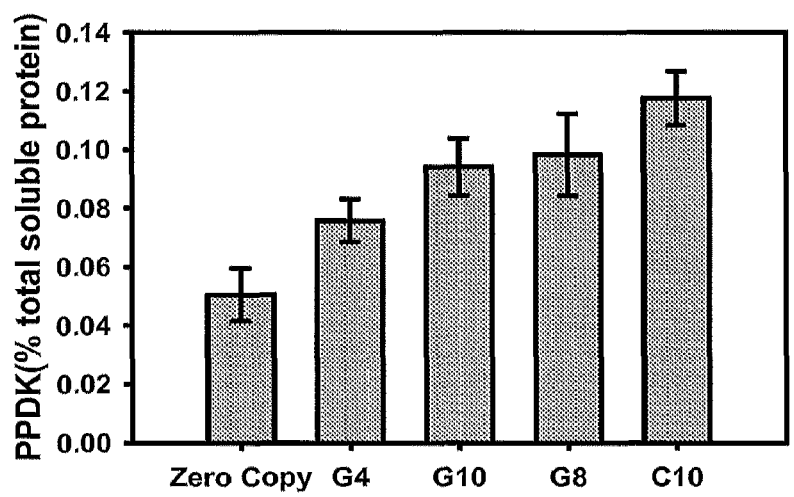

Figure: 8
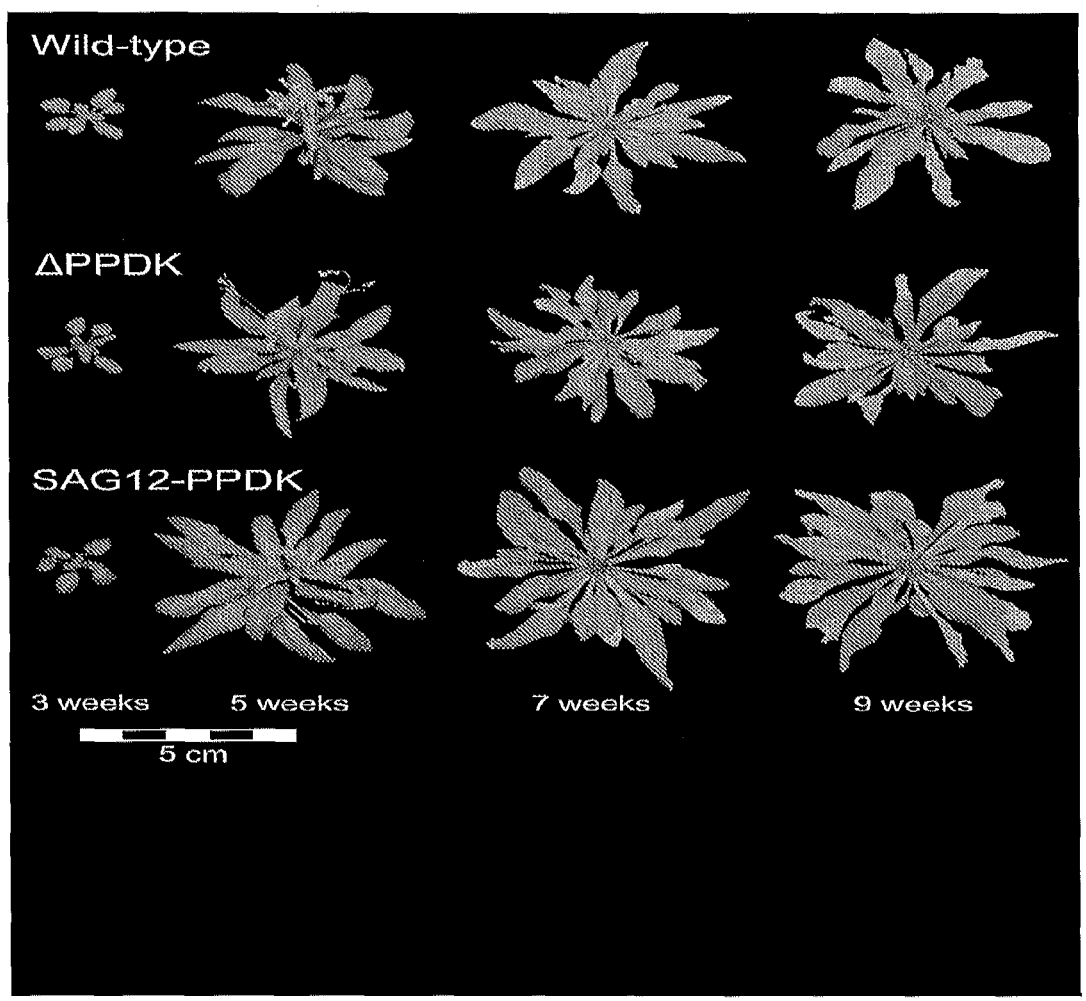

Figure: 9
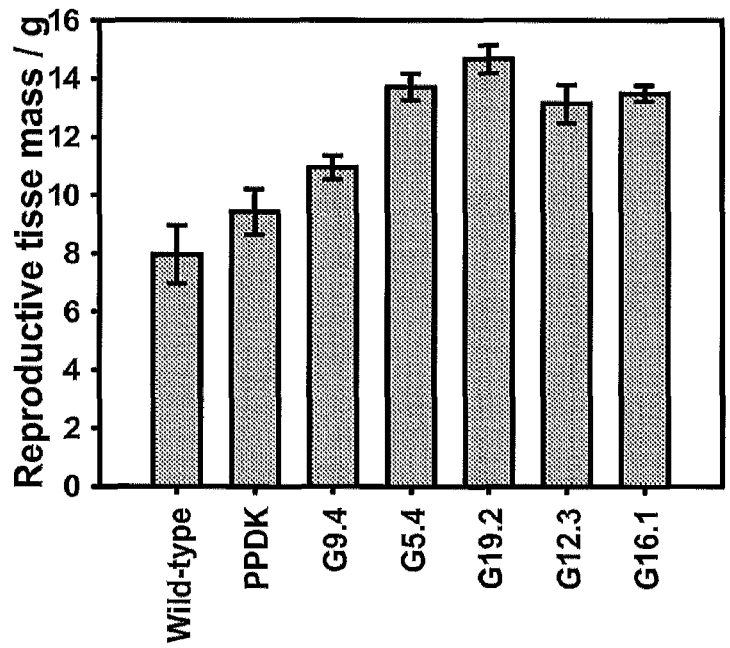
Figure: 10
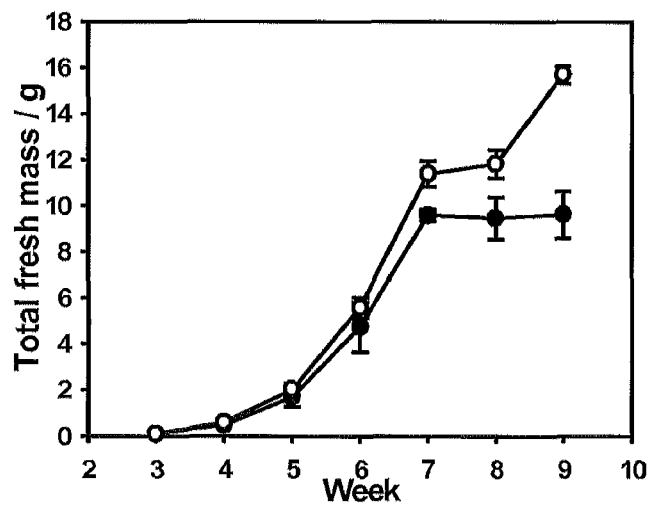

Figure: 11
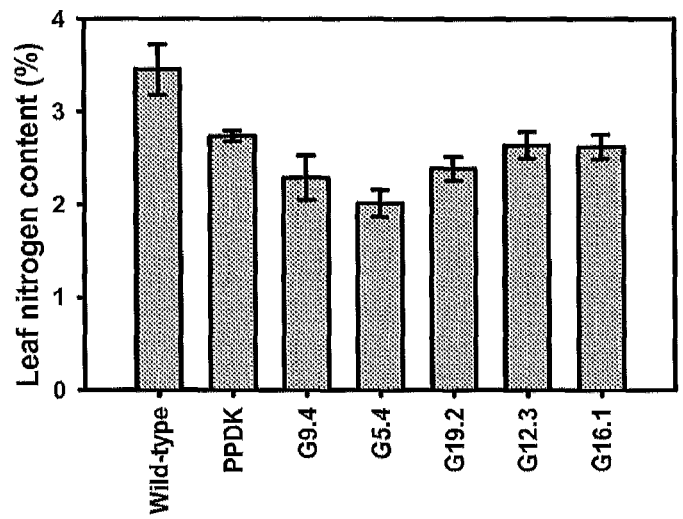
Figure: 12
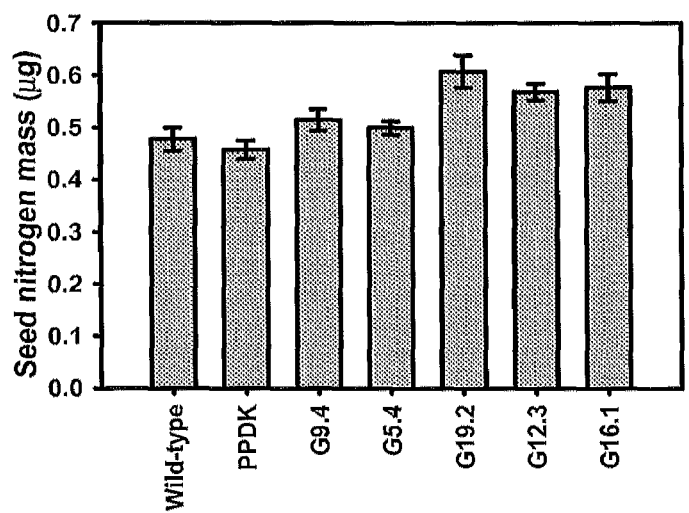

Figure: 13
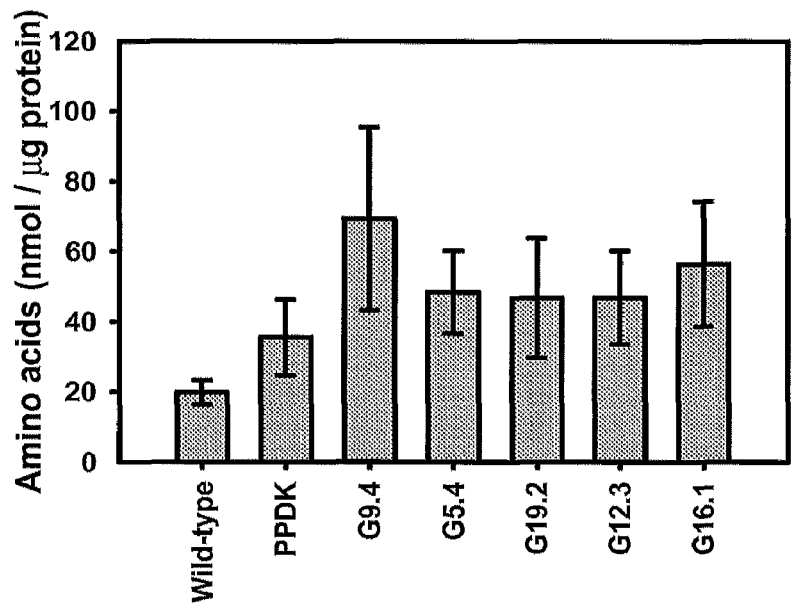
Figure: 14
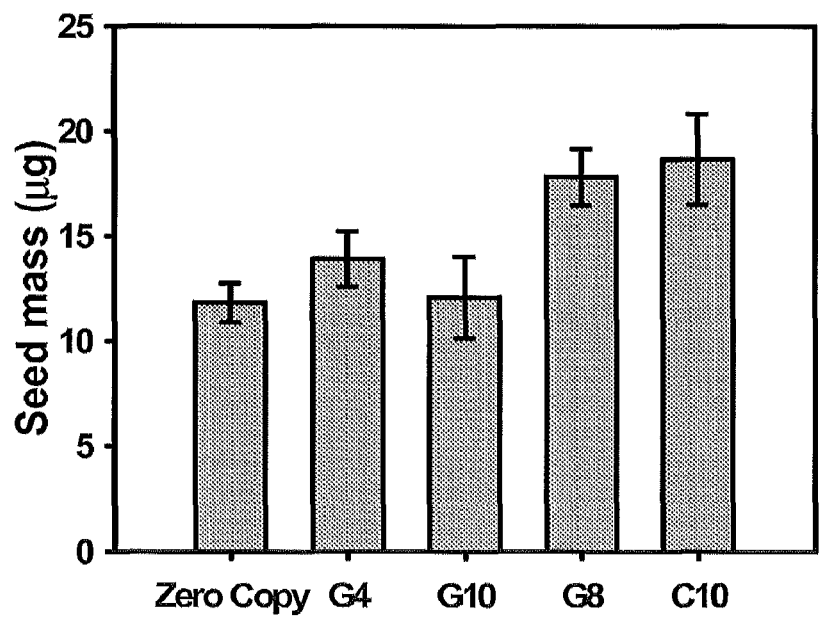

Figure: 15
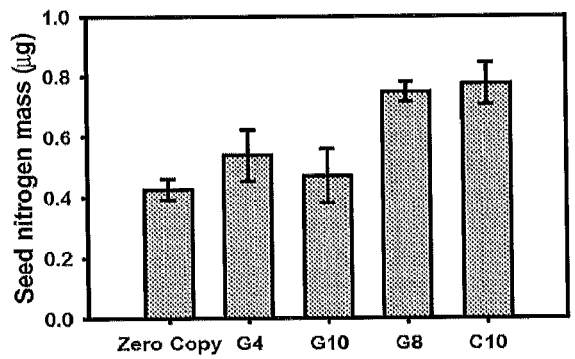
Figure: 16
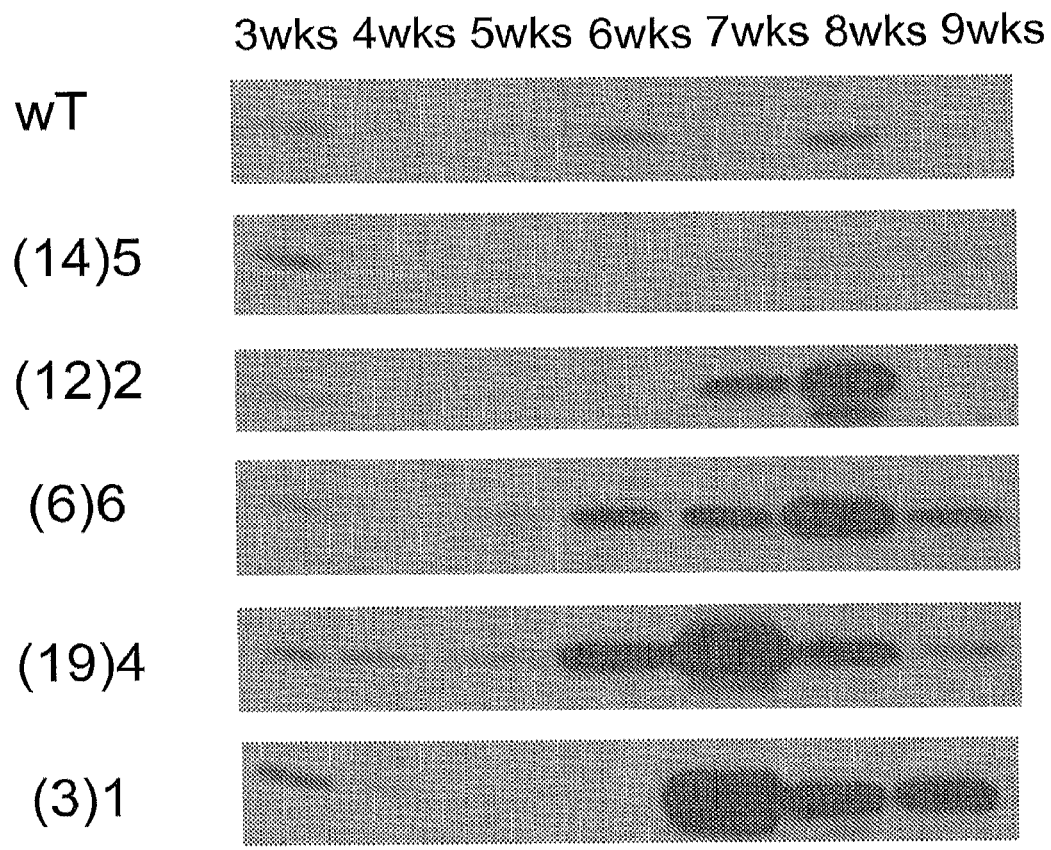

Figure: 17
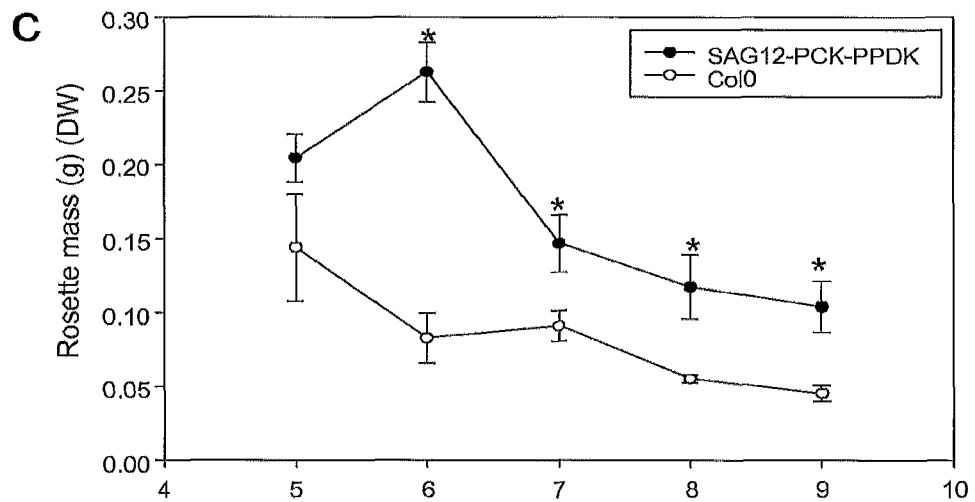
Figure: 18
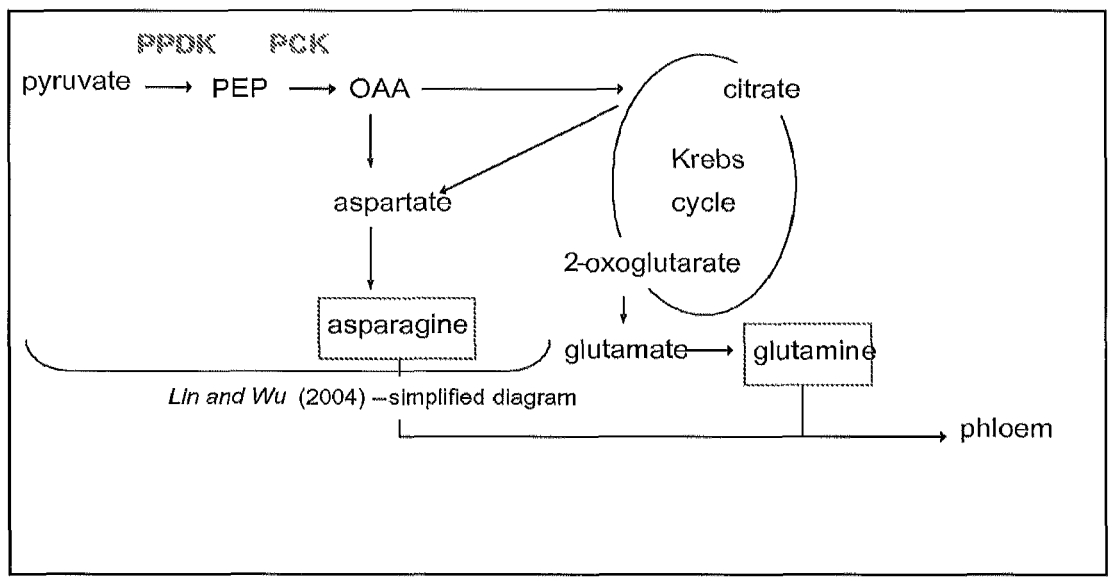

```
                        SEQUENCE LISTING

<160> NUMBER OF SEQ ID NOS: 30

<210> SEQ ID NO 1
<211> LENGTH: 30
<212> TYPE: DNA
<213> ORGANISM: Artificial Sequence
<220> FEATURE:
<223> OTHER INFORMATION: PCR primer

<400> SEQUENCE: 1
aatcctagga tgatgcagcg agtattcacc                                      30

<210> SEQ ID NO 2
<211> LENGTH: 33
<212> TYPE: DNA
<213> ORGANISM: Artificial Sequence
<220> FEATURE:
<223> OTHER INFORMATION: PCR primer

<400> SEQUENCE: 2
aatggatcct catgcaacaa ctacttgagc agc                                  33

<210> SEQ ID NO 3
<211> LENGTH: 21
<212> TYPE: DNA
<213> ORGANISM: Artificial Sequence
<220> FEATURE:
<223> OTHER INFORMATION: PCR primer

<400> SEQUENCE: 3
cttggcttga acgaccaagt c                                               21

<210> SEQ ID NO 4
<211> LENGTH: 21
<212> TYPE: DNA
<213> ORGANISM: Artificial Sequence
<220> FEATURE:
<223> OTHER INFORMATION: PCR primer

<400> SEQUENCE: 4
ggttgcaggg ataggaacac c                                               21

<210> SEQ ID NO 5
<211> LENGTH: 21
<212> TYPE: DNA
<213> ORGANISM: Artificial Sequence
<220> FEATURE:
<223> OTHER INFORMATION: PCR primer

<400> SEQUENCE: 5
cgtctgattg catcagccca g                                               21
```

-continued

<210> SEQ ID NO 6
<211> LENGTH: 21
<212> TYPE: DNA
<213> ORGANISM: Artificial Sequence
<220> FEATURE:
<223> OTHER INFORMATION: PCR primer

<400> SEQUENCE: 6
cctgaggagt tcctacaagt g                                              21

<210> SEQ ID NO 7
<211> LENGTH: 20
<212> TYPE: DNA
<213> ORGANISM: Artificial Sequence
<220> FEATURE:
<223> OTHER INFORMATION: PCR primer

<400> SEQUENCE: 7
cctcgccaaa ggaatcttac                                                20

<210> SEQ ID NO 8
<211> LENGTH: 21
<212> TYPE: DNA
<213> ORGANISM: Artificial Sequence
<220> FEATURE:
<223> OTHER INFORMATION: PCR primer

<400> SEQUENCE: 8
caagaccggc aacaggattc a                                              21

<210> SEQ ID NO 9
<211> LENGTH: 22
<212> TYPE: DNA
<213> ORGANISM: Artificial Sequence
<220> FEATURE:
<223> OTHER INFORMATION: PCR primer

<400> SEQUENCE: 9
accccatctc agtacccttc tg                                             22

<210> SEQ ID NO 10
<211> LENGTH: 19
<212> TYPE: DNA
<213> ORGANISM: Artificial Sequence
<220> FEATURE:
<223> OTHER INFORMATION: PCR primer

<400> SEQUENCE: 10
tgcctgcttg ccgaatatc                                                 19

<210> SEQ ID NO 11
<211> LENGTH: 18
<212> TYPE: DNA
<213> ORGANISM: Artificial Sequence
<220> FEATURE:
<223> OTHER INFORMATION: PCR primer

<400> SEQUENCE: 11
ccggcccaca gtcgatga                                                  18

<210> SEQ ID NO 12
<211> LENGTH: 24
<212> TYPE: DNA
<213> ORGANISM: Artificial Sequence
<220> FEATURE:

```
<223> OTHER INFORMATION: PCR primer

<400> SEQUENCE: 12
cagaaaagcg gccatttttcc acca                                              24

<210> SEQ ID NO 13
<211> LENGTH: 21
<212> TYPE: DNA
<213> ORGANISM: Artificial Sequence
<220> FEATURE:
<223> OTHER INFORMATION: PCR primer

<400> SEQUENCE: 13
ctcaaccttc caccgtgtga t                                                  21

<210> SEQ ID NO 14
<211> LENGTH: 21
<212> TYPE: DNA
<213> ORGANISM: Artificial Sequence
<220> FEATURE:
<223> OTHER INFORMATION: PCR primer

<400> SEQUENCE: 14
accggtgtgc ttcctcttga a                                                  21

<210> SEQ ID NO 15
<211> LENGTH: 22
<212> TYPE: DNA
<213> ORGANISM: Artificial Sequence
<220> FEATURE:
<223> OTHER INFORMATION: PCR primer

<400> SEQUENCE: 15
tctacggtgc caaattcgcc ga                                                 22

<210> SEQ ID NO 16
<211> LENGTH: 2093
<212> TYPE: DNA
<213> ORGANISM: Arabidopsis thaliana

<400> SEQUENCE: 16
tcgagacccg attgttattt ttagactgag acaaaaaagt agaatcgttg attgttaaaa        60
tttaaaatta gtttcattac gtttcgataa aaaaatgatt agtttatcat agcttaatta       120
tagcattgat ttctaaattt gttttttgac caccctttt tctctctttg gtgttttctt        180
aacattagaa gaacccataa caatgtacgt tcaaattaat taaaaacaat atttccaagt       240
tttatatacg aaacttgttt tttttaatga aaacagttga atagttgatt atgaattagt       300
tagatcaata ctcaatatat gatcaatgat gtatatatat gaactcagtt gttatacaag       360
aaatgaaaat gctatttaaa tacagatcat gaagtgttaa aaagtgtcag aatatgacat       420
gaagcgtttt gtcctaccgg gtattcgagt tataggtttg gatctctcaa gaatattttg       480
ggccatacta gttatatttg ggcttaagcg ttttgcaaag agacgaggaa gaaagattgg       540
gtcaagttaa caaaacagag acactcgtat tagttggtac tttggtagca agtcgattta       600
tttgccagta aaaacttggt acacaactga caactcgtat cgttattagt ttgtacttgg       660
tacctttggt tcaagaaaaa gttgatatag ttaaatcagt tgtgttcatg aggtgattgt       720
gatttaattt gttgactagg gcgattcctt cacatcacaa taacaaagtt ttatagattt       780 ttttttata acatttttgc cacgcttcgt aaagtttggt atttacaccg catttttccc        840
tgtacaagaa ttcatatatt atttatttat atactccagt tgacaattat aagtttataa       900
```

```
cgtttttaca attatttaaa taccatgtga agatccaaga atatgtctta cttcttcttt      960
gtgtaagaaa actaactata tcactataat aaaataattc taatcattat atttgtaaat     1020
atgcagttat ttgtcaattt tgaatttagt attttagacg ttatcacttc agccaaatat     1080
gatttggatt taagtccaaa atgcaatttc gtacgtatcc ctcttgtcgt ctaatgatta     1140
tttcaatatt tcttatatta tccctaacta cagagctaca tttatattgt attctaatga     1200
cagggaaacc ttcatagaga ttcagataga tgaaattggt gggaaacatc attgaacagg     1260
aaacttttag caaatcatat cgatttatct acaaagaat  acgtagcgta atgaagtcca     1320
cttgttgtga atgactatga tttgatcaaa ttagttaatt ttgtcgaatc attttctctt     1380
ttgatttgat taagctttta acttgcacga atggttctct tgtgaataaa cagaatcttt     1440
gaattcaaac tatttgatta gtgaaaagac aaaagaagat tccttgtttt tatgtgatta     1500
gtgattttga tgcatgaaag gtacctacgt actacaagaa aaataaacat gtacgtaact     1560
acgtatcagc atgtaaaagt attttttttcc aaataattta tactcatgat agatttttttt  1620
ttttgaaat gtcaattaaa aatgctttct taaatattaa ttttaattaa ttaaataagg      1680
aaatatattt atgcaaaaca tcatcaacac atatccaact tcgaaaatct ctatagtaca     1740
caagtagaga aattaaattt tactagatac aaacttccta atcatcaaat ataaatgttt     1800
acaaaactaa ttaaacccac cactaaaatt aactaaaaat ccgagcaaag tgagtgaaca     1860
agacttgatt tcaggttgat gtaggactaa aatgactacg tatcaaacat caacgatcat     1920
ttagttatgt atgaatgaat gtagtcatta cttgtaaaac aaaaatgctt tgatttggat     1980
caatcacttc atgtgaacat tagcaattac atcaacctta ttttcactat aaaaccccat    2040
ctcagtaccc ttctgaagta atcaaattaa gagcaaaagt catttaactt agg           2093

<210> SEQ ID NO 17
<211> LENGTH: 3358
<212> TYPE: DNA
<213> ORGANISM: Arabidopsis thaliana

<400> SEQUENCE: 17
atgtcggccg gtaacggaaa tgctactaac ggtgacggag ggtttagttt ccctaaagga      60
ccggtgatgc cgaagataac gaccggagca gcaaagagag gtagcggagt ctgccacgac     120
gatagtggtc cgacggtgaa tgccacaacc atcgatgagc ttcattcgtt acagaagaaa     180
cgttctgctc ctaccacacc gatcaaccaa aacgccgccg ctgcttttgc cgccgtctcc     240
gaggaggagc gtcagaagat tcagcttcaa tctatcaggt ccttataata acttcacata     300
tacagattat tcatacgtta cttttgttta aacatactt  tatatcgaat taaggaagat     360
tattgcgttt tcgtgtccga tcattttcat ggaaaaagtg tcttttagct aaatatatgg     420
tgtagtatta aatatttctg acgtgatata cactaaactt gaaaattttc aattactatt     480
tcttcccttta attcggcaat ataatttgtt tttgtttatt tttggattag acatttatgg    540
acaagttaat gcgctattgt gactattacc agaaaataat actttaatgt acatgacacg     600
tgtttaaaac gacacgtgga aactaatttt gattaattgt gaaacagtgc atcgttagca     660
tcgttaacga gagagtcagg accaaaggtg gtgagaggaa atccggcgga gaagaagacc     720
gatggttcaa ctactccggc gtacgctcac ggccaacatc attctatctt ttctccggct     780
actggtgctg tcagtgatag ctccttgaag tttactcacg tcctctacaa tctttcgcct     840
gcaggtcaac aaataaaacct agaatccgaa tctgaatatt gataaatgtt tctgcaacga    900
```

-continued

```
gtttgataga tttggtttgt gattttgttg tttgtagagc tttatgagca agctattaag    960
tatgagaaag gttcgtttat cacttctaat ggagctttgg cgacgctttc tggtgctaag   1020
actggtcgtg ctcccagaga taagcgtgtt gttagagatg ctactactga ggatgagctt   1080
tggtggggaa agtgagtatt cctaatctcg attttgattg atggagtttt tgggtttatg   1140
ctctgttttc gtttattgat tttggagttt gattttgatt ttagggggttc gccgaatatc   1200
gaaatggatg aacatacttt catggtgaac agagaaagag ctgttgatta cttgaattcc   1260
ttggaaaagg tattaaattt tgaaaacttt aatcaatgtt gttgagtgta aacttttga   1320
tctaagttta tgaaatttct gttgttgttg gggttttag gtctttgtca atgaccaata   1380
cttaaactgg gatccagaga acagaatcaa agtcaggatt gtctcagcta gagcttacca   1440
ttcattgttt atgcacaaca tgtaagtaaa atcattattg actccttgta tgtcaatcca   1500
ttattgtggg tgaaagaaaa caacaaatta gtaactgggg agggtgtcag gtgtatccga   1560
ccaactcagg aggagcttga gagctttggt actccggatt ttactatata caatgctggg   1620
cagtttccat gtaatcgtta cactcattac atgacttcgt ccactagcgt agaccttaat   1680
ctggctagga gggaaatggt tatacttggt actcagtatg ctggggaaat gaagaagggt   1740
cttttcagtg tgatgcatta ccttatgcct aagcgtcgta ttctctccct tcattctgga   1800
tgcaatatgg gaaagatgg agatgttgct ctcttctttg gactttcagg tatagtagag   1860
acagtaccaa ctatggtgtt gggtgatgat ggaaggaacg ataaatcaaa tgatacaata   1920
caattactgc tgaactgact tgagaactgc ttgcctcttt gttgagttta gcgggtgaat   1980
tgagattgat gattgtgttt tttgtttct atgaatgatg attttaggta ccgggaagac   2040
aacgctgtct actgatcaca acaggtatct tattggagat gatgagcatt gttggactga   2100
gactggtgtt tcgaacattg agggtgggtg ctatgctaag tgtgttgatc tttcgaggga   2160
gaaggagcct gatatctgga acgctatcaa gtttggaaca ggtagaaaga cagtacgttg   2220
gaattgtttt tgagaaaaaa acataaagca gtgatataac aataagattc tgatcttgtt   2280
gcagttttgg aaaatgttgt gtttgatgag cacaccagag aagtggatta ctctgataaa   2340
tctgttacag gtaaaacaat tgttatttct ttcattctct tcgtcctcac aattaacaga   2400
atgatcattt tcgattctct ttggttgcag agaacacacg tgctgcctac ccaattgagt   2460
tcattccaaa tgcgaaaata ccttgtgttg gtccacaccc gacaaatgtg atacttctgg   2520
cttgtgatgc ctttggtgtt ctcccacctg tgagcaagct gaatctggca caaaccatgt   2580
accacttcat cagtggttac actgctctgg taaggccaaa gtaaaagtct ttattttgca   2640
catcgtcttc ataaatttca aaagcataac caaagatgtg caacatatat aggttgctgg   2700
cacagaggat ggtatcaagg agccaacagc aacattctca gcttgctttg gtgcagcttt   2760
cataatgttg catcccacaa agtatgcagc tatgttagct gagaagatga agtcacaagg   2820
tgctactggt tggctcgtca acactggttg gtctggtggc aggtatatat gtccttctat   2880
ggaaatcgat acaacaaaac gctgccttgt aacacatgtt tgtaggctat aacatgatc   2940
tgtaatgttt tatttcctgc agttatggtg ttggaaacag aatcaagctg gcatacacta   3000
gaaagatcat cgatgcaatc cattcgggca gtctcttgaa ggcaaactac aagaaaaccg   3060
aaatctttgg atttgaaatc ccaactgaga tcgaagggat accttcagag atcttggacc   3120
ccgtcaactc cgtaagtttc tgcaaatctg tataatgtaa ttgcttaagt gatgatgaac   3180
aattttttgt tgatttgggt ttaatgaaaa tgcagtggtc tgataagaag gcacacaaag   3240
atactctggt gaaactggga ggtctgttca agaagaactt cgaggttttt gctaaccata   3300
```
agattggtgt gatggtaagc ttacggagga gattctcgct gctggtccta tcttttag    3358

<210> SEQ ID NO 18
<211> LENGTH: 2015
<212> TYPE: DNA
<213> ORGANISM: Arabidopsis thaliana

<400> SEQUENCE: 18

```
atgtcggccg gtaacggaaa tgctactaac ggtgacggag ggtttagttt ccctaaagga      60
ccggtgatgc cgaagataac gaccggagca gcaaagagag gtagcggagt ctgccacgac     120
gatagtggtc cgacggtgaa tgccacaacc atcgatgagc ttcattcgtt acagaagaaa     180
cgttctgctc ctaccacacc gatcaaccaa aacgccgccg ctgcttttgc cgccgtctcc     240
gaggaggagc gtcagaagat tcagcttcaa tctatcagtg catcgttagc atcgttaacg     300
agagagtcag gaccaaaggt ggtgagagga gatccggcgg agaagaagac cgatggttca     360
actactccgg cgtacgctca cggccaacat cattctatct tttctccggc tactggtgct     420
gtcagtgata gctccttgaa gtttactcac gtcctctaca atctttcgcc tgcagagctt     480
tatgagcaag ctattaagta tgagaaaggt tcgtttatca cttctaatgg agctttggcg     540
acgctttctg gtgctaagac tggtcgtgct cccagagata agcgtgttgt tagagatgct     600
actactgagg atgagctttg gtggggaaag ggttcgccga atatcgaaat ggatgaacat     660
actttcatgg tgaacagaga aagagctgtt gattacttga attccttgga aaaggtcttt     720
gtcaatgacc aatacttaaa ctgggatcca gagaacagaa tcaaagtcag gattgtctca     780
gctagagctt accattcatt gtttatgcac aacatgtgta tccgaccaac tcaggaggag     840
cttgagagct ttggtactcc ggattttact atatacaatg ctgggcagtt tccatgtaat     900
cgttacactc attacatgac ttcgtccact agcgtagacc ttaatctggc taggagggaa     960
atggttatac ttggtactca gtatgctggg gaaatgaaga agggtctttt cagtgtgatg    1020
cattacctta tgcctaagcg tcgtattctc tcccttcatt ctggatgcaa tatgggaaaa    1080
gatggagatg ttgctctctt ctttggactt tcaggtaccg ggaagacaac gctgtctact    1140
gatcacaaca ggtatcttat tggagatgat gagcattgtt ggactgagac tggtgtttcg    1200
aacattgagg gtgggtgcta tgctaagtgt gttgatcttt cgagggagaa ggagcctgat    1260
atctggaacg ctatcaagtt tggaacagtt ttggaaaatg ttgtgtttga tgagcacacc    1320
agagaagtgg attactctga taaatctgtt acagagaaca cacgtgctgc ctacccaatt    1380
gagttcattc caaatgcgaa aataccttgt gttggtccac acccgacaaa tgtgatactt    1440
ctggcttgtg atgcctttgg tgttctccca cctgtgagca agctgaatct ggcacaaacc    1500
atgtaccact tcatcagtgg ttacactgct ctggttgctg gcacagagga tggtatcaag    1560
gagccaacag caacattctc agcttgcttt ggtgcagctt tcataatgtt gcatcccaca    1620
aagtatgcag ctatgttagc tgagaagatg aagtcacaag gtgctactgg ttggctcgtc    1680
aacactggtt ggtctggtgg cagttatggt gttggaaaca gaatcaagct ggcatacact    1740
agaaagatca tcgatgcaat ccattcgggc agtctcttga aggcaaaacta caagaaaacc    1800
gaaatctttg gatttgaaat cccaactgag atcgaaggga taccttcaga gatcttggac    1860
cccgtcaact cctggtctga taagaaggca cacaaagata tctctggtga aactgggaggt    1920
ctgttcaaga agaacttcga ggttttttgct aaccataaga ttggtgtgat ggtaagctta    1980
cggaggagat tctcgctgct ggtcctatct tttag                                2015
```

<210> SEQ ID NO 19
<211> LENGTH: 671
<212> TYPE: PRT
<213> ORGANISM: Arabidopsis thaliana

<400> SEQUENCE: 19

```
Met Ser Ala Gly Asn Gly Asn Ala Thr Asn Gly Asp Gly Gly Phe Ser
1               5                   10                  15

Phe Pro Lys Gly Pro Val Met Pro Lys Ile Thr Thr Gly Ala Ala Lys
            20                  25                  30

Arg Gly Ser Gly Val Cys His Asp Asp Ser Gly Pro Thr Val Asn Ala
        35                  40                  45

Thr Thr Ile Asp Glu Leu His Ser Leu Gln Lys Lys Arg Ser Ala Pro
50                  55                  60

Thr Thr Pro Ile Asn Gln Asn Ala Ala Ala Phe Ala Ala Val Ser
65                  70                  75                  80

Glu Glu Glu Arg Gln Lys Ile Gln Leu Gln Ser Ile Ser Ala Ser Leu
                85                  90                  95

Ala Ser Leu Thr Arg Glu Ser Gly Pro Lys Val Val Arg Gly Asp Pro
            100                 105                 110

Ala Glu Lys Lys Thr Asp Gly Ser Thr Thr Pro Ala Tyr Ala His Gly
        115                 120                 125

Gln His His Ser Ile Phe Ser Pro Ala Thr Gly Ala Val Ser Asp Ser
130                 135                 140

Ser Leu Lys Phe Thr His Val Leu Tyr Asn Leu Ser Pro Ala Glu Leu
145                 150                 155                 160

Tyr Glu Gln Ala Ile Lys Tyr Glu Lys Gly Ser Phe Ile Thr Ser Asn
                165                 170                 175

Gly Ala Leu Ala Thr Leu Ser Gly Ala Lys Thr Gly Arg Ala Pro Arg
            180                 185                 190

Asp Lys Arg Val Val Arg Asp Ala Thr Thr Glu Asp Glu Leu Trp Trp
        195                 200                 205

Gly Lys Gly Ser Pro Asn Ile Glu Met Asp Glu His Thr Phe Met Val
210                 215                 220

Asn Arg Glu Arg Ala Val Asp Tyr Leu Asn Ser Leu Glu Lys Val Phe
225                 230                 235                 240

Val Asn Asp Gln Tyr Leu Asn Trp Asp Pro Glu Asn Arg Ile Lys Val
                245                 250                 255

Arg Ile Val Ser Ala Arg Ala Tyr His Ser Leu Phe Met His Asn Met
            260                 265                 270

Cys Ile Arg Pro Thr Gln Glu Glu Leu Glu Ser Phe Gly Thr Pro Asp
        275                 280                 285

Phe Thr Ile Tyr Asn Ala Gly Gln Phe Pro Cys Asn Arg Tyr Thr His
290                 295                 300

Tyr Met Thr Ser Thr Ser Val Asp Leu Asn Leu Ala Arg Arg Glu
305                 310                 315                 320

Met Val Ile Leu Gly Thr Gln Tyr Ala Gly Glu Met Lys Lys Gly Leu
                325                 330                 335

Phe Ser Val Met His Tyr Leu Met Pro Lys Arg Arg Ile Leu Ser Leu
            340                 345                 350

His Ser Gly Cys Asn Met Gly Lys Asp Gly Asp Val Ala Leu Phe Phe
        355                 360                 365

Gly Leu Ser Gly Thr Gly Lys Thr Thr Leu Ser Thr Asp His Asn Arg
370                 375                 380
```

```
Tyr Leu Ile Gly Asp Asp Glu His Cys Trp Thr Glu Thr Gly Val Ser
385                 390                 395                 400

Asn Ile Glu Gly Gly Cys Tyr Ala Lys Cys Val Asp Leu Ser Arg Glu
            405                 410                 415

Lys Glu Pro Asp Ile Trp Asn Ala Ile Lys Phe Gly Thr Val Leu Glu
        420                 425                 430

Asn Val Val Phe Asp Glu His Thr Arg Glu Val Asp Tyr Ser Asp Lys
    435                 440                 445

Ser Val Thr Glu Asn Thr Arg Ala Ala Tyr Pro Ile Glu Phe Ile Pro
450                 455                 460

Asn Ala Lys Ile Pro Cys Val Gly Pro His Pro Thr Asn Val Ile Leu
465                 470                 475                 480

Leu Ala Cys Asp Ala Phe Gly Val Leu Pro Pro Val Ser Lys Leu Asn
            485                 490                 495

Leu Ala Gln Thr Met Tyr His Phe Ile Ser Gly Tyr Thr Ala Leu Val
        500                 505                 510

Ala Gly Thr Glu Asp Gly Ile Lys Glu Pro Thr Ala Thr Phe Ser Ala
    515                 520                 525

Cys Phe Gly Ala Ala Phe Ile Met Leu His Pro Thr Lys Tyr Ala Ala
530                 535                 540

Met Leu Ala Glu Lys Met Lys Ser Gln Gly Ala Thr Gly Trp Leu Val
545                 550                 555                 560

Asn Thr Gly Trp Ser Gly Ser Tyr Gly Val Gly Asn Arg Ile Lys
            565                 570                 575

Leu Ala Tyr Thr Arg Lys Ile Ile Asp Ala Ile His Ser Gly Ser Leu
        580                 585                 590

Leu Lys Ala Asn Tyr Lys Lys Thr Glu Ile Phe Gly Phe Glu Ile Pro
    595                 600                 605

Thr Glu Ile Glu Gly Ile Pro Ser Glu Ile Leu Asp Pro Val Asn Ser
610                 615                 620

Trp Ser Asp Lys Lys Ala His Lys Asp Thr Leu Val Lys Leu Gly Gly
625                 630                 635                 640

Leu Phe Lys Lys Asn Phe Glu Val Phe Ala Asn His Lys Ile Gly Val
            645                 650                 655

Met Val Ser Leu Arg Arg Arg Phe Ser Leu Leu Val Leu Ser Phe
        660                 665                 670

<210> SEQ ID NO 20
<211> LENGTH: 5753
<212> TYPE: DNA
<213> ORGANISM: Arabidopsis thaliana

<400> SEQUENCE: 20
atgacaagta tgatcgtgaa gacaacgccg gagctcttca aaggaaatgg agtgttccgt      60
acggatcatc tcggagaaaa ccgaatggtt agtcgatcaa accggctagg tgatggatca     120
aaccgtttcc ctagaaccgg tacaatccat tgccaacggt taagcatagc aaagaccggt     180
ttgcatcgtg agacgaaggc tcgagccata cttagccctg tgtccgatcc ggccgcttcc     240
atagcccaaa aggtaagcct ttccatttca atcattctgg tgtattttca ccataaaatt     300
ttatacactt ttttattacg ttttgtttta tgattctgac gtgagattct tgagagaaac     360
tatcaccgat cattgggtcg aaccatctag cagctcaatt attatcggtt ataaccctac     420
cggttataga atacaaaaca ggttacgcca ttgtgacatt tgctttgtga tcttgtgaga     480
```

```
cgattaatta tttgatgttg attggtttcg ttactcttgt ttaaacaatc gaacggttca    540
aactaataca cacatgtgat gtgagatcat ttcggtagta ataccaaata gcgtctggcc    600
taaattatga aagtactatt ttgaattaaa ttattgtgga aacatgaact tatttaaatt    660
caagtatttt cgaaatttgt aataaaaaaa aacttttcct ctagattcat tagccctact    720
tttcgtagaa acaactttaa tgtattcaaa gaccactttg ctgcttaagt cagactcttg    780
tgccacttgg tagatccacc aatgccacgt tttgttattg tgccaaagaa tacgtgaata    840
tgtccaaacg gcaatcaaat tcttggcgta aaacacaaaa attatgatac tagtttaaat    900
ccacaattca ccttcaccat aaagaattca tgtattagag atggtatgac aagaactggt    960
tgaatttgat gacatttgtt tgctattgtt ttggttaagt aaaagttttg ttaaaaagga   1020
aaatagcatc ggtagtggca gatagcaagt gtgtgagtga gatcagatat ggttgacaca   1080
tctatgacga gtcatcgcaa cgaaacttct ttaattttgg tcaattatat tacaatttag   1140
catttcgagg ttggaatttt ggaatgatct cttgataaga taataatgta tttttgatga   1200
cgtatccatc aaaactataa atgatttata ttaaatatga aatttcgact gtatacaagt   1260
ttttatatta taaaattatt cgatgtacat atgatcataa taactttact atatatatag   1320
atacgtatat gtgttcttaa acttgcacaa acatttctgc aatctaaacc tcaatcaaaa   1380
caaacaaaca aaaaaccatg atgcagcgag tattcacctt tggaaaagga agaagcgaag   1440
gcaacaaggg catgaagtcc ttggtatgtt accaatacca tcatcatgat catatcaatt   1500
cattaataat ttagtgtttg ctattttcaa gaaccattta tcaaaaatgt taattgttgt   1560
tgtgtatgaa gttgggaggg aaaggagcca acctggcgga gatggctagc ataggcttgt   1620
cggtgccgcc ggggctaacc atatcgacgg aggcttgtca gcagtatcag atcgccggca   1680
aaaagcttcc agaaggttta tgggaagaga tcttagaagg tcttagcttc atcgaacgtg   1740
acattggagc ttccctcgct gatccctcca agccactcct cctctctgtt cgctccggcg   1800
ccgccgtaag ttaattataa ctttttttct tgactatttt tattttaagg attttttcta   1860
atgttaaatt tctgttttttt tttctttcta tgttttcttt aatcttttga agatttttg    1920 acgcagattt tgacttgtta gatttctttt attgaagttg agatccaaat attttttgg    1980 ttatttgcc atttggccgt ttttggaaga gtttaaaatg tactagatag aaaatgaata    2040
agttttgtgg ctattgaaag acctaatgat tttggtattc aaactataac gtagaaaatg   2100
aagatctttc gtttatctat ttttaaaaca gaactacatt gacttgtctt tgatcgatat   2160
tttgcattgt agatctcaat gcctggtatg atggacactg tacttaacct tggcttgaac   2220
gaccaagtcg tcgttggtct ggccgcaaaa agcggagagc gttttgctta cgattcgttc   2280
cggcgttttc ttgatatgtt tggtgatgtt gtaagtcctc tgttttcaa tactatttca    2340 ggtaacttgc atgacaagaa aattctttga cctaccttat aattgttttc ttgatcaata   2400
aaaggtgatg ggaattccac acgccaagtt tgaagagaag ttagagagaa tgaaggagag   2460
gaaaggagtt aaaaatgaca ctgacttaag cgcggctgat ctcaaggaat tggttgagca   2520
gtacaagagt gtttacttag aggccaaggg tcaagagttt ccttcaggtt tgttttgatt   2580
cctacttgag gtcaagtgat aaaaattagt tattagttac aaatgtttaa acggggttaa   2640
ttgcagatcc aaagaagcaa ttggagctag cgattgaagc ggtattcgat tcttgggata   2700
gcccgagagc gaacaagtac agaagtatta accagataac tggattgaaa ggaaccgcgg   2760
ttaacattca gtgtatggtg tttggaaaca tgggggacac ttcagggact ggtgttctct   2820
tcactaggaa ccctagcaca ggagagaaga agctttatgg cgagtttcta gttaatgctc   2880
```

-continued

```
aggtttggca tctatcacaa tgtgtgaatc tcatatcaac aagtaagccc atactcatta   2940
aatattggtt ttgggacagg gagaggatgt ggttgcaggg ataagaacac cagaagattt   3000
ggatacaatg aagagattta tgcctgaggc ttacgctgaa cttgttgaga actgcaacat   3060
cttagaaaga cattacaaag acatgatggt tgatacacat aaacaatact tcaattagtc   3120
ctcatcaaca attctttagt aatttaaaca aaatctcaaa tgtgtattgc aggatattga   3180
attcacagta caagaagaga gattgtggat gctgcaatgc agagcgggta agcgaacggg   3240
taaaggcgcc gtgaagatag cagttgatat ggtaggtgaa gggcttgttg agaaatcttc   3300
tgctatcaaa atggtggagc ctcaacatct tgatcaacta cttcacccac aggtacaaac   3360
tcaaatattc atcttcttct tttttcatag tcataaactt gatgttgaaa ccaaaattcg   3420
aaacttactg gtaatgattg gttcacttga acaagaacta atgggtttaa gacgtttagg   3480
gtttaggagt aaaagcagag atgattgtct gacacgtaac cgatgaatag ggtttggaaa   3540
ttttgattca gaggtcaatg aaggtttttt tttttttttt ttattgatgg attagtttca   3600
tgatccatcg gggtatcgtg aaaaagtggt ggccaaaggc ttacctgcgt caccaggagc   3660
ggcggttgga caggttgtgt tcacggcgga ggaagccgaa gcttggcatt ctcagggtaa   3720
aactgtgatt ctggttcgaa ctgagacaag ccctgacgat gtgggaggta tgcacgcagc   3780
ggaaggtata ttgacggcta gaggaggaat gacgtcacac gcggctgttg ttgctcgcgg   3840
ttggggaaaa tgttgcattg ctggttgttc cgagattcgt gtcgacgaga accacaaggt   3900
ttttggattc gattttagaa acttgtcata taagttaggg gaagattgtt tctaaagtta   3960
gggtttaaaa attttcaggt tctattgatt ggagatttga cgattaatga aggcgaatgg   4020
atctcaatga acggatcaac cggtgaggtt atattaggga aacaagcatt ggctcctccg   4080
gctttaagtc cagatttgga gactttcatg tcctgggctg atgcaatcag acgtctcaag   4140
gtgtttatga gttctgttc ctttaacttg tttgatattt ttaaactttc taactcaaat   4200
gttcgatgac cgataaggtt atggcgaatg cggatacacc tgaagacgcc attgcagcta   4260
ggaaaaacgg agctcaagga atcgggcttt gtaggacaga gcatatggta actcctcctc   4320
tgtacttgat ttcatgtttt tgatgattta gattgtttgt atccaaatgt ttaatgttgt   4380
ctttggtttg gttttttaagt tctttggagc agataggatt aaagcagtga gaaagatgat   4440
aatggcggta acaacagagc aaaggaaagc ttctctcgac atcttgcttc cttaccaacg   4500
ttcggatttc gaagggatct tccgtgctat ggatggtaaa tgttttgagt cgtctctcta   4560
aaatgtatca caacttaaaa catgcctaaa ccttttttatt tttctaggtt taccggtaac   4620
aatccgtttg ttagaccctc cgcttcacga gtttctcccg gaaggcgact tggacaacat   4680
tgtacatgag ctagctgaag aaactggtgt gaaagaagat gaagtcttgt cacggataga   4740
gaaactctct gaagtgaatc caatgcttgg tttccgcggt tgcaggtttc ttactctctt   4800
tgtttctctc tgtctctttg cacctgaaga acaatctgat gatcggtaaa cttgtacgtt   4860
ataggctcgg aatatcgtat ccagagctaa cggagatgca agcgcgtgca atttttgaag   4920
ctgcagcgtc aatgcaggac caaggtgtta ctgtcattcc tgagattatg gttccacttg   4980
taggaactcc tcaggaattg ggtcaccaag ttgatgtaat tcgtaaagtt gcaagaaaag   5040
tatttgctga gaagggtcat accgtgagct acaaggttgg gacaatgatt gagatccctc   5100
gagccgcgct cattgcagat gaggtaaatg taacaagaca caaaatgtgt ttaggcact   5160 tgaaaccatg ttgctatttg ctaagtagga accttttttct tttgacagat tgcgaaagag   5220
```

```
gcggagtttt tctcgttcgg gacaaacgac ttgacgcaga tgacgtttgg atacagtaga    5280
gacgatgtcg gcaagtttct accgatttac ctcgccaaag gaatcttaca gcacgaccct    5340
tttgaggtat aatgactacc atttcgtttg ctctctatcc ataggataaa atcttgatag    5400
ccattttttt gtgtttggac caggttcttg atcagcaagg tgtagggcaa ttgatcaaga    5460
tggcgacaga aaaggacga gcagctaggc ctagcctcaa ggttgggata tgtggagaac    5520
atggaggaga tccatcttct gtgggattct tgctgaagc aggacttgac tatgtctctt    5580
gttctccttt caggtaattg attaatttcc aaccaataa acactttttt tacaacacta    5640
ttgtataact cagattgatg taattttggg atttctgttg ttgttgttgt tgttgttgtt    5700
gttgcagggt tccaattgca aggcttgcag ctgctcaagt agttgttgca tga           5753

<210> SEQ ID NO 21
<211> LENGTH: 2697
<212> TYPE: DNA
<213> ORGANISM: Arabidopsis thaliana

<400> SEQUENCE: 21
atgatgcagc gagtattcac ctttggaaaa ggaagaagcg aaggcaacaa gggcatgaag      60
tccttgttgg gagggaaagg agccaacctg gcggagatgg ctagcatagg cttgtcggtg     120
ccgccggggc taaccatatc gacggaggct tgtcagcagt atcagatcgc cggcaaaaag     180
cttccagaag gtttatggga agagatctta gaaggtctta gcttcatcga acgtgacatt     240
ggagcttccc tcgctgatcc ctccaagcca ctcctcctct ctgttcgctc cggcgccgcc     300
atctcaatgc ctggtatgat ggacactgta cttaaccttg gcttgaacga ccaagtcgtc     360
gttggtctgg ccgcaaaaag cggagagcgt tttgcttacg attcgttccg gcgttttctt     420
gatatgtttg gtgatgttgt gatgggaatt ccacacgcca gtttgaaga aagttagag      480 agaatgaagg agaggaaagg agttaaaaat gacactgact aagcgcggc tgatctcaag     540 gaattggttg agcagtacaa gagtgtttac ttagaggcca agggtcaaga gttccttca      600 gatccaaaga agcaattgga gctagcgatt gaagcggtat cgattcttg ggatagcccg      660 agagcgaaca agtacagaag tattaaccag ataactggat tgaaaggaac gcggttaac      720 attcagtgta tggtgtttgg aaacatgggg gacacttcag ggactggtgt tctcttcact     780 aggaaccta gcacaggaga gaagaagctt atggcgagt ttctagttaa tgctcaggtt      840
tggcatctat cacaatgtgt gaatctcata tcaacaagga taagaacacc agaagatttg     900
gatacaatga agagatttat gcctgaggct tacgctgaac ttgttgagaa ctgcaacatc     960
ttagaaagac attacaaaga catgatggat attgaattca cagtacaaga agagagattg    1020
tggatgctgc aatgcagagc gggtaagcga acgggtaaag gcgccgtgaa gatagcagtt    1080
gatatggtag gtgaagggct tgttgagaaa tcttctgcta tcaaaatggt ggagcctcaa    1140
catcttgatc aactacttca cccacagttt catgatccat cggggtatcg tgaaaaagtg    1200
gtggccaaag gcttacctgc gtcaccagga gcggcggttg acaggttgt gttcacggcg    1260 gaggaagccg aagcttggca ttctcagggt aaaactgtga ttctggttcg aactgagaca    1320
agccctgacg atgtgggagg tatgcacgca gcggaaggta tattgacggc tagaggagga    1380
atgacgtcac acgcggctgt tgttgctcgc ggttgggaa aatgttgcat gctggttgt     1440 tccgagattc gtgtcgacga gaaccacaag gttctattga ttggagattt gacgattaat    1500
gaaggcgaat ggatctcaat gaacggatca accggtgagg ttatattagg gaaacaagca    1560
ttggctcctc cggctttaag tccagatttg gagactttca tgtcctgggc tgatgcaatc    1620
```

-continued

```
agacgtctca aggttatggc gaatgcggat acacctgaag acgccattgc agctaggaaa    1680
aacggagctc aaggaatcgg gctttgtagg acagagcata tgattgtttg tatccaaatg    1740
tttaatgttg tctttggttt ggttttaag ttctttggag cagataggat taaagcagtg     1800
agaaagatga taatggcggt aacaacagag caaaggaaag cttctctcga catcttgctt    1860
ccttaccaac gttcggattt cgaagggatc ttccgtgcta tggatggttt accggtaaca    1920
atccgtttgt tagaccctcc gcttcacgag tttctcccgg aaggcgactt ggacaacatt    1980
gtacatgagc tagctgaaga aactggtgtg aagaagatg aagtcttgtc acggatagag      2040
aaactctctg aagtgaatcc aatgcttggt tccgcggtt gcaggctcgg aatatcgtat     2100
ccagagctaa cggagatgca agcgcgtgca atttttgaag ctgcagcgtc aatgcaggac    2160
caaggtgtta ctgtcattcc tgagattatg gttccacttg taggaactcc tcaggaattg    2220
ggtcaccaag ttgatgtaat tcgtaaagtt gcaaagaaag tatttgctga agggtcat      2280 accgtgagct acaaggttgg gacaatgatt gagatccctc gagccgcgct cattgcagat    2340
gagattgcga agaggcgga gttttttctcg ttcgggacaa cgacttgac gcagatgacg     2400 tttggataca gtagagacga tgtcggcaag tttctaccga tttacctcgc caaaggaatc    2460
ttacagcacg accctttga ggttcttgat cagcaaggtg tagggcaatt gatcaagatg     2520
gcgacagaaa aaggacgagc agctaggcct agcctcaagg ttgggatatg tggagaacat    2580
ggaggagatc catcttctgt gggattcttt gctgaagcag gacttgacta tgtctcttgt    2640
tctcctttca gggttccaat tgcaaggctt gcagctgctc aagtagttgt tgcatga      2697
```

<210> SEQ ID NO 22
<211> LENGTH: 2940
<212> TYPE: DNA
<213> ORGANISM: Arabidopsis thaliana

<400> SEQUENCE: 22

```
atgacaagta tgatcgtgaa gacaacgccg gagctcttca aaggaaatgg agtgttccgt    60
acggatcatc tcggagaaaa ccgaatggtt agtcgatcaa accggctagg tgatggatca    120
aaccgtttcc ctagaaccgg tacaatccat tgccaacggt taagcatagc aaagaccggt    180
ttgcatcgtg agacgaaggc tcgagccata cttagccctg tgtccgatcc ggccgcttcc    240
atagcccaaa agcgagtatt caccttttgga aaaggaagaa gcgaaggcaa caagggcatg    300
aagtccttgt tgggagggaa aggagccaac ctggcggaga tggctagcat aggcttgtcg    360
gtgccgccgg ggctaaccat atcgacgag gcttgtcagc agtatcagat cgccggcaaa    420
aagcttccag aaggtttatg ggaagagatc ttagaaggtc ttagcttcat cgaacgtgac    480
attggagctt ccctcgctga tccctccaag ccactcctcc tctctgttcg ctccggcgcc    540
gccatctcaa tgcctggtat gatggacact gtacttaacc ttggcttgaa cgaccaagtc    600
gtcgttggtc tggccgcaaa aagcggagag cgttttgctt acgattcgtt ccggcgtttt    660
cttgatatgt ttggtgatgt tgtgatggga attccacacg ccaagtttga agagaagtta    720
gagagaatga aggagaggaa aggagttaaa aatgacactg acttaagcgc ggctgatctc    780
aaggaattgg ttgagcagta caagagtgtt tacttagagg ccaagggtca agagttcct     840 tcagatccaa agaagcaatt ggagctagcg attgaagcgg tattcgattc ttgggatagc    900
ccgagagcga acaagtacag aagtattaac cagataactg gattgaaagg aaccgcggtt    960
aacattcagt gtatggtgtt tggaaacatg ggggacactt cagggactgg tgttctcttc    1020
```

-continued

```
actaggaacc ctagcacagg agagaagaag ctttatggcg agtttctagt taatgctcag    1080
gtttggcatc tatcacaatg tgtgaatctc atatcaacaa ggataagaac accagaagat    1140
ttggatacaa tgaagagatt tatgcctgag gcttacgctg aacttgttga gaactgcaac    1200
atcttagaaa gacattacaa agacatgatg gatattgaat tcacagtaca agaagagaga    1260
ttgtggatgc tgcaatgcag agcgggtaag cgaacgggta aaggcgccgt gaagatagca    1320
gttgatatgg taggtgaagg gcttgttgag aaatcttctg ctatcaaaat ggtgagcct     1380
caacatcttg atcaactact tcacccacag tttcatgatc catcggggta tcgtgaaaaa    1440
gtggtggcca aaggcttacc tgcgtcacca ggagcggcgg ttggacaggt tgtgttcacg    1500
gcggaggaag ccgaagcttg gcattctcag ggtaaaactg tgattctggt tcgaactgag    1560
acaagccctg acgatgtggg aggtatgcac gcagcggaag gtatattgac ggctagagga    1620
ggaatgacgt cacacgcggc tgttgttgct cgcggttggg gaaaatgttg cattgctggt    1680
tgttccgaga ttcgtgtcga cgagaaccac aaggttctat tgattggaga tttgacgatt    1740
aatgaaggcg aatggatctc aatgaacgga tcaaccggtg aggttatatt agggaaacaa    1800
gcattggctc ctccggcttt aagtccagat ttggagactt tcatgtcctg ggctgatgca    1860
atcagacgtc tcaaggttat ggcgaatgcg gatacacctg aagacgccat tgcagctagg    1920
aaaaacggag ctcaaggaat cgggctttgt aggacagagc atatgattgt ttgtatccaa    1980
atgtttaatg ttgtctttgg tttggttttt aagttctttg gagcagatag gattaaagca    2040
gtgagaaaga tgataatggc ggtaacaaca gagcaaagga aagcttctct cgacatcttg    2100
cttccttacc aacgttcgga tttcgaaggg atcttccgtg ctatggatgg tttaccggta    2160
acaatccgtt tgttagaccc tccgcttcac gagtttctcc cggaaggcga cttggacaac    2220
attgtacatg agctagctga agaaactggt gtgaaagaag atgaagtctt gtcacggata    2280
gagaaactct ctgaagtgaa tccaatgctt ggtttccgcg gttgcaggct cggaatatcg    2340
tatccagagc taacggagat gcaagcgcgt gcaattttg aagctgcagc gtcaatgcag    2400
gaccaaggtg ttactgtcat tcctgagatt atggttccac ttgtaggaac tcctcaggaa    2460
ttgggtcacc aagttgatgt aattcgtaaa gttgcaaaga aagtatttgc tgagaagggt    2520
cataccgtga gctacaaggt tgggacaatg attgagatcc ctcgagccgc gctcattgca    2580
gatgagattg cgaaagaggc ggagttttc tcgttcggga caaacgactt gacgcagatg    2640
acgtttggat acagtagaga cgatgtcggc aagtttctac cgatttaccct cgccaaagga    2700
atcttacagc acgaccctt tgaggttctt gatcagcaag gtgtagggca attgatcaag    2760
atggcgacag aaaaaggacg agcagctagg cctagcctca aggttgggat atgtggagaa    2820
catggaggag atccatcttc tgtgggattc tttgctgaag caggacttga ctatgtctct    2880
tgttctcctt tcagggttcc aattgcaagg cttgcagctg ctcaagtagt tgttgcatga    2940
```

<210> SEQ ID NO 23
<211> LENGTH: 898
<212> TYPE: PRT
<213> ORGANISM: Arabidopsis thaliana

<400> SEQUENCE: 23

Met Met Gln Arg Val Phe Thr Phe Gly Lys Gly Arg Ser Glu Gly Asn
1               5                   10                  15

Lys Gly Met Lys Ser Leu Leu Gly Gly Lys Gly Ala Asn Leu Ala Glu
            20                  25                  30

Met Ala Ser Ile Gly Leu Ser Val Pro Pro Gly Leu Thr Ile Ser Thr

```
                 35                  40                  45
Glu Ala Cys Gln Gln Tyr Gln Ile Ala Gly Lys Lys Leu Pro Glu Gly
         50                  55                  60
Leu Trp Glu Glu Ile Leu Glu Gly Leu Ser Phe Ile Glu Arg Asp Ile
 65                  70                  75                  80
Gly Ala Ser Leu Ala Asp Pro Ser Lys Pro Leu Leu Leu Ser Val Arg
                 85                  90                  95
Ser Gly Ala Ala Ile Ser Met Pro Gly Met Met Asp Thr Val Leu Asn
                100                 105                 110
Leu Gly Leu Asn Asp Gln Val Val Gly Leu Ala Ala Lys Ser Gly
            115                 120                 125
Glu Arg Phe Ala Tyr Asp Ser Phe Arg Arg Phe Leu Asp Met Phe Gly
            130                 135                 140
Asp Val Val Met Gly Ile Pro His Ala Lys Phe Glu Glu Lys Leu Glu
145                 150                 155                 160
Arg Met Lys Glu Arg Lys Gly Val Lys Asn Asp Thr Asp Leu Ser Ala
                165                 170                 175
Ala Asp Leu Lys Glu Leu Val Glu Gln Tyr Lys Ser Val Tyr Leu Glu
            180                 185                 190
Ala Lys Gly Gln Glu Phe Pro Ser Asp Pro Lys Lys Gln Leu Glu Leu
            195                 200                 205
Ala Ile Glu Ala Val Phe Asp Ser Trp Asp Ser Pro Arg Ala Asn Lys
    210                 215                 220
Tyr Arg Ser Ile Asn Gln Ile Thr Gly Leu Lys Gly Thr Ala Val Asn
225                 230                 235                 240
Ile Gln Cys Met Val Phe Gly Asn Met Gly Asp Thr Ser Gly Thr Gly
                245                 250                 255
Val Leu Phe Thr Arg Asn Pro Ser Thr Gly Glu Lys Lys Leu Tyr Gly
            260                 265                 270
Glu Phe Leu Val Asn Ala Gln Val Trp His Leu Ser Gln Cys Val Asn
            275                 280                 285
Leu Ile Ser Thr Arg Ile Arg Thr Pro Glu Asp Leu Asp Thr Met Lys
    290                 295                 300
Arg Phe Met Pro Glu Ala Tyr Ala Glu Leu Val Glu Asn Cys Asn Ile
305                 310                 315                 320
Leu Glu Arg His Tyr Lys Asp Met Met Asp Ile Glu Phe Thr Val Gln
                325                 330                 335
Glu Glu Arg Leu Trp Met Leu Gln Cys Arg Ala Gly Lys Arg Thr Gly
            340                 345                 350
Lys Gly Ala Val Lys Ile Ala Val Asp Met Val Gly Glu Gly Leu Val
            355                 360                 365
Glu Lys Ser Ser Ala Ile Lys Met Val Glu Pro Gln His Leu Asp Gln
    370                 375                 380
Leu Leu His Pro Gln Phe His Asp Pro Ser Gly Tyr Arg Glu Lys Val
385                 390                 395                 400
Val Ala Lys Gly Leu Pro Ala Ser Pro Gly Ala Ala Val Gly Gln Val
                405                 410                 415
Val Phe Thr Ala Glu Glu Ala Glu Ala Trp His Ser Gln Gly Lys Thr
            420                 425                 430
Val Ile Leu Val Arg Thr Glu Thr Ser Pro Asp Asp Val Gly Gly Met
            435                 440                 445
His Ala Ala Glu Gly Ile Leu Thr Ala Arg Gly Gly Met Thr Ser His
    450                 455                 460
```

```
Ala Ala Val Val Ala Arg Gly Trp Gly Lys Cys Cys Ile Ala Gly Cys
465                 470                 475                 480

Ser Glu Ile Arg Val Asp Glu Asn His Lys Val Leu Leu Ile Gly Asp
                485                 490                 495

Leu Thr Ile Asn Glu Gly Glu Trp Ile Ser Met Asn Gly Ser Thr Gly
            500                 505                 510

Glu Val Ile Leu Gly Lys Gln Ala Leu Ala Pro Pro Ala Leu Ser Pro
            515                 520                 525

Asp Leu Glu Thr Phe Met Ser Trp Ala Asp Ala Ile Arg Arg Leu Lys
530                 535                 540

Val Met Ala Asn Ala Asp Thr Pro Glu Asp Ala Ile Ala Ala Arg Lys
545                 550                 555                 560

Asn Gly Ala Gln Gly Ile Gly Leu Cys Arg Thr Glu His Met Ile Val
                565                 570                 575

Cys Ile Gln Met Phe Asn Val Val Phe Gly Leu Val Phe Lys Phe Phe
                580                 585                 590

Gly Ala Asp Arg Ile Lys Ala Val Arg Lys Met Ile Met Ala Val Thr
                595                 600                 605

Thr Glu Gln Arg Lys Ala Ser Leu Asp Ile Leu Leu Pro Tyr Gln Arg
610                 615                 620

Ser Asp Phe Glu Gly Ile Phe Arg Ala Met Asp Gly Leu Pro Val Thr
625                 630                 635                 640

Ile Arg Leu Leu Asp Pro Pro Leu His Glu Phe Leu Pro Glu Gly Asp
                645                 650                 655

Leu Asp Asn Ile Val His Glu Leu Ala Glu Glu Thr Gly Val Lys Glu
                660                 665                 670

Asp Glu Val Leu Ser Arg Ile Glu Lys Leu Ser Glu Val Asn Pro Met
                675                 680                 685

Leu Gly Phe Arg Gly Cys Arg Leu Gly Ile Ser Tyr Pro Glu Leu Thr
            690                 695                 700

Glu Met Gln Ala Arg Ala Ile Phe Glu Ala Ala Ser Met Gln Asp
705                 710                 715                 720

Gln Gly Val Thr Val Ile Pro Glu Ile Met Val Pro Leu Val Gly Thr
                725                 730                 735

Pro Gln Glu Leu Gly His Gln Val Asp Val Ile Arg Lys Val Ala Lys
            740                 745                 750

Lys Val Phe Ala Glu Lys Gly His Thr Val Ser Tyr Lys Val Gly Thr
            755                 760                 765

Met Ile Glu Ile Pro Arg Ala Ala Leu Ile Ala Asp Glu Ile Ala Lys
            770                 775                 780

Glu Ala Glu Phe Phe Ser Phe Gly Thr Asn Asp Leu Thr Gln Met Thr
785                 790                 795                 800

Phe Gly Tyr Ser Arg Asp Asp Val Gly Lys Phe Leu Pro Ile Tyr Leu
                805                 810                 815

Ala Lys Gly Ile Leu Gln His Asp Pro Phe Glu Val Leu Asp Gln Gln
            820                 825                 830

Gly Val Gly Gln Leu Ile Lys Met Ala Thr Glu Lys Gly Arg Ala Ala
            835                 840                 845

Arg Pro Ser Leu Lys Val Gly Ile Cys Gly Glu His Gly Gly Asp Pro
850                 855                 860

Ser Ser Val Gly Phe Phe Ala Glu Ala Gly Leu Asp Tyr Val Ser Cys
865                 870                 875                 880
```

```
Ser Pro Phe Arg Val Pro Ile Ala Arg Leu Ala Ala Gln Val Val
                885                 890                 895

Val Ala

<210> SEQ ID NO 24
<211> LENGTH: 979
<212> TYPE: PRT
<213> ORGANISM: Arabidopsis thaliana

<400> SEQUENCE: 24

Met Thr Ser Met Ile Val Lys Thr Thr Pro Glu Leu Phe Lys Gly Asn
1               5                   10                  15

Gly Val Phe Arg Thr Asp His Leu Gly Glu Asn Arg Met Val Ser Arg
            20                  25                  30

Ser Asn Arg Leu Gly Asp Gly Ser Asn Arg Phe Pro Arg Thr Gly Thr
        35                  40                  45

Ile His Cys Gln Arg Leu Ser Ile Ala Lys Thr Gly Leu His Arg Glu
    50                  55                  60

Thr Lys Ala Arg Ala Ile Leu Ser Pro Val Ser Asp Pro Ala Ala Ser
65                  70                  75                  80

Ile Ala Gln Lys Arg Val Phe Thr Phe Gly Lys Gly Arg Ser Glu Gly
                85                  90                  95

Asn Lys Gly Met Lys Ser Leu Leu Gly Gly Lys Gly Ala Asn Leu Ala
            100                 105                 110

Glu Met Ala Ser Ile Gly Leu Ser Val Pro Pro Gly Leu Thr Ile Ser
        115                 120                 125

Thr Glu Ala Cys Gln Gln Tyr Gln Ile Ala Gly Lys Lys Leu Pro Glu
    130                 135                 140

Gly Leu Trp Glu Glu Ile Leu Glu Gly Leu Ser Phe Ile Glu Arg Asp
145                 150                 155                 160

Ile Gly Ala Ser Leu Ala Asp Pro Ser Lys Pro Leu Leu Ser Val
                165                 170                 175

Arg Ser Gly Ala Ala Ile Ser Met Pro Gly Met Met Asp Thr Val Leu
            180                 185                 190

Asn Leu Gly Leu Asn Asp Gln Val Val Gly Leu Ala Ala Lys Ser
        195                 200                 205

Gly Glu Arg Phe Ala Tyr Asp Ser Phe Arg Arg Phe Leu Asp Met Phe
    210                 215                 220

Gly Asp Val Val Met Gly Ile Pro His Ala Lys Phe Glu Glu Lys Leu
225                 230                 235                 240

Glu Arg Met Lys Glu Arg Lys Gly Val Lys Asn Asp Thr Asp Leu Ser
                245                 250                 255

Ala Ala Asp Leu Lys Glu Leu Val Glu Gln Tyr Lys Ser Val Tyr Leu
            260                 265                 270

Glu Ala Lys Gly Gln Glu Phe Pro Ser Asp Pro Lys Lys Gln Leu Glu
        275                 280                 285

Leu Ala Ile Glu Ala Val Phe Asp Ser Trp Asp Ser Pro Arg Ala Asn
    290                 295                 300

Lys Tyr Arg Ser Ile Asn Gln Ile Thr Gly Leu Lys Gly Thr Ala Val
305                 310                 315                 320

Asn Ile Gln Cys Met Val Phe Gly Asn Met Gly Asp Thr Ser Gly Thr
                325                 330                 335

Gly Val Leu Phe Thr Arg Asn Pro Ser Thr Gly Glu Lys Lys Leu Tyr
            340                 345                 350
```

-continued

Gly Glu Phe Leu Val Asn Ala Gln Val Trp His Leu Ser Gln Cys Val
355                 360                 365

Asn Leu Ile Ser Thr Arg Ile Arg Thr Pro Glu Asp Leu Asp Thr Met
370                 375                 380

Lys Arg Phe Met Pro Glu Ala Tyr Ala Glu Leu Val Glu Asn Cys Asn
385                 390                 395                 400

Ile Leu Glu Arg His Tyr Lys Asp Met Met Asp Ile Glu Phe Thr Val
                405                 410                 415

Gln Glu Glu Arg Leu Trp Met Leu Gln Cys Arg Ala Gly Lys Arg Thr
                420                 425                 430

Gly Lys Gly Ala Val Lys Ile Ala Val Asp Met Val Gly Glu Gly Leu
            435                 440                 445

Val Glu Lys Ser Ser Ala Ile Lys Met Val Glu Pro Gln His Leu Asp
        450                 455                 460

Gln Leu Leu His Pro Gln Phe His Asp Pro Ser Gly Tyr Arg Glu Lys
465                 470                 475                 480

Val Val Ala Lys Gly Leu Pro Ala Ser Pro Gly Ala Ala Val Gly Gln
                485                 490                 495

Val Val Phe Thr Ala Glu Glu Ala Glu Ala Trp His Ser Gln Gly Lys
                500                 505                 510

Thr Val Ile Leu Val Arg Thr Glu Thr Ser Pro Asp Asp Val Gly Gly
        515                 520                 525

Met His Ala Ala Glu Gly Ile Leu Thr Ala Arg Gly Gly Met Thr Ser
            530                 535                 540

His Ala Ala Val Val Ala Arg Gly Trp Gly Lys Cys Cys Ile Ala Gly
545                 550                 555                 560

Cys Ser Glu Ile Arg Val Asp Glu Asn His Lys Val Leu Leu Ile Gly
                565                 570                 575

Asp Leu Thr Ile Asn Glu Gly Glu Trp Ile Ser Met Asn Gly Ser Thr
                580                 585                 590

Gly Glu Val Ile Leu Gly Lys Gln Ala Leu Ala Pro Pro Ala Leu Ser
        595                 600                 605

Pro Asp Leu Glu Thr Phe Met Ser Trp Ala Asp Ala Ile Arg Arg Leu
610                 615                 620

Lys Val Met Ala Asn Ala Asp Thr Pro Glu Asp Ala Ile Ala Ala Arg
625                 630                 635                 640

Lys Asn Gly Ala Gln Gly Ile Gly Leu Cys Arg Thr Glu His Met Ile
                645                 650                 655

Val Cys Ile Gln Met Phe Asn Val Phe Gly Leu Val Phe Lys Phe
                660                 665                 670

Phe Gly Ala Asp Arg Ile Lys Ala Val Arg Lys Met Ile Met Ala Val
            675                 680                 685

Thr Thr Glu Gln Arg Lys Ala Ser Leu Asp Ile Leu Leu Pro Tyr Gln
        690                 695                 700

Arg Ser Asp Phe Glu Gly Ile Phe Arg Ala Met Asp Gly Leu Pro Val
705                 710                 715                 720

Thr Ile Arg Leu Leu Asp Pro Pro Leu His Glu Phe Leu Pro Glu Gly
                725                 730                 735

Asp Leu Asp Asn Ile Val His Glu Leu Ala Glu Glu Thr Gly Val Lys
                740                 745                 750

Glu Asp Glu Val Leu Ser Arg Ile Glu Lys Leu Ser Glu Val Asn Pro
        755                 760                 765

Met Leu Gly Phe Arg Gly Cys Arg Leu Gly Ile Ser Tyr Pro Glu Leu

-continued

```
                    770                 775                 780
Thr Glu Met Gln Ala Arg Ala Ile Phe Glu Ala Ala Ser Met Gln
785                 790                 795                 800

Asp Gln Gly Val Thr Val Ile Pro Glu Ile Met Val Pro Leu Val Gly
                805                 810                 815

Thr Pro Gln Glu Leu Gly His Gln Val Asp Val Ile Arg Lys Val Ala
                820                 825                 830

Lys Lys Val Phe Ala Glu Lys Gly His Thr Val Ser Tyr Lys Val Gly
            835                 840                 845

Thr Met Ile Glu Ile Pro Arg Ala Ala Leu Ile Ala Asp Glu Ile Ala
            850                 855                 860

Lys Glu Ala Glu Phe Phe Ser Phe Gly Thr Asn Asp Leu Thr Gln Met
865                 870                 875                 880

Thr Phe Gly Tyr Ser Arg Asp Asp Val Gly Lys Phe Leu Pro Ile Tyr
                885                 890                 895

Leu Ala Lys Gly Ile Leu Gln His Asp Pro Phe Glu Val Leu Asp Gln
                900                 905                 910

Gln Gly Val Gly Gln Leu Ile Lys Met Ala Thr Glu Lys Gly Arg Ala
            915                 920                 925

Ala Arg Pro Ser Leu Lys Val Gly Ile Cys Gly Glu His Gly Gly Asp
930                 935                 940

Pro Ser Ser Val Gly Phe Phe Ala Glu Ala Gly Leu Asp Tyr Val Ser
945                 950                 955                 960

Cys Ser Pro Phe Arg Val Pro Ile Ala Arg Leu Ala Ala Ala Gln Val
                965                 970                 975

Val Val Ala

<210> SEQ ID NO 25
<211> LENGTH: 31
<212> TYPE: DNA
<213> ORGANISM: Artificial Sequence
<220> FEATURE:
<223> OTHER INFORMATION: PCR primer

<400> SEQUENCE: 25
atttctagaa tgtcggccgg taacggaaat g                               31

<210> SEQ ID NO 26
<211> LENGTH: 31
<212> TYPE: DNA
<213> ORGANISM: Artificial Sequence
<220> FEATURE:
<223> OTHER INFORMATION: PCR primer

<400> SEQUENCE: 26
attgagctcc taaaagatag gaccagcagc g                               31

<210> SEQ ID NO 27
<211> LENGTH: 15
<212> TYPE: PRT
<213> ORGANISM: Artificial Sequence
<220> FEATURE:
<223> OTHER INFORMATION: Synthetic peptides designed against PCK amino
      acid sequence

<400> SEQUENCE: 27

Asp Glu His Cys Trp Thr Glu Thr Gly Val Ser Asn Ile Glu Gly
1               5                   10                  15
```

```
<210> SEQ ID NO 28
<211> LENGTH: 15
<212> TYPE: PRT
<213> ORGANISM: Artificial Sequence
<220> FEATURE:
<223> OTHER INFORMATION: Synthetic peptides designed against the PCK
      amino acid sequence

<400> SEQUENCE: 28

Cys Val Asp Leu Ser Arg Glu Lys Glu Pro Asp Ile Trp Asn Ala
1               5                   10                  15

<210> SEQ ID NO 29
<211> LENGTH: 170
<212> TYPE: DNA
<213> ORGANISM: Artificial Sequence
<220> FEATURE:
<223> OTHER INFORMATION: Fragment of plasmid pCR4Blunt-TOPO, nts.
      211-370

<400> SEQUENCE: 29
cacacaggaa acagctatga ccatgattac gccaagctca gaattaaccc tcactaaagg      60
gactagtcct gcaggtttaa acgaattcgc ccttaagggc gaattcgcgg ccgctaaatt     120
caattcgccc tatagtgagt cgtattacaa ttcactggcc gtcgttttac                170

<210> SEQ ID NO 30
<211> LENGTH: 170
<212> TYPE: DNA
<213> ORGANISM: Artificial Sequence
<220> FEATURE:
<223> OTHER INFORMATION: Fragment of plasmid pCR4Blunt-TOPO (nts.
      201-370 ) - complement strand

<400> SEQUENCE: 30
gtaaaacgac ggccagtgaa ttgtaatacg actcactata gggcgaattg aatttagcgg      60
ccgcgaattc gcccttaagg gcgaattcgt ttaaacctgc aggactagtc cctttagtga     120
gggttaattc tgagcttggc gtaatcatgg tcatagctgt ttcctgtgtg                170
```

TRANSGENIC PLANTS COMPRISING CONSTRUCTS ENCODING PHOSPHOENOLPYRUVATE CARBOXYKINASE AND/OR PYRUVATE ORTHOPHOSPHATE DIKINASE

CLAIM FOR PRIORITY

This application is a National Stage Entry entitled to and hereby claims priority under 35 U.S.C. §§365 and 371 to corresponding PCT Application No. PCT/GB2010/050321, filed Feb. 25, 2010, which in turn claims priority to British Application Serial No. GB 0903346.5, filed Feb. 27, 2009. The entire contents of the aforementioned applications are herein expressly incorporated by reference.

STATEMENT REGARDING SEQUENCE LISTING

This application hereby incorporates by reference the sequence listing in the text file named BTMK127_00US_ST25.txt filed herewith having a size of 51 KB. The file was created on May 10, 2013 and is submitted electronically via EFS-Web.

The present invention relates to genetic constructs used in the preparation of transgenic plants. The constructs can have the ability to cause remobilisation of nitrogen during leaf senescence, such that nitrogen can be transported from the leaves to other regions of the plant. The invention extends to plant cells transformed with such constructs, and to the transgenic plants themselves. The invention also relates to methods of producing transgenic plants, and to methods of increasing the rate of nitrogen remobilisation in senescent plants. The invention also relates to harvested plant leaves, for example tobacco leaves, that have been transformed with the genetic constructs, and to smoking articles comprising such harvested plant leaves.

Leaf senescence is a phase of plant development during which the cells undergo distinct metabolic and structural changes prior to cell death. Physiological and genetic studies indicate that senescence is a highly regulated process. The progression of a leaf through senescence is visibly marked by the loss of chlorophyll and consequent yellowing, which results from the disassembly of the chloroplasts. The decreasing levels of leaf chlorophyll, characteristic of this developmental stage, can be measured, e.g. by solvent extraction and spectrophotometric measurement, or by a chlorophyll content meter. A decreased leaf chlorophyll level in comparison with an earlier leaf chlorophyll level recorded for the same plant, preferably grown under constant conditions, indicates senescence.

Molecular studies indicate that senescence is associated with changes in gene expression. The levels of mRNAs encoding proteins involved in photosynthesis decrease during senescence, whilst mRNA levels of genes encoding proteins thought to be involved in the senescence increase. Senescence is a highly organised process regulated by genes known as Senescence Associated Genes (SAGs). Leaf senescence involves the degradation of proteins, nucleic acids and membranes, and the subsequent transport of the nutrients resulting from this degradation to other regions of the plant, such as the developing seeds, leaves or storage organs. One problem of plant senescence is that many useful minerals and nutrients that are present in senescent leaves will remain in the leaves, and will be effectively lost as the leaves die. For example, nitrogen, which can be in the form of amine groups on amino acids, present in the senescent leaves, will go to waste, if it is not removed from dying leaves.

Therefore, increasing nitrogen remobilisation in plants, especially when they become senescent, could have important applications in crop production. Firstly, nitrogen remobilised from leaves can be transported to the younger leaves as well as the developing seed. Increasing the efficiency of nitrogen exit from senescent leaves could therefore potentially increase nitrogen supply to seeds and younger parts of the plant, and thereby increase crop yield and nitrogen use efficiency. This is clearly a valuable goal when the world population is increasing but crop yields are not increasing sufficiently to meet demand. One potential target crop is *Brassica napus* (oilseed rape), which has poor nitrogen efficiency due to poor nitrogen remobilisation from vegetative tissue. Another target crop is wheat, as the potential benefits of increasing grain protein content are great. Grain protein content not only affects nutritive value of wheat, but also determines grain usage and therefore market value. For example, increased grain protein content results in increased bread volume. Also, an ability to increase nitrogen remobilisation could be very useful in the tobacco industry because it is known that residual nitrogen in tobacco leaves contributes to the formation of nitrosamines.

The enzymes phosphoenolpyruvate carboxykinase (PEPCK, or PCK) [EC 4.1.1.49] and pyruvate orthophosphate dikinase (PPDK) [EC 2.7.9.1] are known. PPDK is present in both prokaryotes and eukaryotes, and is conserved in terms of sequence and tertiary structure between bacteria and higher plants (Pocalyko et al., 1990, Biochemistry, 29, 10757-10765). The enzyme catalyses the reversible phosphorylation of pyruvate to form phosphoenolpyruvate (PEP) (Carroll et al., 1990, Federation of European Biochemical Societies, 274, 178-180; Hatch & Slack, 1968, Biochemical Journal, 106, 141-146), in the following reaction: Pyruvate+Pi+ATP=PEP+PPi+AMP. In both C3 and C4 plants, the PPDK gene has an unusual structure, with two transcripts resulting from the same gene. The longer transcript encodes a chloroplastic protein, with the first exon encoding a chloroplast transit peptide, while the shorter transcript is transcribed from a separate promoter within the first intron of the longer transcript, and therefore lacks the first exon encoding the chloroplast transit peptide. This shorter transcript generates a cytosolic isoform of PPDK. This gene structure has been reported in maize, rice, C3 and C4 *Flaveria* species, and *Arabidopsis thaliana*.

Phosphoenolpyruvate carboxykinase (PCK) catalyses a reversible reaction between ADP, carbon dioxide and phosphoenolpyruvate to form ATP and oxaloacetate, in the following reaction: oxaloacetate+ATP=PEP+ADP+$CO_2$. PCK has been shown to be present in the cytosol of cells of a wide range of plant tissues. These include developing seeds, trichomes and roots. In plants, PCK appears in tissues in which there is increased metabolism of nitrogenous compounds.

The inventors constructed a number of genetic constructs, in which genes encoding the enzymes PCK and/or PPDK were placed either alone or together under the control of a promoter, to determine what effect, if any, over-expression of these genes had on nitrogen remobilisation in senescent leaves.

According to a first aspect of the invention, there is provided a genetic construct comprising a senescence-specific promoter operably linked to at least one coding sequence, which encodes at least one polypeptide having phosphoenolpyruvate carboxykinase (PCK) activity and/or pyruvate orthophosphate dikinase (PPDK) activity.

According to a second aspect of the invention, there is provided a genetic construct comprising a promoter operably linked to at least one coding sequence, which encodes at least one polypeptide having phosphoenolpyruvate carboxykinase (PCK) activity and pyruvate orthophosphate dikinase (PPDK) activity.

The inventors believed that the two enzymes PCK and PPDK may play a role in the interconversion of various amino acids during remobilisation of nitrogen from leaves during senescence. Although the inventors do not wish to be bound by hypothesis, a speculative biochemical pathway illustrating how PCK and PPDK may affect Nitrogen remobilisation is illustrated in FIG. 18. They therefore considered that stimulating over-expression of these two enzymes in a plant, either independently or simultaneously, during senescence could play a role in the remobilisation of nitrogen.

As a result of their studies, the inventors surprisingly found that constructs according to the invention, encoding PCK and/or PPDK, resulted in increased rates of nitrogen remobilisation from senescent leaves. The inventors hypothesise that nitrogen may be being moved from senescent leaves in the form of amino acids to the younger parts of the plant, such as the plant seeds. Furthermore, the inventors also observed an increase in the amount of vegetative plant growth (which corresponds to an increase in crop yield), when these enzymes were over-expressed in senescent leaves. The inventors believe therefore that constructs according to the invention will be useful in the preparation of a transgenic plant, which may be able to exhibit increased rates of nitrogen remobilisation from senescent leaves and/or an increased growth rate.

The promoter in the genetic constructs of the first or second aspect may be capable of inducing RNA polymerase to bind to, and start transcribing, the at least one coding region encoding the at least one polypeptide having PCK and/or PPDK activity.

The promoter present in the construct of the second aspect may be constitutive, non-constitutive, or tissue-specific. Examples of suitable promoters include the cauliflower mosaic virus 35S promoter (full or truncated), the rubisco promoter, the pea plastocyanin promoter, the nopaline synthase promoter, the chlorophyll r/b binding promoter, the high molecular weight glutenin promoter, the α, β-gliadin promoter, the hordein promoter or the patatin promoter.

The promoter present in the construct of the second aspect may be a senescence-specific promoter.

A "senescence-specific promoter" (SAG) can be a promoter, which is associated with controlling the expression of a senescence-associated gene. Hence, the promoter can restrict expression of a coding sequence (i.e. a gene) to which it is operably linked substantially exclusively in senescing tissue. Therefore, a senescence-specific promoter can be a promoter capable of preferentially promoting gene expression in a plant tissue in a developmentally-regulated manner such that expression of a 3' protein-coding region occurs substantially only when the plant tissue is undergoing senescence. It will be appreciated that senescence tends to occur in the older parts of the plant, such as the older leaves, and not in the younger parts of the plants, such as the seeds.

One example of a plant which is known to express numerous senescence-associated genes is *Arabidopsis*. Hence, the promoter in a construct according to the first or second aspect may be isolated from a senescence-associated gene in *Arabidopsis*. Gepstein et al. (The Plant Journal, 2003, 36, 629-642) conducted a detailed study of SAGs and their promoters using *Arabidopsis* as a model. The genetic construct may comprise a promoter from any of the SAGs disclosed in this paper. For example, a suitable promoter may be selected from a group consisting of SAG12, SAG13, SAG101, SAG21 and SAG18, or a functional variant or a functional fragment thereof.

Preferred promoters are SAG12 and SAG13 promoters. In one embodiment, the promoter is a SAG12 promoter, which will be known to the skilled technician, or a functional variant or a fragment thereof (Gan & Amasino, 1997, Plant Physiology, 113: 313-319). The DNA sequence encoding the SAG12 promoter is referred to herein as SEQ ID No.16, as follows:

SEQ ID NO: 16
TCGAGACCCGATTGTTATTTTTAGACTGAGACAAAAAAGTAGAATCGTTG

ATTGTTAAAATTTAAAATTAGTTTCATTACGTTTCGATAAAAAAATGATT

AGTTTATCATAGCTTAATTATAGCATTGATTTCTAAATTTGTTTTTTGAC

CACCCTTTTTTCTCTCTTTGGTGTTTTCTTAACATTAGAAGAACCCATAA

CAATGTACGTTCAAATTAATTAAAAACAATATTTCCAAGTTTTATATACG

AAACTTGTTTTTTTTAATGAAAACAGTTGAATAGTTGATTATGAATTAGT

TAGATCAATACTCAATATATGATCAATGATGTATATATATGAACTCAGTT

GTTATACAAGAAATGAAAATGCTATTTAAATACAGATCATGAAGTGTTAA

AAAGTGTCAGAATATGACATGAAGCGTTTTGTCCTACCGGGTATTCGAGT

TATAGGTTTGGATCTCTCAAGAATATTTTGGGCCATACTAGTTATATTTG

GGCTTAAGCGTTTTGCAAAGAGACGAGGAAGAAAGATTGGGTCAAGTTAA

CAAAACAGAGACACTCGTATTAGTTGGTACTTTGGTAGCAAGTCGATTTA

TTTGCCAGTAAAAACTTGGTACACAACTGACAACTCGTATCGTTATTAGT

TTGTACTTGGTACCTTTGGTTCAAGAAAAAGTTGATATAGTTAAATCAGT

TGTGTTCATGAGGTGATTGTGATTTAATTTGTTGACTAGGGCGATTCCTT

CACATCACAATAACAAAGTTTTATAGATTTTTTTTTTATAACATTTTTGC

CACGCTTCGTAAAGTTTGGTATTTACACCGCATTTTTCCCTGTACAAGAA

TTCATATATTATTTATTTATATACTCCAGTTGACAATTATAAGTTTATAA

CGTTTTTACAATTATTTAAATACCATGTGAAGATCCAAGAATATGTCTTA

CTTCTTCTTTGTGTAAGAAAACTAACTATATCACTATAATAAAATAATTC

TAATCATTATATTTGTAAATATGCAGTTATTTGTCAATTTTGAATTTAGT

ATTTTAGACGTTATCACTTCAGCCAAATATGATTTGGATTTAAGTCCAAA

ATGCAATTTCGTACGTATCCCTCTTGTCGTCTAATGATTATTTCAATATT

TCTTATATTATCCCTAACTACAGAGCTACATTTATATTGTATTCTAATGA

CAGGGAAACCTTCATAGAGATTCAGATAGATGAAATTGGTGGGAAACATC

ATTGAACAGGAAACTTTTAGCAAATCATATCGATTTATCTACAAAAGAAT

ACGTAGCGTAATGAAGTCCACTTGTTGTGAATGACTATGATTTGATCAAA

TTAGTTAATTTTGTCGAATCATTTTTCTTTTTGATTTGATTAAGCTTTTA

ACTTGCACGAATGGTTCTCTTGTGAATAAACAGAATCTTTGAATTCAAAC

TATTTGATTAGTGAAAAGACAAAAGAAGATTCCTTGTTTTTATGTGATTA

GTGATTTTGATGCATGAAAGGTACCTACGTACTACAAGAAAAATAAACAT

GTACGTAACTACGTATCAGCATGTAAAAGTATTTTTTTCCAAATAATTTA

TACTCATGATAGATTTTTTTTTTTGAAATGTCAATTAAAAATGCTTTCT

TAAATATTAATTTTAATTAATTAAATAAGGAAATATATTTATGCAAAACA

-continued

```
TCATCAACACATATCCAACTTCGAAAATCTCTATAGTACACAAGTAGAGA

AATTAAATTTTACTAGATACAAACTTCCTAATCATCAAATATAAATGTTT

ACAAAACTAATTAAACCCACCACTAAAATTAACTAAAAATCCGAGCAAAG

TGAGTGAACAAGACTTGATTTCAGGTTGATGTAGGACTAAAATGACTACG

TATCAAACATCAACGATCATTTAGTTATGTATGAATGAATGTAGTCATTA

CTTGTAAAACAAAAATGCTTTGATTTGGATCAATCACTTCATGTGAACAT

TAGCAATTACATCAACCTTATTTTCACTATAAAACCCCATCTCAGTACCC

TTCTGAAGTAATCAAATTAAGAGCAAAAGTCATTTAACTTAGG
```

Therefore, the promoter in the construct of the invention may comprise a nucleotide sequence substantially as set out in SEQ ID No.16, or a functional variant or functional fragment thereof. The SAG12 promoter sequence may be obtained from *Arabidopsis thaliana*, as described in U.S. Pat. No. 5,689,042. This promoter sequence can be seen in each of the genetic constructs in accordance with the invention, as shown in FIG. 3. In embodiments where the promoter is SAG12, it will be appreciated that the promoter may comprise each of the bases 1-2093 of SEQ ID No:16. However, functional variants or functional fragments of the promoter may also be used in the genetic constructs of the invention.

A "functional variant or functional fragment of a promoter" can be a derivative or a portion of the promoter that is functionally sufficient to initiate expression of any coding region that is operably linked thereto. For example, in embodiments where the promoter is based on SAG12, the skilled technician will appreciate that SEQ ID No:16 may be modified, or that only portions of the SAG12 promoter may be required, such that it would still initiate gene expression in the construct.

Functional variants and functional fragments of the promoter may be readily identified by assessing whether or not transcriptase will bind to a putative promoter region, and then lead to the transcription of the coding region into the polypeptide having PCK and/or PPDK activity. Alternatively, such functional variants and fragments may be examined by conducting mutagenesis on the promoter, when associated with a coding region, and assessing whether or not gene expression may occur.

The genetic construct of the first aspect may be capable of causing, during senescence, expression of at least one polypeptide exhibiting PCK activity and/or PPDK activity. Therefore, the genetic construct may comprise at least one coding sequence, which encodes (i) a phosphoenolpyruvate carboxykinase (PCK), or a functional variant or fragment thereof, and/or (ii) a pyruvate orthophosphate dikinase (PPDK), or a functional variant or fragment thereof. As described in the Examples, the inventors have developed a range of genetic constructs based on polypeptides having either PCK and/or PPDK activities, and these are shown in FIG. 3.

In a first embodiment of the genetic construct according to the first aspect, the promoter may induce expression of a coding sequence encoding a polypeptide exhibiting PCK activity. This is referred to herein as a "PCK construct", and is shown in FIG. 3. Hence, in the first embodiment, the genetic construct may comprise the senescence-specific promoter and a coding sequence encoding a phosphoenolpyruvate carboxykinase (PCK), or a functional variant or fragment thereof. The genetic construct may not encode a polypeptide having PPDK activity.

In a second embodiment of the construct according to the first aspect, the promoter may induce expression of a coding sequence encoding a polypeptide exhibiting PPDK activity. This is referred to herein as a "PPDK construct", and is shown in FIG. 3. In the second embodiment, the genetic construct may comprise the senescence-specific promoter and a coding sequence encoding a pyruvate orthophosphate dikinase (PPDK), or a functional variant or fragment thereof. The genetic construct may not encode a polypeptide having PCK activity.

In a third embodiment of the construct according to the first aspect, the promoter may induce expression of a single coding sequence encoding a polypeptide exhibiting both PCK activity and PPDK activity. This is referred to as a "PCK/PPDK construct 1". In the third embodiment, the genetic construct may comprise the senescence-specific promoter and a coding sequence encoding (i) phosphoenolpyruvate carboxykinase (PCK), or a functional variant or fragment thereof, and (ii) pyruvate orthophosphate dikinase (PPDK), or a functional variant or fragment thereof. The construct of the third embodiment may encode a single transcript exhibiting dual activity, i.e. both PCK and PPDK enzymatic activity. The PCK-coding region may be positioned on the 3' side of the PPDK-coding region. However, preferably the PCK-coding region is positioned on the 5' side of the PPDK-coding region.

In a fourth embodiment of the construct according to the first aspect, the promoter may induce expression of (i) a first coding sequence encoding a first polypeptide, which exhibits PCK activity, and (ii) a second coding sequence encoding a second polypeptide, which exhibits PPDK activity. This is referred to as a "PCK/PPDK construct 2". Hence, in the fourth embodiment, the genetic construct may comprise at least one senescence-specific promoter and (i) a first coding sequence encoding PCK, or a functional variant of fragment thereof, and (ii) a second coding sequence encoding PPDK, or a functional variant or fragment thereof, i.e. two transcripts are encoded, one for each enzyme.

As described in Example 6, the inventors have found that over-expressing either PCK or PPDK in a host cell (e.g. by transforming with either the "PCK construct" or the "PPDK construct") caused an increase in nitrogen remobilisation in senescent leaves. Furthermore, they found that the PCK and PPDK single constructs resulted in an increase in vegetative growth.

As described in Example 8, the inventors have found that simultaneously over-expressing both PCK and PPDK in a host cell (e.g. by transforming with both the "PCK construct" and the "PPDK construct") is surprisingly effective at inducing nitrogen remobilisation in senescent leaves. Hence, nitrogen may be transported out of senescent leaves, for example as transport amino acids. Suitable transport amino acids may be glutamine and/or asparagine. Furthermore, simultaneously over-expressing PCK and PPDK during senescence may also increase growth rate, which may result in an increase in vegetative growth. Hence, the construct of the first aspect may comprise a coding sequence which encodes both PCK and PPDK, or a functional variant or fragment thereof.

It will be appreciated that the construct of the second aspect comprises a coding sequence which encodes both PCK and PPDK, or a functional variant or fragment thereof. The two enzymes may be encoded as a single polypeptide having dual activity, or as two polypeptides, one having PCK activity and the other having PPDK activity.

The phosphoenolpyruvate carboxykinase (PCK) or a functional variant or fragment thereof, and the pyruvate orthophosphate dikinase (PPDK) or a functional variant or fragment thereof, may each be derived from any suitable source, such as a plant. The coding sequence of each enzyme may be derived from a suitable plant source, for example from *Arabidopsis*. Therefore, the coding sequence, which encodes the polypeptide having PCK activity, may be derived from *Arabidopsis*. Furthermore, the coding sequence, which encodes the polypeptide having PPDK activity, may be derived from *Arabidopsis* spp., *Zea* spp., *Flaveria* spp., or *Cleome* spp. The coding sequence, which encodes the polypeptide having PPDK activity, may be derived from *Arabidopsis thaliana, Zea mays, Flaveria trinervia, Flaveria bidentis, Flaveria brownie* or *Cleome gynandra*.

There are believed to be three genes in *A. thaliana* coding for PCK. The genomic DNA sequence (including introns and exons) encoding one embodiment of *Arabidopsis* phosphoenolpyruvate carboxykinase (PCK) is provided herein as SEQ ID No:17, as follows:

```
                                                  SEQ ID No: 17
ATGTCGGCCGGTAACGGAAATGCTACTAACGGTGACGGAGGGTTTAGTTT
CCCTAAAGGACCGGTGATGCCGAAGATAACGACCGGAGCAGCAAAGAGAG
GTAGCGGAGTCTGCCACGACGATAGTGGTCCGACGGTGAATGCCACAACC
ATCGATGAGCTTCATTCGTTACAGAAGAAACGTTCTGCTCCTACCACACC
GATCAACCAAAACGCCGCCGCTGCTTTTGCCGCCGTCTCCGAGGAGGAGC
GTCAGAAGATTCAGCTTCAATCTATCAGGTCCTTATAATAACTTCACATA
TACAGATTATTCATACGTTACTTTTGTTTATAACATACTTTATATCGAAT
TAAGGAAGATTATTGCGTTTTCGTGTCCGATCATTTTCATGGAAAAGTG
TCTTTTAGCTAAATATATGGTGTAGTATTAAATATTTCTGACGTGATATA
CACTAAACTTGAAAATTTTCAATTACTATTTCTTCCTTTAATTCGGCAAT
ATAATTTGTTTTGTTTATTTTTGGATTAGACATTTATGGACAAGTTAAT
GCGCTATTGTGACTATTACCAGAAAATAATACTTTAATGTACATGACACG
TGTTTAAAACGACACGTGGAAACTAATTTTGATTAATTGTGAAACAGTGC
ATCGTTAGCATCGTTAACGAGAGAGTCAGGACCAAAGGTGGTGAGAGGAG
ATCCGGCGGAGAAGAAGACCGATGGTTCAACTACTCCGGCGTACGCTCAC
GGCCAACATCATTCTATCTTTTCTCCGGCTACTGGTGCTGTCAGTGATAG
CTCCTTGAAGTTTACTCACGTCCTCTACAATCTTTCGCCTGCAGGTCAAC
AAATAAACCTAGAATCCGAATCTGAATATTGATAAATGTTTCTGCAACGA
GTTTGATAGATTGGTTTGTGATTTTGTTGTTTGTAGAGCTTTATGAGCA
AGCTATTAAGTATGAGAAAGGTTCGTTTATCACTTCTAATGGAGCTTTGG
CGACGCTTTCTGGTGCTAAGACTGGTCGTGCTCCCAGAGATAAGCGTGTT
GTTAGAGATGCTACTACTGAGGATGAGCTTTGGTGGGGAAAGTGAGTATT
CCTAATCTCGATTTTGATTGATGGAGTTTTTGGGTTTATGCTCTGTTTTC
GTTTATTGATTTTGGAGTTTGATTTTGATTTTAGGGGTTCGCCGAATATC
GAAATGGATGAACATACTTTCATGGTGAACAGAGAAAGAGCTGTTGATTA
CTTGAATTCCTTGGAAAAGGTATTAAATTTTGAAAACTTTAATCAATGTT
GTTGAGTGTAGAACTTTTGATCTAAGTTTATGAAATTTCTGTTGTTGTTG
GGGTTTTTAGGTCTTTGTCAATGACCAATACTTAAACTGGGATCCAGAGA
ACAGAATCAAAGTCAGGATTGTCTCAGCTAGAGCTTACCATTCATTGTTT
ATGCACAACATGTAAGTAAAATCATTATTGACTCCTTGTATGTCAATCCA
TTATTGTGGGTGAAAGAAAACAACAAATTAGTAACTGGGGAGGGTGTCAG
GTGTATCCGACCAACTCAGGAGGAGCTTGAGAGCTTTGGTACTCCGGATT
TTACTATATACAATGCTGGGCAGTTTCCATGTAATCGTTACACTCATTAC
ATGACTTCGTCCACTAGCGTAGACCTTAATCTGGCTAGGAGGGAAATGGT
TATACTTGGTACTCAGTATGCTGGGGAAATGAAGAAGGGTCTTTTCAGTG
TGATGCATTACCTTATGCCTAAGCGTCGTATTCTCTCCCTTCATTCTGGA
TGCAATATGGGAAAAGATGGAGATGTTGCTCTCTTCTTTGGACTTTCAGG
TATAGTAGAGACAGTACCAACTATGGTGTTGGGTGATGATGGAAGGAACG
ATAAATCAAATGATACAATACAATTACTGCTGAACTGACTTGAGAACTGC
TTGCCTCTTTGTTGAGTTTAGCGGGTGAATTGAGATTGATGATTGTGTTT
TTTGTTTTCTATGAATGATGATTTTAGGTACCGGGAAGACAACGCTGTCT
ACTGATCACAACAGGTATCTTATTGGAGATGATGAGCATTGTTGGACTGA
GACTGGTGTTTCGAACATTGAGGGTGGGTGCTATGCTAAGTGTGTTGATC
TTTCGAGGGAGAAGGAGCCTGATATCTGGAACGCTATCAAGTTTGGAACA
GGTAGAAAGACAGTACGTTGGAATTGTTTTTGAGAAAAAAACATAAAGCA
GTGATATAACAATAAGATTCTGATCTTGTTGCAGTTTTGGAAAATGTTGT
GTTTGATGAGCACACCAGAGAAGTGGATTACTCTGATAAATCTGTTACAG
GTAAAACAATTGTTATTTCTTTCATTCTCTTCGTCCTCACAATTAACAGA
ATGATCATTTTCGATTCTCTTTGGTTGCAGAGAACACACGTGCTGCCTAC
CCAATTGAGTTCATTCCAAATGCGAAAATACCTTGTGTTGGTCCACACCC
GACAAATGTGATACTTCTGGCTTGTGATGCCTTTGGTGTTCTCCCACCTG
TGAGCAAGCTGAATCTGGCACAAACCATGTACCACTTCATCAGTGGTTAC
ACTGCTCTGGTAAGGCCAAAGTAAAAGTCTTTATTTTGCACATCGTCTTC
ATAAATTTCAAAAGCATAACCAAAGATGTGCAACATATATAGGTTGCTGG
CACAGAGGATGGTATCAAGGAGCCAACAGCAACATTCTCAGCTTGCTTTG
GTGCAGCTTTCATAATGTTGCATCCCACAAAGTATGCAGCTATGTTAGCT
GAGAAGATGAAGTCACAAGGTGCTACTGGTTGGCTCGTCAACACTGGTTG
GTCTGGTGGCAGGTATATATGTCCTTCTATGGAAATCGATACAACAAAAC
GCTGCCTTGTAACACATGTTTGTAGGCTATTAACATGATCTGTAATGTTT
TATTTCCTGCAGTTATGGTGTTGGAAACAGAATCAAGCTGGCATACACTA
GAAAGATCATCGATGCAATCCATTCGGGCAGTCTCTTGAAGGCAAACTAC
AAGAAAACCGAAATCTTTGGATTTGAAATCCCAACTGAGATCGAAGGGAT
ACCTTCAGAGATCTTGGACCCCGTCAACTCCGTAAGTTTCTGCAAATCTG
TATAATGTAATTGCTTAAGTGATGATGAACAATTTTTTGTTGATTTGGGT
TTAATGAAAATGCAGTGGTCTGATAAGAAGGCACACAAAGATACTCTGGT
GAAACTGGGAGGTCTGTTCAAGAAGAACTTCGAGGTTTTGCTAACCATA
AGATTGGTGTGATGGTAAGCTTACGGAGGAGATTCTCGCTGCTGGTCCTA
TCTTTTAG
```

The cDNA sequence (exons only) encoding the *Arabidopsis* phosphoenolpyruvate carboxykinase (PCK) is provided herein as SEQ ID No:18, as follows:

SEQ ID No: 18

```
ATGTCGGCCGGTAACGGAAATGCTACTAACGGTGACGGAGGGTTTAGTTT
CCCTAAAGGACCGGTGATGCCGAAGATAACGACCGGAGCAGCAAAGAGAG
GTAGCGGAGTCTGCCACGACGATAGTGGTCCGACGGTGAATGCCACAACC
ATCGATGAGCTTCATTCGTTACAGAAGAAACGTTCTGCTCCTACCACACC
GATCAACCAAAACGCCGCCGCTGCTTTTGCCGCCGTCTCCGAGGAGGAGC
GTCAGAAGATTCAGCTTCAATCTATCAGTGCATCGTTAGCATCGTTAACG
AGAGAGTCAGGACCAAAGGTGGTGAGAGGAGATCCGGCGGAGAAGAAGAC
CGATGGTTCAACTACTCCGGCGTACGCTCACGGCCAACATCATTCTATCT
TTTCTCCGGCTACTGGTGCTGTCAGTGATAGCTCCTTGAAGTTTACTCAC
GTCCTCTACAATCTTTCGCCTGCAGAGCTTTATGAGCAAGCTATTAAGTA
TGAGAAAGGTTCGTTTATCACTTCTAATGGAGCTTTGGCGACGCTTTCTG
GTGCTAAGACTGGTCGTGCTCCCAGAGATAAGCGTGTTGTTAGAGATGCT
ACTACTGAGGATGAGCTTTGGTGGGGAAAGGGTTCGCCGAATATCGAAAT
GGATGAACATACTTTCATGGTGAACAGAGAAAGAGCTGTTGATTACTTGA
ATTCCTTGGAAAAGGTCTTTGTCAATGACCAATACTTAAACTGGGATCCA
GAGAACAGAATCAAAGTCAGGATTGTCTCAGCTAGAGCTTACCATTCATT
GTTTATGCACAACATGTGTATCCGACCAACTCAGGAGGAGCTTGAGAGCT
TTGGTACTCCGGATTTTACTATATACAATGCTGGGCAGTTTCCATGTAAT
CGTTACACTCATTACATGACTTCGTCCACTAGCGTAGACCTTAATCTGGC
TAGGAGGGAAATGGTTATACTTGGTACTCAGTATGCTGGGGAAATGAAGA
AGGGTCTTTTCAGTGTGATGCATTACCTTATGCCTAAGCGTCGTATTCTC
TCCCTTCATTCTGGATGCAATATGGGAAAAGATGGAGATGTTGCTCTCTT
CTTTGGACTTTCAGGTACCGGGAAGACAACGCTGTCTACTGATCACAACA
GGTATCTTATTGGAGATGATGAGCATTGTTGGACTGAGACTGGTGTTTCG
AACATTGAGGGTGGGTGCTATGCTAAGTGTGTTGATCTTTCGAGGGAGAA
GGAGCCTGATATCTGGAACGCTATCAAGTTTGGAACAGTTTTGGAAAATG
TTGTGTTTGATGAGCACACCAGAGAAGTGGATTACTCTGATAAATCTGTT
ACAGAGAACACACGTGCTGCCTACCCAATTGAGTTCATTCCAAATGCGAA
AATACCTTGTGTTGGTCCACACCCGACAAATGTGATACTTCTGGCTTGTG
ATGCCTTTGGTGTTCTCCCACCTGTGAGCAAGCTGAATCTGGCACAAACC
ATGTACCACTTCATCAGTGGTTACACTGCTCTGGTTGCTGGCACAGAGGA
TGGTATCAAGGAGCCAACAGCAACATTCTCAGCTTGCTTTGGTGCAGCTT
TCATAATGTTGCATCCCACAAAGTATGCAGCTATGTTAGCTGAGAAGATG
AAGTCACAAGGTGCTACTGGTTGGCTCGTCAACACTGGTTGGTCTGGTGG
CAGTTATGGTGTTGGAAACAGAATCAAGCTGGCATACACTAGAAAGATCA
TCGATGCAATCCATTCGGGCAGTCTCTTGAAGGCAAACTACAAGAAAACC
GAAATCTTTGGATTTGAAATCCCAACTGAGATCGAAGGGATACCTTCAGA
GATCTTGGACCCCGTCAACTCCTGGTCTGATAAGAAGGCACACAAAGATA
CTCTGGTGAAACTGGGAGGTCTGTTCAAGAAGAACTTCGAGGTTTTTGCT
AACCATAAGATTGGTGTGATGGTAAGCTTACGGAGGAGATTCTCGCTGCT
GGTCCTATCTTTTAG
```

Accordingly, the coding sequence, which encodes the polypeptide having PCK activity, may comprise a nucleic acid sequence substantially as set out in SEQ ID No:17 or SEQ ID No.18, or a functional variant or fragment thereof.

The polypeptide sequence of *Arabidopsis* PCK is provided herein as SEQ ID No:19, follows:

SEQ ID No: 19

```
MSAGNGNATNGDGGFSFPKGPVMPKITTGAAKRGSGVCHDDSGPTVNATT
IDELHSLQKKRSAPTTPINQNAAAAFAAVSEEERQKIQLQSISASLASLT
RESGPKVVRGDPAEKKTDGSTTPAYAHGQHHSIFSPATGAVSDSSLKFTH
VLYNLSPAELYEQAIKYEKGSFITSNGALATLSGAKTGRAPRDKRVVRDA
TTEDELWWGKGSPNIEMDEHTFMVNRERAVDYLNSLEKVFVNDQYLNWDP
ENRIKVRIVSARAYHSLFMHNMCIRPTQEELESFGTPDFTIYNAGQFPCN
RYTHYMTSSTSVDLNLARREMVILGTQYAGEMKKGLFSVMHYLMPKRRIL
SLHSGCNMGKDGDVALFFGLSGTGKTTLSTDHNRYLIGDDEHCWTETGVS
NIEGGCYAKCVDLSREKEPDIWNAIKFGTVLENVVFDEHTREVDYSDKSV
TENTRAAYPIEFIPNAKIPCVGPHPTNVILLACDAFGVLPPVSKLNLAQT
MYHFISGYTALVAGTEDGIKEPTATFSACFGAAFIMLHPTKYAAMLAEKM
KSQGATGWLVNTGWSGGSYGVGNRIKLAYTRKIIDAIHSGSLLKANYKKT
EIFGFEIPTEIEGIPSEILDPVNSWSDKKAHKDTLVKLGGLFKKNFEVFA
NHKIGVMVSLRRRFSLLVLSF
```

Accordingly, the polypeptide having PCK activity may comprise an amino acid sequence substantially as set out in SEQ ID No:19, or a functional variant or fragment thereof.

*Arabidopsis* is believed to have at least two forms of PPDK, a chloroplastic form and a cytosolic form, both of which are encoded by the same gene with minor splicing variations at the 5' end of the gene giving rise to the two forms. The genomic DNA sequence (including introns and exons) encoding both forms of *Arabidopsis* pyruvate orthophosphate dikinase (PPDK) is provided herein as SEQ ID No:20, as follows:

SEQ ID No: 20

```
ATGACAAGTATGATCGTGAAGACAACGCCGGAGCTCTTCAAAGGAAATGG
AGTGTTCCGTACGGATCATCTCGGAGAAAACCGAATGGTTAGTCGATCAA
ACCGGCTAGGTGATGGATCAAACCGTTTCCCTAGAACCGGTACAATCCAT
TGCCAACGGTTAAGCATAGCAAAGACCGGTTTGCATCGTGAGACGAAGGC
TCGAGCCATACTTAGCCCTGTGTCCGATCCGGCCGCTTCCATAGCCCAAA
AGGTAAGCCTTTCCATTTCAATCATTCTGGTGTATTTTCACCATAAAATT
TTATACACTTTTTTATTACGTTTTGTTTTATGATTCTGACGTGAGATTCT
TGAGAGAAACTATCACCGATCATTGGGTCGAACCATCTAGCAGCTCAATT
ATTATCGGTTATAACCCTACCGGTTATAGAATACAAAACAGGTTACGCCA
TTGTGACATTTGCTTTGTGATCTTGTGAGACGATTAATTATTTGATGTTG
ATTGGTTTCGTTACTCTTGTTTAAACAATCGAACGGTTCAAACTAATACA
```

-continued

```
CACATGTGATGTGAGATCATTTCGGTAGTAATACCAAATAGCGTCTGGCC
TAAATTATGAAAGTACTATTTTGAATTAAATTATTGTGGAAACATGAACT
TATTTAAATTCAAGTATTTTCGAAATTTGTAATAAAAAAAAACTTTTCCT
CTAGATTCATTAGCCCTACTTTTCGTAGAAACAACTTTAATGTATTCAAA
GACCACTTTGCTGCTTAAGTCAGACTCTTGTGCCACTTGGTAGATCCACC
AATGCCACGTTTTGTTATTGTGCCAAAGAATACGTGAATATGTCCAAACG
GCAATCAAATTCTTGGCGTAAAACACAAAAATTATGATACTAGTTTAAAT
CCACAATTCACCTTCACCATAAAGAATTCATGTATTAGAGATGGTATGAC
AAGAACTGGTTGAATTTGATGACATTTGTTTGCTATTGTTTTGGTTAAGT
AAAAGTTTTGTTAAAAGGAAAATAGCATCGGTAGTGGCAGATAGCAAGT
GTGTGAGTGAGATCAGATATGGTTGACACATCTATGACGAGTCATCGCAA
CGAAACTTCTTTAATTTTGGTCAATTATATTACAATTTAGCATTTCGAGG
TTGGAATTTTGGAATGATCTCTTGATAAGATAATAATGTATTTTTGATGA
CGTATCCATCAAAACTATAAATGATTTATATTAAATATGAAATTTCGACT
GTATACAAGTTTTTATATTATAAAATTATTCGATGTACATATGATCATAA
TAACTTTACTATATATAGATACGTATATGTGTTCTTAAACTTGCACAA
ACATTTCTGCAATCTAAACCTCAATCAAAACAAACAAACAAAAAACCATG
ATGCAGCGAGTATTCACCTTTGGAAAAGGAAGAAGCGAAGGCAACAAGGG
CATGAAGTCCTTGGTATGTTACCAATACCATCATCATGATCATATCAATT
CATTAATAATTTAGTGTTTGCTATTTTCAAGAACCATTTATCAAAAATGT
TAATTGTTGTTGTGTATGAAGTTGGGAGGGAAAGGAGCCAACCTGGCGGA
GATGGCTAGCATAGGCTTGTCGGTGCCGCCGGGGCTAACCATATCGACGG
AGGCTTGTCAGCAGTATCAGATCGCCGGCAAAAAGCTTCCAGAAGGTTTA
TGGGAAGAGATCTTAGAAGGTCTTAGCTTCATCGAACGTGACATTGGAGC
TTCCCTCGCTGATCCCTCCAAGCCACTCCTCCTCTCTGTTCGCTCCGGCG
CCGCCGTAAGTTAATTATAACTTTTTTTCTTGACTATTTTTATTTTAAGG
ATTTTTTCTAATGTTAAATTTCTGTTTTTTTTCTTTCTATGTTTTCTTT
AATCTTTTGAAGATTTTTTGACGCAGATTTTGACTTGTTAGATTTCTTTT
ATTGAAGTTGAGATCCAAATATTTTTTTGGTTATTTTGCCATTTGGCCGT
TTTTGGAAGAGTTTAAAATGTACTAGATAGAAAATGAATAAGTTTTGTGG
CTATTGAAAGACCTAATGATTTTGGTATTCAAACTATAACGTAGAAAATG
AAGATCTTTCGTTTATCTATTTTTAAAACAGAACTACATTGACTTGTCTT
TGATCGATATTTTGCATTGTAGATCTCAATGCCTGGTATGATGGACACTG
TACTTAACCTTGGCTTGAACGACCAAGTCGTCGTTGGTCTGGCCGCAAAA
AGCGGAGAGCGTTTTGCTTACGATTCGTTCCGGCGTTTTCTTGATATGTT
TGGTGATGTTGTAAGTCCTCTGTTTTTCAATACTATTTCAGGTAACTTGC
ATGACAAGAAAATTCTTTGACCTACCTTATAATTGTTTTCTTGATCAATA
AAAGGTGATGGGAATTCCACACGCCAAGTTTGAAGAGAAGTTAGAGAGAA
TGAAGGAGAGGAAAGGAGTTAAAAATGACACTGACTTAAGCGCGGCTGAT
CTCAAGGAATTGGTTGAGCAGTACAAGAGTGTTTACTTAGAGGCCAAGGG
TCAAGAGTTTCCTTCAGGTTTGTTTTGATTCCTACTTGAGGTCAAGTGAT
```

-continued

```
AAAAATTAGTTATTAGTTACAAATGTTTAAACGGGGTTAATTGCAGATCC
AAAGAAGCAATTGGAGCTAGCGATTGAAGCGGTATTCGATTCTTGGGATA
GCCCGAGAGCGAACAAGTACAGAAGTATTAACCAGATAACTGGATTGAAA
GGAACCGCGGTTAACATTCAGTGTATGGTGTTTGGAAACATGGGGACAC
TTCAGGGACTGGTGTTCTCTTCACTAGGAACCCTAGCACAGGAGAGAAGA
AGCTTTATGGCGAGTTTCTAGTTAATGCTCAGGTTTGGCATCTATCACAA
TGTGTGAATCTCATATCAACAAGTAAGCCCATACTCATTAAATATTGGTT
TTGGGACAGGGAGAGGATGTGGTTGCAGGGATAAGAACACCAGAAGATTT
GGATACAATGAAGAGATTTATGCCTGAGGCTTACGCTGAACTTGTTGAGA
ACTGCAACATCTTAGAAAGACATTACAAAGACATGATGGTTGATACACAT
AAACAATACTTCAATTAGTCCTCATCAACAATTCTTTAGTAATTTAAACA
AAATCTCAAATGTGTATTGCAGGATATTGAATTCACAGTACAAGAAGAGA
GATTGTGGATGCTGCAATGCAGAGCGGGTAAGCGAACGGGTAAAGGCGCC
GTGAAGATAGCAGTTGATATGGTAGGTGAAGGGCTTGTTGAGAAATCTTC
TGCTATCAAAATGGTGGAGCCTCAACATCTTGATCAACTACTTCACCCAC
AGGTACAAACTCAAATATTCATCTTCTTCTTTTTTCATAGTCATAAACTT
GATGTTGAAACCAAAATTCGAAACTTACTGGTAATGATTGGTTCACTTGA
ACAAGAACTAATGGGTTTAAGACGTTTAGGGTTTAGGAGTAAAAGCAGAG
ATGATTGTCTGACACGTAACCGATGAATAGGGTTTGGAAATTTTGATTCA
GAGGTCAATGAAGGTTTTTTTTTTTTTTTTATTGATGGATTAGTTTCA
TGATCCATCGGGGTATCGTGAAAAAGTGGTGGCCAAAGGCTTACCTGCGT
CACCAGGAGCGGCGGTTGGACAGGTTGTGTTCACGGCGGAGGAAGCCGAA
GCTTGGCATTCTCAGGGTAAAACTGTGATTCTGGTTCGAACTGAGACAAG
CCCTGACGATGTGGGAGGTATGCACGCAGCGGAAGGTATATTGACGGCTA
GAGGAGGAATGACGTCACACGCGGCTGTTGTTGCTCGCGGTTGGGGAAAA
TGTTGCATTGCTGGTTGTTCCGAGATTCGTGTCGACGAGAACCACAAGGT
TTTTGGATTCGATTTTAGAAACTTGTCATATAAGTTAGGGGAAGATTGTT
TCTAAAGTTAGGGTTTAAAAATTTTCAGGTTCTATTGATTGGAGATTTGA
CGATTAATGAAGGCGAATGGATCTCAATGAACGGATCAACCGGTGAGGTT
ATATTAGGGAAACAAGCATTGGCTCCTCCGGCTTTAAGTCCAGATTTGGA
GACTTTCATGTCCTGGGCTGATGCAATCAGACGTCTCAAGGTGTTTATGA
GTTTCTGTTCCTTTAACTTGTTTGATATTTTTAAACTTTCTAACTCAAAT
GTTCGATGACCGATAAGGTTATGGCGAATGCGGATACACCTGAAGACGCC
ATTGCAGCTAGGAAAAACGGAGCTCAAGGAATCGGGCTTTGTAGGACAGA
GCATATGGTAACTCCTCCTCTGTACTTGATTTCATGTTTTTGATGATTTA
GATTGTTTGTATCCAAATGTTTAATGTTGTCTTTGGTTTGGTTTTTAAGT
TCTTTGGAGCAGATAGGATTAAAGCAGTGAGAAAGATGATAATGGCGGTA
ACAACAGAGCAAAGGAAAGCTTCTCTCGACATCTTGCTTCCTTACCAACG
TTCGGATTTCGAAGGGATCTTCCGTGCTATGGATGGTAAATGTTTTGAGT
CGTCTCTCTAAAATGTATCACAACTTAAAACATGCCTAAACCTTTTTATT
```

-continued

```
TTTCTAGGTTTACCGGTAACAATCCGTTTGTTAGACCCTCCGCTTCACGA
GTTTCTCCCGGAAGGCGACTTGGACAACATTGTACATGAGCTAGCTGAAG
AAACTGGTGTGAAAGAAGATGAAGTCTTGTCACGGATAGAGAAACTCTCT
GAAGTGAATCCAATGCTTGGTTTCCGCGGTTGCAGGTTTCTTACTCTCTT
TGTTTCTCTCTGTCTCTTTGCACCTGAAGAACAATCTGATGATCGGTAAA
CTTGTACGTTATAGGCTCGGAATATCGTATCCAGAGCTAACGGAGATGCA
AGCGCGTGCAATTTTTGAAGCTGCAGCGTCAATGCAGGACCAAGGTGTTA
CTGTCATTCCTGAGATTATGGTTCCACTTGTAGGAACTCCTCAGGAATTG
GGTCACCAAGTTGATGTAATTCGTAAAGTTGCAAAGAAAGTATTTGCTGA
GAAGGGTCATACCGTGAGCTACAAGGTTGGGACAATGATTGAGATCCCTC
GAGCCGCGCTCATTGCAGATGAGGTAAATGTAACAAGACACAAAATGTGT
TTTAGGCACTTGAAACCATGTTGCTATTTGCTAAGTAGGAACCTTTTTCT
TTTGACAGATTGCGAAAGAGGCGGAGTTTTTCTCGTTCGGGACAAACGAC
TTGACGCAGATGACGTTTGGATACAGTAGAGACGATGTCGGCAAGTTTCT
ACCGATTTACCTCGCCAAAGGAATCTTACAGCACGACCCTTTTGAGGTAT
AATGACTACCATTTCGTTTGCTCTCTATCCATAGGATAAAATCTTGATAG
CCATTTTTTGTGTTTGGACCAGGTTCTTGATCAGCAAGGTGTAGGGCAA
TTGATCAAGATGGCGACAGAAAAAGGACGAGCAGCTAGGCCTAGCCTCAA
GGTTGGGATATGTGGAGAACATGGAGGAGATCCATCTTCTGTGGGATTCT
TTGCTGAAGCAGGACTTGACTATGTCTCTTGTTCTCCTTTCAGGTAATTG
ATTAATTTCCAAACCAATAAACACTTTTTTTACAACACTATTGTATAACT
CAGATTGATGTAATTTTGGGATTTCTGTTGTTGTTGTTGTTGTTGTTGTT
GTTGCAGGGTTCCAATTGCAAGGCTTGCAGCTGCTCAAGTAGTTGTTGCA
TGA
```

The cDNA sequence encoding the cytosolic form of the *Arabidopsis* pyruvate orthophosphate dikinase (PPDK) is provided herein as SEQ ID No:21, as follows:

```
                                           SEQ ID No: 21
ATGATGCAGCGAGTATTCACCTTTGGAAAAGGAAGAAGCGAAGGCAACAA
GGGCATGAAGTCCTTGTTGGGAGGGAAAGGAGCCAACCTGGCGGAGATGG
CTAGCATAGGCTTGTCGGTGCCGCCGGGGCTAACCATATCGACGGAGGCT
TGTCAGCAGTATCGATCGCCGGCAAAAAGCTTCCAGAAGGGTTTATGGGA
AGAGATCTTAGAAGGTCTTAGCTTCATCGAACGTGACATTGGAGCTTCCC
TCGCTGATCCCTCCAAGCCACTCCTCCTCTCTGTTCGCTCCGGCGCCGCC
ATCTCAATGCCTGGTATGATGGACACTGTACTTAACCTTGGCTTGAACGA
CCAAGTCGTCGTTGGTCTGGCCGCAAAAAGCGGAGAGCGTTTTGCTTACG
ATTCGTTCCGGCGTTTTCTTGATATGTTTGGTGATGTTGTGATGGGAATT
CCACACGCCAAGTTTGAAGAGAAGTTAGAGAGAATGAAGGAGAGGAAAGG
AGTTAAAAATGACACTGACTTAAGCGCGGCTGATCTCAAGGAATTGGTTG
AGCAGTACAAGAGTGTTTACTTAGAGGCCAAGGGTCAAGAGTTTCCTTCA
GATCCAAAGAAGCAATTGGAGCTAGCGATTGAAGCGGTATTCGATTCTTG
GGATAGCCCGAGAGCGAACAAGTACAGAAGTATTAACCAGATAACTGGAT
TGAAAGGAACCGCGGTTAACATTCAGTGTATGGTGTTTGGAAACATGGGG
GACACTTCAGGGACTGGTGTTCTCTTCACTAGGAACCCTAGCACAGGAGA
GAAGAAGCTTTATGGCGAGTTTCTAGTTAATGCTCAGGTTTGGCATCTAT
CACAATGTGTGAATCTCATATCAACAAGGATAAGAACACCAGAAGATTTG
GATACAATGAAGAGATTTATGCCTGAGGCTTACGCTGAACTTGTTGAGAA
CTGCAACATCTTAGAAAGACATTACAAAGACATGATGGATATTGAATTCA
CAGTACAAGAAGAGAGATTGTGGATGCTGCAATGCAGAGCGGGTAAGCGA
ACGGGTAAAGGCGCCGTGAAGATAGCAGTTGATATGGTAGGTGAAGGGCT
TGTTGAGAAATCTTCTGCTATCAAAATGGTGGAGCCTCAACATCTTGATC
AACTACTTCACCCACAGTTTCATGATCCATCGGGGTATCGTGAAAAAGTG
GTGGCCAAAGGCTTACCTGCGTCACCAGGAGCGGCGGTTGGACAGGTTGT
GTTCACGGCGGAGGAAGCCGAAGCTTGGCATTCTCAGGGTAAAACTGTGA
TTCTGGTTCGAACTGAGACAAGCCCTGACGATGTGGGAGGTATGCACGCA
GCGGAAGGTATATTGACGGCTAGAGGAGGAATGACGTCACACGCGGCTGT
TGTTGCTCGCGGTTGGGGAAAATGTTGCATTGCTGGTTGTTCCGAGATTC
GTGTCGACGAGAACCACAAGGTTCTATTGATTGGAGATTTGACGATTAAT
GAAGGCGAATGGATCTCAATGAACGGATCAACCGGTGAGGTTATATTAGG
GAAACAAGCATTGGCTCCTCCGGCTTTAAGTCCAGATTTGGAGACTTTCA
TGTCCTGGGCTGATGCAATCAGACGTCTCAAGGTTATGGCGAATGCGGAT
ACACCTGAAGACGCCATTGCAGCTAGGAAAAACGGAGCTCAAGGAATCGG
GCTTTGTAGGACAGAGCATATGATTGTTTGTATCCAAATGTTTAATGTTG
TCTTTGGTTTGTTTTTAAGTTCTTTGGAGCAGATAGGATTAAAGCAGTG
AGAAAGATGATAATGGCGGTAACAACAGAGCAAAGGAAAGCTTCTCTCGA
CATCTTGCTTCCTTACCAACGTTCGGATTTCGAAGGGATCTTCCGTGCTA
TGGATGGTTTACCGGTAACAATCCGTTTGTTAGACCCTCCGCTTCACGAG
TTTCTCCCGGAAGGCGACTTGGACAACATTGTACATGAGCTAGCTGAAGA
AACTGGTGTGAAAGAAGATGAAGTCTTGTCACGGATAGAGAAACTCTCTG
AAGTGAATCCAATGCTTGGTTTCCGCGGTTGCAGGCTCGGAATATCGTAT
CCAGAGCTAACGGAGATGCAAGCGCGTGCAATTTTTGAAGCTGCAGCGTC
AATGCAGGACCAAGGTGTTACTGTCATTCCTGAGATTATGGTTCCACTTG
TAGGAACTCCTCAGGAATTGGGTCACCAAGTTGATGTAATTCGTAAAGTT
GCAAAGAAAGTATTTGCTGAGAAGGGTCATACCGTGAGCTACAAGGTTGG
GACAATGATTGAGATCCCTCGAGCCGCGCTCATTGCAGATGAGATTGCGA
AAGAGGCGGAGTTTTTCTCGTTCGGGACAAACGACTTGACGCAGATGACG
TTTGGATACAGTAGAGACGATGTCGGCAAGTTTCTACCGATTTACCTCGC
CAAAGGAATCTTACAGCACGACCCTTTTGAGGTTCTTGATCAGCAAGGTG
TAGGGCAATTGATCAAGATGGCGACAGAAAAAGGACGAGCAGCTAGGCCT
AGCCTCAAGGTTGGGATATGTGGAGAACATGGAGGAGATCCATCTTCTGT
GGGATTCTTTGCTGAAGCAGGACTTGACTATGTCTCTTGTTCTCCTTTCA
GGGTTCCAATTGCAAGGCTTGCAGCTGCTCAAGTAGTTGTTGCATGA
```

The cDNA sequence encoding the chloroplastic form of the *Arabidopsis* pyruvate orthophosphate dikinase (PPDK) is provided herein as SEQ ID No:22, as follows:

```
                                          SEQ ID No: 22
ATGACAAGTATGATCGTGAAGACAACGCCGGAGCTCTTCAAAGGAAATGG
AGTGTTCCGTACGGATCATCTCGGAGAAAACCGAATGGTTAGTCGATCAA
ACCGGCTAGGTGATGGATCAAACCGTTTCCCTAGAACCGGTACAATCCAT
TGCCAACGGTTAAGCATAGCAAAGACCGGTTTGCATCGTGAGACGAAGGC
TCGAGCCATACTTAGCCCTGTGTCCGATCCGGCCGCTTCCATAGCCCAAA
AGCGAGTATTCACCTTTGGAAAAGGAAGAAGCGAAGGCAACAAGGGCATG
AAGTCCTTGTTGGGAGGGAAAGGAGCCAACCTGGCGGAGATGGCTAGCAT
AGGCTTGTCGGTGCCGCCGGGGCTAACCATATCGACGGAGGCTTGTCAGC
AGTATCAGATCGCCGGCAAAAAGCTTCCAGAAGGTTTATGGGAAGAGATC
TTAGAAGGTCTTAGCTTCATCGAACGTGACATTGGAGCTTCCCTCGCTGA
TCCCTCCAAGCCACTCCTCCTCTCTGTTCGCTCCGGCGCCGCCATCTCAA
TGCCTGGTATGATGGACACTGTACTTAACCTTGGCTTGAACGACCAAGTC
GTCGTTGGTCTGGCCGCAAAAAGCGGAGAGCGTTTTGCTTACGATTCGTT
CCGGCGTTTTCTTGATATGTTTGGTGATGTTGTGATGGGAATTCCACACG
CCAAGTTTGAAGAGAAGTTAGAGAGAATGAAGGAGAGGAAAGGAGTTAAA
AATGACACTGACTTAAGCGCGGCTGATCTCAAGGAATTGGTTGAGCAGTA
CAAGAGTGTTTACTTAGAGGCCAAGGGTCAAGAGTTTCCTTCAGATCCAA
AGAAGCAATTGGAGCTAGCGATTGAAGCGGTATTCGATTCTTGGGATAGC
CCGAGAGCGAACAAGTACAGAAGTATTAACCAGATAACTGGATTGAAAGG
AACCGCGGTTAACATTCAGTGTATGGTGTTTGGAAACATGGGGACACTT
CAGGGACTGGTGTTCTCTTCACTAGGAACCCTAGCACAGGAGAGAAGAAG
CTTTATGGCGAGTTTCTAGTTAATGCTCAGGTTTGGCATCTATCACAATG
TGTGAATCTCATATCAACAAGGATAAGAACACCAGAAGATTTGGATACAA
TGAAGAGATTTATGCCTGAGGCTTACGCTGAACTTGTTGAGAACTGCAAC
ATCTTAGAAAGACATTACAAAGACATGATGGATATTGAATTCACAGTACA
AGAAGAGAGATTGTGGATGCTGCAATGCAGAGCGGGTAAGCGAACGGTA
AAGGCGCCGTGAAGATAGCAGTTGATATGGTAGGTGAAGGGCTTGTTGAG
AAATCTTCTGCTATCAAAATGGTGGAGCCTCAACATCTTGATCAACTACT
TCACCCACAGTTTCATGATCCATCGGGGTATCGTGAAAAAGTGGTGGCCA
AAGGCTTACCTGCGTCACCAGGAGCGGCGGTTGGACAGGTTGTGTTCACG
GCGGAGGAAGCCGAAGCTTGGCATTCTCAGGGTAAAACTGTGATTCTGGT
TCGAACTGAGACAAGCCCTGACGATGTGGGAGGTATGCACGCAGCGGAAG
GTATATTGACGGCTAGAGGAGGAATGACGTCACACGCGGCTGTTGTTGCT
CGCGGTTGGGGAAAATGTTGCATTGCTGGTTGTTCCGAGATTCGTGTCGA
CGAGAACCACAAGGTTCTATTGATTGGAGATTTGACGATTAATGAAGGCG
AATGGATCTCAATGAACGGATCAACCGGTGAGGTTATATTAGGGAAACAA
GCATTGGCTCCTCCGGCTTTAAGTCCAGATTTGGAGACTTTCATGTCCTG
GGCTGATGCAATCAGACGTCTCAAGGTTATGGCGAATGCGGATACACCTG
AAGACGCCATTGCAGCTAGGAAAAACGGAGCTCAAGGAATCGGGCTTTGT
AGGACAGAGCATATGATTGTTTGTATCCAAATGTTTAATGTTGTCTTTGG
TTTGGTTTTTAAGTTCTTTGGAGCAGATAGGATTAAAGCAGTGAGAAAGA
TGATAATGGCGGTAACAACAGAGCAAAGGAAAGCTTCTCTCGACATCTTG
CTTCCTTACCAACGTTCGGATTTCGAAGGGATCTTCCGTGCTATGGATGG
TTTACCGGTAACAATCCGTTTGTTAGACCCTCCGCTTCACGAGTTTCTCC
CGGAAGGCGACTTGGACAACATTGTACATGAGCTAGCTGAAGAAACTGGT
GTGAAAGAAGATGAAGTCTTGTCACGGATAGAGAAACTCTCTGAAGTGAA
TCCAATGCTTGGTTTCCGCGGTTGCAGGCTCGGAATATCGTATCCAGAGC
TAACGGAGATGCAAGCGCGTGCAATTTTTGAAGCTGCAGCGTCAATGCAG
GACCAAGGTGTTACTGTCATTCCTGAGATTATGGTTCCACTTGTAGGAAC
TCCTCAGGAATTGGGTCACCAAGTTGATGTAATTCGTAAAGTTGCAAAGA
AAGTATTTGCTGAGAAGGGTCATACCGTGAGCTACAAGGTTGGGACAATG
ATTGAGATCCCTCGAGCCGCGCTCATTGCAGATGAGATTGCGAAAGAGGC
GGAGTTTTTCTCGTTCGGGACAAACGACTTGACGCAGATGACGTTTGGAT
ACAGTAGAGACGATGTCGGCAAGTTTCTACCGATTTACCTCGCCAAAGGA
ATCTTACAGCACGACCCTTTTGAGGTTCTTGATCAGCAAGGTGTAGGGCA
ATTGATCAAGATGGCGACAGAAAAAGGACGAGCAGCTAGGCCTAGCCTCA
AGGTTGGGATATGTGGAGAACATGGAGGAGATCCATCTTCTGTGGGATTC
TTTGCTGAAGCAGGACTTGACTATGTCTCTTGTTCTCCTTTCAGGGTTCC
AATTGCAAGGCTTGCAGCTGCTCAAGTAGTTGTTGCATGA
```

Accordingly, the coding sequence, which encodes a polypeptide having PPDK activity, may comprise a nucleic acid sequence substantially as set out in SEQ ID No:20, SEQ ID No.21 or SEQ ID No.22, or a functional variant or fragment thereof.

The polypeptide sequence of the cytosolic form of *Arabidopsis* PPDK is provided herein as SEQ ID No:23, as follows:

```
                                          SEQ ID No: 23
MMQRVFTFGKGRSEGNKGMKSLLGGKGANLAEMASIGLSVPPGLTISTEA
CQQYQIAGKKLPEGLWEEILEGLSFIERDIGASLADPSKPLLLSVRSGAA
ISMPGMMDTVLNLGLNDQVVVGLAAKSGERFAYDSFRRFLDMFGDVVMGI
PHAKFEEKLERMKERKGVKNDTDLSAADLKELVEQYKSVYLEAKGQEFPS
DPKKQLELAIEAVFDSWDSPRANKYRSINQITGLKGTAVNIQCMVFGNMG
DTSGTGVLFTRNPSTGEKKLYGEFLVNAQVWHLSQCVNLISTRIRTPEDL
DTMKRFMPEAYAELVENCNILERHYKDMMDIEFTVQEERLWMLQCRAGKR
TGKGAVKIAVDMVGEGLVEKSSAIKMVEPQHLDQLLHPQFHDPSGYREKV
VAKGLPASPGAAVGQVVFTAEEAEAWHSQGKTVILVRTETSPDDVGGMHA
AEGILTARGGMTSHAAVVARGWGKCCIAGCSEIRVDENHKVLLIGDLTIN
EGEWISMNGSTGEVILGKQALAPPALSPDLETFMSWADAIRRLKVMANAD
TPEDAIAARKNGAQGIGLCRTEHMIVCIQMFNVVFGLVFKFFGADRIKAV
RKMIMAVTTEQRKASLDILLPYQRSDFEGIFRAMDGLPVTIRLLDPPLHE
```

```
FLPEGDLDNIVHELAEETGVKEDEVLSRIEKLSEVNPMLGFRGCRLGISY

PELTEMQARAIFEAAASMQDQGVTVIPEIMVPLVGTPQELGHQVDVIRKV

AKKVFAEKGHTVSYKVGTMIEIPRAALIADEIAKEAEFFSFGTNDLTQMT

FGYSRDDVGKFLPIYLAKGILQHDPFEVLDQQGVGQLIKMATEKGRAARP

SLKVGICGEHGGDPSSVGFFAEAGLDYVSCSPFRVPIARLAAAQVVVA
```

The polypeptide sequence of the chloroplastic form of Arabidopsis PPDK is provided herein as SEQ ID No:24, as follows:

```
                                              SEQ ID No: 24
MTSMIVKTTPELFKGNGVFRTDHLGENRMVSRSNRLGDGSNRFPRTGTIH

CQRLSIAKTGLHRETKARAILSPVSDPAASIAQKRVFTFGKGRSEGNKGM

KSLLGGKGANLAEMASIGLSVPPGLTISTEACQQYQIAGKKLPEGLWEEI

LEGLSFIERDIGASLADPSKPLLLSVRSGAAISMPGMMDTVLNLGLNDQV

VVGLAAKSGERFAYDSFRRFLDMFGDVVMGIPHAKFEEKLERMKERKGVK

NDTDLSAADLKELVEQYKSVYLEAKGQEFPSDPKKQLELAIEAVFDSWDS

PRANKYRSINQITGLKGTAVNIQCMVFGNMGDTSGTGVLFTRNPSTGEKK

LYGEFLVNAQVWHLSQCVNLISTRIRTPEDLDTMKRFMPEAYAELVENCN

ILERHYKDMMDIEFTVQEERLWMLQCRAGKRTGKGAVKIAVDMVGEGLVE

KSSAIKMVEPQHLDQLLHPQFHDPSGYREKVVAKGLPASPGAAVGQVVFT

AEEAEAWHSQGKTVILVRTETSPDDVGGMHAAEGILTARGGMTSHAAVVA

RGWGKCCIAGCSEIRVDENHKVLLIGDLTINEGEWISMNGSTGEVILGKQ

ALAPPALSPDLETFMSWADAIRRLKVMANADTPEDAIAARKNGAQGIGLC

RTEHMIVCIQMFNVVFGLVFKFFGADRIKAVRKMIMAVTTEQRKASLDIL

LPYQRSDFEGIFRAMDGLPVTIRLLDPPLHEFLPEGDLDNIVHELAEETG

VKEDEVLSRIEKLSEVNPMLGFRGCRLGISYPELTEMQARAIFEAAASMQ

DQGVTVIPEIMVPLVGTPQELGHQVDVIRKVAKKVFAEKGHTVSYKVGTM

IEIPRAALIADEIAKEAEFFSFGTNDLTQMTFGYSRDDVGKFLPIYLAKG

ILQHDPFEVLDQQGVGQLIKMATEKGRAARPSLKVGICGEHGGDPSSVGF

FAEAGLDYVSCSPFRVPIARLAAAQVVVA
```

Accordingly, the polypeptide having PPDK activity may comprise an amino acid sequence substantially as set out in SEQ ID No:23 or SEQ ID No.24, or a functional variant or fragment thereof. Since highest PPDK abundance was observed almost exclusively in cell lines harbouring genomic DNA encoding PPDK, it appears that introns may have a positive effect on PPDK expression. As such, in one embodiment, the construct may comprise the cDNA of the genes encoding either PPDK and/or PCK.

Genetic constructs of the invention may be in the form of an expression cassette, which may be suitable for expression of the at least one coding sequence in a host cell. The genetic construct of the invention may be introduced in to a host cell without it being incorporated in a vector. For instance, the genetic construct, which may be a nucleic acid molecule, may be incorporated within a liposome or a virus particle. Alternatively, a purified nucleic acid molecule (e.g. histone-free DNA, or naked DNA) may be inserted directly into a host cell by suitable means, e.g. direct endocytotic uptake. The genetic construct may be introduced directly in to cells of a host subject (e.g. a plant) by transfection, infection, microinjection, cell fusion, protoplast fusion or ballistic bombardment. Alternatively, genetic constructs of the invention may be introduced directly into a host cell using a particle gun. Alternatively, the genetic construct may be harboured within a recombinant vector, for expression in a suitable host cell.

Hence, in a third aspect, there is provided a recombinant vector comprising the genetic construct according to the first or second aspect.

The recombinant vector may be a plasmid, cosmid or phage. Such recombinant vectors are highly useful for transforming host cells with the genetic construct of the invention, and for replicating the expression cassette therein. The skilled technician will appreciate that genetic constructs of the invention may be combined with many types of backbone vector for expression purposes. The backbone vector may be a binary vector, for example one which can replicate in both E. coli and Agrobacterium tumefaciens. For example, a suitable vector may be a pBIN plasmid, such as pBIN19. However, a preferred backbone vector is BNP1380000001, which is based on pBINPLUS (F. A. van Engelen et al. Transgenic Research (1995) 4, 288-290), and which harbours the SAG12 promoter.

Recombinant vectors may include a variety of other functional elements in addition to the promoter (e.g. a senescence-associated promoter), and the at least one coding sequence (encoding PCK and/or PPDK). For instance, the recombinant vector may be designed such that it autonomously replicates in the cytosol of the host cell. In this case, elements which induce or regulate DNA replication may be required in the recombinant vector. Alternatively, the recombinant vector may be designed such that it integrates into the genome of a host cell. In this case, DNA sequences which favour targeted integration (e.g. by homologous recombination) are envisaged.

The recombinant vector may also comprise DNA coding for a gene that may be used as a selectable marker in the cloning process, i.e. to enable selection of cells that have been transfected or transformed, and to enable the selection of cells harbouring vectors incorporating heterologous DNA. The vector may also comprise DNA involved with regulating expression of the coding sequence, or for targeting the expressed polypeptide to a certain part of the host cell, e.g. the chloroplast. Hence, the vector of the third aspect may comprise at least one additional element selected from a group consisting of: a selectable marker gene (e.g. an antibiotic resistance gene); a polypeptide termination signal; and a protein targeting sequence (e.g. a chloroplast transit peptide).

Examples of suitable marker genes include antibiotic resistance genes such as those conferring resistance to Kanamycin, Geneticin (G418) and Hygromycin (npt-II, hyg-B); herbicide resistance genes, such as those conferring resistance to phosphinothricin and sulphonamide based herbicides (bar and suI respectively; EP-A-242246, EP0369637A2); and screenable markers such as beta-glucuronidase (GB2197653), luciferase and green fluorescent protein (GFP). The marker gene may be controlled by a second promoter (which may not be a senescence-associated promoter), which allows expression in cells, which may or may not be in the seed, thereby allowing the selection of cells or tissue containing the marker at any stage of development of the plant. Suitable second promoters are the promoter of nopaline synthase gene of Agrobacterium and the promoter derived from the gene which encodes the 35S cauliflower mosaic virus (CaMV) transcript. However, any other suitable second promoter may be used.

The various embodiments of genetic constructs of the invention may be prepared using the cloning procedure illustrated in FIG. 1, which may be summarised as follows. The genomic and cDNA versions of the genes encoding PCK and PPDK may be amplified from the genomic or cDNA templates by PCR using suitable primers. PCR products may be examined using agarose gel electrophoresis. The PCR products may then be ligated into a suitable vector for cloning purposes, for example the pCR4 Blunt-TOPO vector (Invitrogen). Vectors harbouring the PCR products may be grown up in a suitable host, such as *E. coli*. *E. coli* colonies may then be screened by PCR using suitable primers, and inserts in plasmids showing the correct restriction enzyme digest pattern may be sequenced using suitable primers.

*E. coli* colonies carrying TOPO-cDNA (PCK or PPDK) or TOPO-gDNA (PCK or PPDK) may be cultured to produce a suitable amount of each plasmid, which may then be purified. The plasmids may then be digested to release a DNA fragment encoding PPDK or PCK, which may then be cloned into a vector harbouring a suitable promoter, for example a SAG promoter, such as a pBNP plasmid. The resultant PPDK constructs were named BNP-PPDKcDNA and BNP-PPDKgDNA, and the resultant PCK constructs were named pALBNP1 (cDNA) and pALBNP2 (gDNA). Embodiments of the vector according to the third aspect may be substantially as set out in FIG. 3.

In a fourth aspect, there is provided a method of increasing the concentration of PCK and/or PPDK in a leaf of a test plant to above that of the corresponding concentration of PCK and/or PPDK in a wild-type plant cultured under the same conditions, the method comprising altering plant metabolism in the test plant to achieve increased levels of PCK and/or PPDK in plant leaves after the initiation of leaf senescence.

In a fifth aspect, there is provided a method of decreasing the concentration of nitrogen in the leaves of a test plant to below that of the corresponding concentration of nitrogen in a wild-type plant cultured under the same conditions, the method comprising altering plant metabolism in the test plant to achieve increased levels of PCK and/or PPDK in plant leaves after the initiation of leaf senescence.

In a sixth aspect, there is provided a method of increasing the growth rate of a test plant compared to the corresponding growth rate of a wild-type plant cultured under the same conditions, the method comprising altering plant metabolism in the test plant to achieve increased levels of PCK and/or PPDK in plant leaves after the initiation of leaf senescence.

Methods for determining the level of nitrogen in plant leaves, and plant growth rates, are set out in the Examples. The methods of the fourth, fifth or sixth aspects may comprise transforming a test plant cell with a genetic construct according to the first or second aspect, or a vector according to the third aspect. The genetic construct or the vector may be introduced into a host cell by any suitable means.

In a seventh aspect, there is provided a cell comprising the genetic construct according to the first or second aspect, or the recombinant vector according to the third aspect.

The cell may be a plant cell. As the inventors have observed that over-expressing both PCK and/or PPDK in a host cell is surprisingly effective at inducing nitrogen remobilisation in senescent leaves, the cell of the seventh aspect may comprise one or more constructs of the first or second aspect, or one or more vectors of the third aspect, such that both PCK and/or PPDK are over-expressed.

For example, the host cell may be transformed with the first embodiment of the genetic construct of the first aspect (i.e. the PCK construct) only. Alternatively, the host cell may be transformed with the second embodiment of the genetic construct of the second aspect (i.e. the PPDK construct) only. In another embodiment, the host cell may be transformed with the first and second embodiments of the genetic construct of the first aspect, such that both PCK and PPDK are expressed in the host cell. The host cell may alternatively be transformed with the third or fourth embodiments of the construct of the first aspect (i.e. PCK/PPDK constructs 1 or 2), such that both PCK and PPDK are expressed in the host cell. It is also envisaged that the host cell may be transformed with the construct of the second aspect, which encodes both PCK and PPDK.

The cell may be transformed with the genetic construct or the vector according to the invention, using known techniques. Suitable means for introducing the genetic construct into the host cell may include use of a disarmed Ti-plasmid vector carried by *Agrobacterium* by procedures known in the art, for example as described in EP-A-0116718 and EP-A-0270822. A further method may be to transform a plant protoplast, which involves first removing the cell wall and introducing the nucleic acid, and then reforming the cell wall. The transformed cell may then be grown into a plant.

In an eighth aspect, there is provided a transgenic plant comprising the genetic construct according to the first or second aspect, or the vector according to the third aspect.

The transgenic plant according to the eighth aspect may include the Brassicaceae family, such as *Brassica* spp. The plant may be *Brassica napus* (oilseed rape).

Further examples of transgenic plants according to the eighth aspect include the family Poales, such as *Triticeae* spp. The plant may be *Triticum* spp. (wheat). Increasing the grain protein content in wheat may result in increased volume of food products comprising wheat, such as bread.

Further examples of suitable transgenic plants according to the eighth aspect include the Solanaceae family of plants which include, for example jimson weed, eggplant, mandrake, deadly nightshade (belladonna), *capsicum* (paprika, chilli pepper), potato and tobacco. One example of a suitable genus of Solanaceae is *Nicotiana*. A suitable species of *Nicotiana* may be referred to as tobacco plant, or simply tobacco. Various methods for transforming plants with the genetic construct of the first or second aspect, or vector of the third aspect, are known and can be used in the present invention.

For example, tobacco may be transformed as follows. *Nicotiana tabacum* is transformed using the method of leaf disk co-cultivation essentially as described by Horsch et al. (Science 227: 1229-1231, 1985). The youngest two expanded leaves may be taken from 7 week old tobacco plants and may be surface sterilised in 8% Domestos™ for 10 minutes and washed 6 times with sterile distilled water. Leaf disks may be cut using a number 6 cork borer and placed in the *Agrobacterium* suspension, containing the appropriate binary vectors (according to the invention), for approximately two minutes. The discs may be gently blotted between two sheets of sterile filter paper. Ten disks may be placed on LS 3% sucrose+2 µM BAP+0.2 µM NAA plates, which may then be incubated for 2 days in the growth room. Discs may be transferred to plates of LS+3% sucrose+2 µM BAP+0.2 µM NAA supplemented with 500 g/l claforan and 100 g/l kanamycin. The discs may be transferred onto fresh plates of above medium after 2 weeks. After a further two weeks, the leaf disks may be transferred onto plates containing LS+3% sucrose+0.5 µM BAP supplemented with 500 mg/l claforan and 100 mg/l kanamycin. The leaf disks may be transferred onto fresh medium every two weeks. As shoots appear, they may be excised and transferred to jars of LS+3% sucrose supplemented with 500 mg/l claforan. The shoots in jars may be transferred to LS+3% sucrose+250 mg/l claforan after approximately 4 weeks. After a further 3-4 weeks the plants may be transferred to LS+3% sucrose (no antibiotics) and rooted. Once the plants are rooted they may be transferred to soil in the greenhouse.

In a ninth aspect, there is provided a plant propagation product obtainable from the transgenic plant according to the eighth aspect.

A "plant propagation product" may be any plant matter taken from a plant from which further plants may be produced. Suitably, the plant propagation product may be a seed.

In a tenth aspect of the invention, there is provided a method of producing a transgenic plant which remobilises nitrogen at a higher rate than a corresponding wild-type plant cultured under the same conditions, the method comprising the steps of:—
i) transforming a plant cell with the genetic construct according to the first or second aspect, or the vector according to the third aspect; and
ii) regenerating a plant from the transformed cell.

In an eleventh aspect, there is provided a method of producing a transgenic plant having a higher growth rate than a corresponding wild-type plant cultured under the same conditions, the method comprising the steps of:—
i) transforming a plant cell with the genetic construct according to the first or second aspect, or the vector according to the third aspect; and
ii) regenerating a plant from the transformed cell.

Preferably, and advantageously, the methods according to the invention do not compromise the health or fitness of the test plant that is generated. Preferably, the methods comprise transforming the test plant, and preferably its leaves, with the genetic construct of the first or second aspect, or the vector of the third aspect. The inventors have observed that over-expressing both PCK and PPDK in a host cell is effective at inducing nitrogen remobilisation in senescent leaves. Hence, it is preferred that the methods of the tenth and eleventh aspect comprise transforming the test plant with one or more constructs of the invention such that both PCK and PPDK are over-expressed. For example, the test plant may be transformed with the first embodiment of the genetic construct of the first aspect of the invention (i.e. the PCK construct) and in addition the second embodiment of the construct of the first aspect (i.e. the PPDK construct). Hence, transformation of these two constructs result in over-expression of both enzymes. Alternatively, the test plant may be transformed with the third or fourth embodiments of the construct of the first aspect of the invention, each of which encode PCK and PPDK. Alternatively, the test plant may be transformed with the construct of the second aspect of the invention, which encodes both PCK and PPDK.

The inventors have observed that a plant leaf of a test plant which has been transformed with construct(s) which encode both PCK and PPDK exhibits increases in nitrogen remobilisation upon the onset of senescence such that the concentration of nitrogen decreases in that leaf. Furthermore, they observed an increase in vegetative growth rate. Although they are not bound by hypothesis, inventors believe that the decrease in nitrogen concentration in the leaves may induce the increase in growth rate, and hence crop yield.

In a twelfth aspect of the invention, there is provided a harvested leaf containing a lower level of nitrogen than the corresponding level of nitrogen in a harvested leaf taken from a wild-type plant cultured under the same conditions, wherein the leaf is harvested from the transgenic plant according to the eighth aspect, or produced by the method according to the tenth or eleventh aspect.

In a thirteenth aspect of the invention, there is provided a smoking article comprising nitrogen-reduced tobacco obtained from a mutant tobacco plant, which mutant is capable of decreasing the concentration of nitrogen in senescent leaves.

Nitrogen-reduced tobacco can include tobacco in which the nitrogen concentration is less than the corresponding concentration in a wild-type plant cultured under the same conditions. Such a smoking article may comprise tobacco obtained from a mutant tobacco plant, which may have been transformed with a genetic construct according to the first or second aspect of the invention, or a vector according to the third aspect.

As used herein, the term "smoking article" can include smokeable products, such as rolling tobacco, cigarettes, cigars and cigarillos whether based on tobacco, tobacco derivatives, expanded tobacco, reconstituted tobacco or tobacco substitutes and also heat-not-burn products.

It will be appreciated that the invention extends to any nucleic acid or peptide or variant, derivative or analogue thereof, which comprises substantially the amino acid or nucleic acid sequences of any of the sequences referred to herein, including functional variants or functional fragments thereof. The terms "substantially the amino acid/polynucleotide/polypeptide sequence", "functional variant" and "functional fragment", can be a sequence that has at least 40% sequence identity with the amino acid/polynucleotide/polypeptide sequences of any one of the sequences referred to herein, for example 40% identity with the gene identified as SEQ ID No.17 (which encodes one embodiment of PCK enzyme), or 40% identity with the polypeptide identified as SEQ ID No.19 (i.e. one embodiment of PCK enzyme), or 40% identity with the gene identified as SEQ ID No.21 (which encodes one embodiment of PPDK enzyme), or 40% identity with the polypeptide identified as SEQ ID No.23 (i.e. one embodiment of PPDK enzyme).

Amino acid/polynucleotide/polypeptide sequences with a sequence identity which is greater than 65%, more preferably greater than 70%, even more preferably greater than 75%, and still more preferably greater than 80% sequence identity to any of the sequences referred to is also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:—(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance. Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: ENDGAP=-1, and GAPDIST=4. Those skilled in the art will be aware that it may be necessary to vary these and other parameters for optimal sequence alignment.

Preferably, calculation of percentage identities between two amino acid/polynucleotide/polypeptide sequences is then calculated from such an alignment as (N/T)*100, where N is the number of positions at which the sequences share an identical residue, and T is the total number of positions compared including gaps but excluding overhangs. Hence, a most preferred method for calculating percentage identity between two sequences comprises (i) preparing a sequence alignment using the ClustalW program using a suitable set of parameters, for example, as set out above; and (ii) inserting the values of N and T into the following formula:—Sequence Identity=(N/T)*100.

Alternative methods for identifying similar sequences will be known to those skilled in the art. For example, a substantially similar nucleotide sequence will be encoded by a sequence which hybridizes to the sequences shown in SEQ ID Nos. 16, 17, 18, 20, 21, 22, or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2× SSC/0.1% SDS at approximately 20-65° C. Alternatively, a substantially similar polypeptide may differ by at least 1, but less than 5, 10, 20, 50 or 100 amino acids from the sequences shown in SEQ ID No's. 19, 23 or 24.

Due to the degeneracy of the genetic code, it is clear that any nucleic acid sequence could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will known the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:—

FIG. 1 shows the protocol used for the cloning of the genetic constructs, BNP-PPDKcDNA and BNP-PPD-KgDNA, in which: (a) PCR amplification of cDNA and genomic DNA forms of the cytosolic isoform of *Arabidopsis* PPDK; (b) Insertion into the cloning vector pCR 4Blunt-TOPO; (c) Restriction endonuclease digestion of the cloning vector (on left) to release PPDK, and the target SAG12-containing vector pBNP, with AvrII and BamHI (on right); (d) Ligation of PPDK into pBNP and an agarose gel showing DNA fragments produced by restriction endonuclease digestion of constructs with AvrII and BamHI; and (e) Constructs introduced into *Arabidopsis* ecotype Columbia 0 by *Agrobacterium*-mediated transformation;

FIG. 2a shows the plasmid pCR$_4$ BLUNT-TOPO (SEQ ID Nos: 29 and 30) used for the construction of expression vectors according to the invention.

FIG. 3a shows the plasmid pBNP containing the SAG12 promoter, and FIG. 3b is a table summarising that PPDK inserts (cDNA or gDNA) were introduced into pBNP using AvrII and BamHI digests, and that PCK inserts (cDNA or gDNA) were introduced into pBNP using XbaI and SacI digests, resulting in vectors according to embodiments of the invention;

FIG. 4 shows the selection of transgenic SAG12-PPDK *Arabidopsis thaliana* cell lines by Western blot. SAG12-PPDK cDNA cell lines are shown on top, and SAG12-PPDK gDNA cell lines are shown below;

FIG. 5 shows the quantification of PPDK abundance in wild-type, ΔPPDK and five independent SAG12-PPDKgDNA lines from week five onwards;

FIG. 6 shows the selection of SAG12-PPDK (cDNA and gDNA) in (b) K326 and in (c) Burley 21 tobacco lines;

FIG. 7 shows the overexpression of PPDK in ripe leaves of K326 tobacco;

FIG. 8 shows photos of rosettes of various cell lines of *Arabidopsis thaliana*, i.e. wild-type, ΔPPDK and SAG12-PPDKgDNA against time;

FIG. 9 shows the *Arabidopsis* reproductive tissue mass at week nine;

FIG. 10 shows the total plant fresh mass (i.e. rosette plus reproductive tissue) of wild-type and SAG12-PPDgDNA plants from weeks three to nine after sowing;

FIG. 11 shows the Nitrogen content in leaves of wild-type, ΔPPDK and SAG12-PPDKgDNA plants at week seven;

FIG. 12 shows the Nitrogen content of individual seeds of wild-type, ΔPPDK and SAG12-PPDK plants;

FIG. 13 shows the total free amino acid content in the leaves of wild-type, ΔPPDK and SAG12-PPDKgDNA *Arabidopsis* cell lines;

FIG. 14 shows the seed mass of various tobacco cell lines, zero copy=wild-type, G4 (gDNA), G10, G8 and C10 (cDNA) are SAG12-PPDK lines;

FIG. 15 shows the seed nitrogen content of various tobacco cell lines, zero copy=wild-type, G4 (gDNA), G10, G8 and C10 (cDNA) are SAG12-PPDK lines;

FIG. 16 are the results of Western blotting for PCK/PPDK double inserts. All lines show higher levels of PCK especially in week 7 which correlates with activity of the SAG12 promoter;

FIG. 17 shows that expression of both PCK and PPDK in transformed plants leads to an increase in rosette mass compared to control 7; and FIG. 18 shows a postulated biochemical pathway indicating that nitrogen remobilisation may occur through PCK- and PPDK-dependent formation of the transport amino acids asparagine and glutamine.

EXAMPLES

Example 1

Figure 2B:
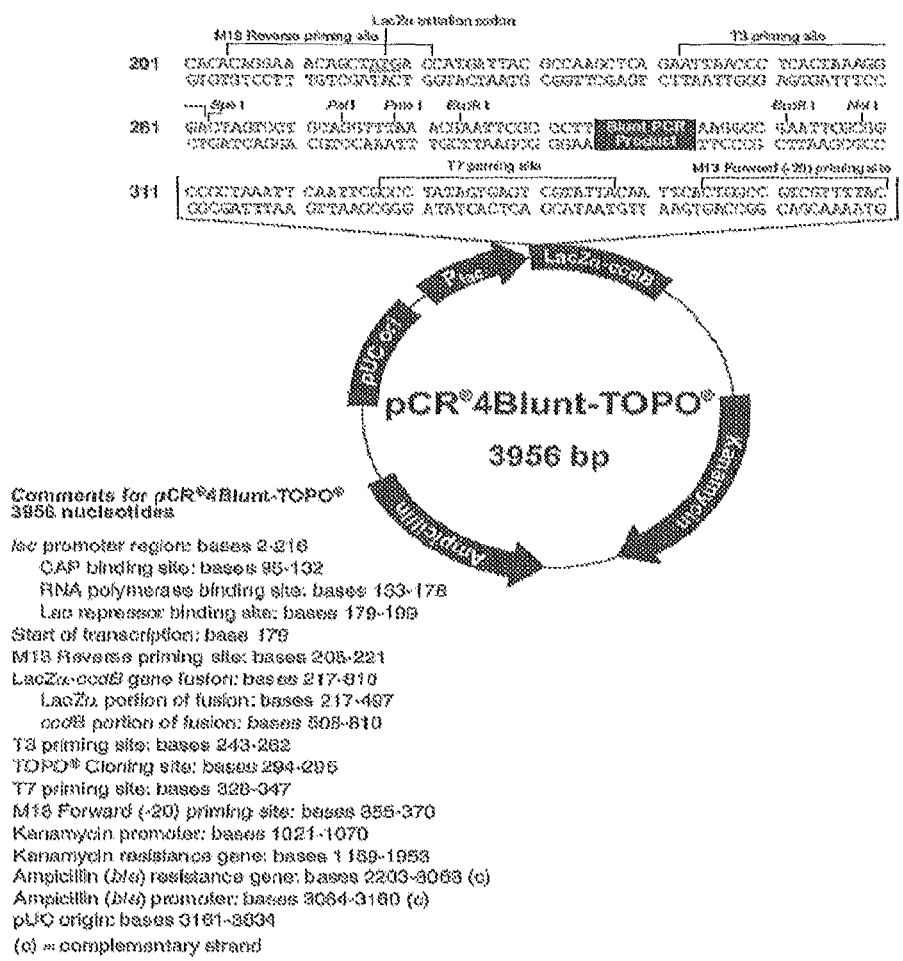
FIG. 2b is a table summarizing that PPDK-encoding cDNA and gDNA was inserted into pCR$_4$ BLUNT-TOPO using an AvrII and BamHI digest.

The Generation of SAG12 Promoter *Arabidopsis* PPDK Plant Transformation Constructs A series of SAG12 PPDK and PCK expression vectors were generated, as shown in FIG. 3, and then analysed for their ability to increase the expression of PPDK and PCK in transformed plants. In one embodiment, the constructs may encode PCK or a functional variant or fragment thereof, and not PPDK. In another embodiment, the constructs may encode PPDK or a functional variant or fragment thereof, and not PCK. However, in yet another embodiment, the constructs may encode PCK or a functional variant or fragment thereof, and PPDK or a functional variant or fragment thereof. Firstly, genomic DNA for the *Arabidopsis thaliana* PPDK gene was isolated, as described below.

Isolation of Genomic DNA

Genomic DNA (gDNA) from *Arabidopsis thaliana* ecotype Columbia 0 was extracted from leaves using the DNeasy Plant Mini Kit (Qiagen) according to the recommended protocol. Genomic DNA was used as a template for PCR reactions as described below using primer sequences summarized in Table 1.

TABLE 1

Primer sequences

| Primer | Sequence | SEQ ID No. |
|---|---|---|
| AtCytFWD-AvrII | AAT CCT AGG ATG ATG CAG CGA GTA TTC ACC | 1 |
| AtCytREV-BamHI | AAT GGA TCC TCA TGC AAC AAC TAC TTG AGC AGC | 2 |
| AtPPDKexon15FWD | CCT CGC CAA AGG AAT CTT AC | 7 |
| AtPPDKSeqF1 | CTT GGC TTG AAC GAC CAA GTC | 3 |
| AtPPDKSeqF2 | GGT TGC AGG GAT AGG AAC ACC | 4 |
| AtPPDKSeqR1 | CGT CTG ATT GCA TCA GCC CAG | 5 |
| AtPPDKSeqR2 | CCT GAG GAG TTC CTA CAA GTG | 6 |

TABLE 1-continued

Primer sequences

| Primer | Sequence | SEQ ID No. |
|---|---|---|
| BNP-1271F | TGC CTG CTT GCC GAA TAT C | 10 |
| BNP-1291TV | CAG AAA AGC GGC CAT TTT CCA CCA | 12 |
| BNP-1334R | CCG GCC CAC AGT CGA TGA | 11 |
| BNP-nostREV | CAA GAC CGG CAA CAG GAT TCA | 8 |
| BNP-SAG12FWD | ACC CCA TCT CAG TAC CCT TCT G | 9 |
| NtCyc-184F | CTC AAC CTT CCA CCG TGT GAT | 13 |
| NtCyc-267T | TCT ACG GTG CCA AAT TCG CCG A | 15 |
| NtCyc-316R | ACC GGT GTG CTT CCT CTT GAA | 14 |
| AtPCK-XbaI-FOR | ATTTCTAGAATGTCGGCCGGTAACGGAAATG | 25 |
| AtPCK-SacI-REV | ATTGAGCTCCTAAAAGATAGGACCAGCAGCG | 26 |

Isolation of RNA and Synthesis of cDNA

Total RNA was extracted from 7 day old *Arabidopsis* cotyledons. RNA extractions were performed on ice using RNase-free equipment, and solutions were made using water treated with diethyl pyrocarbonate (DEPC, Sigma-Aldrich). 1 ml DEPC was added per 1 litre water, the mixture was stirred overnight in a fume hood, and then autoclaved. RNA was extracted using TriPure Isolation Reagent (Roche). 200 mg tissue was ground in liquid nitrogen using a mortar and pestle, 1 ml TriPure Isolation Reagent added and the recommended protocol followed. The RNA pellet was resuspended in 20 µl RNA Secure (Ambion) preheated to 60° C. for 10 minutes. The sample was centrifuged at 4° C. for 5 minutes at 13,000 rpm and the supernatant transferred to a clean 1.5 ml microcentrifuge tube to remove contaminating debris.

Quantity and purity of the RNA were determined spectrophotometrically by taking readings at 260 and 280 nm (Maniatis et al., 1982, Molecular cloning: a laboratory manual. Cold Spring Harbor Laboratory) using an Eppendorf Biophotometer spectrophotometer. The RNA was also examined using agarose gel electrophoresis using 1.5% (w/v) agarose (Melford Laboratories) in 0.5×TBE. Samples were suspended in 1× RNA sample buffer, and subjected to electrophoresis at 80 V using 0.5×TBE as running buffer. RNA sample buffer at 4× working concentration contained 0.002% (w/v) ethidium bromide (Sigma-Aldrich), 2×TBE (2× Tris-Borate-EDTA Buffer (2×TBE) contained 180 mM Tris-HCl, 180 mM boric acid and 8 mM EDTA pH 8.3, 13% Ficoll 400 (Sigma-Aldrich), 0.01% bromophenol blue and 7 M urea (Ficher Scientific).

Reverse transcription of RNA to synthesise cDNA was performed using 2 µg RNA, 1 µg Oligo dT(15) primer (Roche), 1× Moloney Murine Leukaemia Virus (MMLV) buffer (Promega), 0.4 mM dNTPs (Bioline), 40 units Recombinant RNasin Ribonuclease Inhibitor (Promega), 200 units MMLV Reverse Transcriptase (Promega) and nuclease-free water to a final volume of 25 µl. The sample was incubated at 42° C. for 1 hour.

Amplification of *Arabidopsis* PPDK

The genomic and cDNA versions of the gene encoding the cytosolic isoform of PPDK were amplified from the genomic or cDNA templates by PCR using a forward primer (AtCyt-FWD-AvrII. SEQ ID No. 1) containing the AvrII restriction site and a reverse primer (AtCytREV-BamHI. SEQ ID No. 2) containing the BamHI restriction site, which are shown in Table 1. The PCR reaction mixture contained 1×HF buffer (NEB), 2 mM magnesium chloride ($MgCl_2$, NEB), 0.5 mM dNTPs (Bioline), 100 ng template (cDNA or genomic DNA), 0.5 µM each primer and 1 unit Phusion High-Fidelity DNA Polymerase (NEB). Thermal cycling was performed using a Techne Thermal Cycler with an initial denaturation step of 98° C. for 30 seconds, followed by 30 cycles of 98° C. for 10 seconds, 55° C. for 30 seconds and 72° C. for 2 minutes, with a final extension step of 72° C. for 5 minutes.

Once the cDNA and gDNA of *Arabidopsis* PPDK had been isolated/prepared, it was then used to generate various constructs, using the protocol that is summarized in FIG. 1. The cDNA and genomic DNA forms of the cytosolic isoform of *Arabidopsis* PPDK were fused to the senescence-induced SAG12 promoter in a pBNP vector, in order to overexpress PPDK during senescence.

(a) PCR amplification of cDNA and genomic DNA forms of cytosolic isoform of *Arabidopsis* PPDK using primers containing AvrII and BamHI restriction sites, generating 2.4 and 4.3 kb products respectively.

(b) Insertion into cloning vector pCR 4Blunt-TOPO. The PPDK inserts were sequenced in their entirety, and found to be identical to expected sequences.

(c) Restriction endonuclease digestion of cloning vector and destination vector pBNP with AvrII and BamHI.

(d) Ligation into BNP and agarose gel showing DNA fragments produced by restriction endonuclease digestion of constructs with AvrII and BamHI. Expected band sizes were 14.8 kb and 2.4 kb for the cDNA construct, and 14.8 kb and 4.4 kb for the gDNA construct.

(e) Constructs introduced into *Arabidopsis* ecotype Columbia 0 by *Agrobacterium*-mediated transformation. Constructs were sequenced across ligation sites. The gene nptII encodes neomycin phosphotransferase, conferring kanamycin resistance in plants. LB and RB: left and right borders respectively of T-DNA; nos Pro: nopaline synthase promoter; nos t: nopaline synthase terminator; SAG12 Pro: promoter of *Arabidopsis* SAG12 gene.

Referring to FIG. 1, the generation of the constructs will now be described in detail below:

Cloning into the pCR4Blunt-TOPO Vector

PCR products were examined using agarose gel electrophoresis using 1% (w/v) agarose, 0.5 µg ml$^{-1}$ ethidium bromide (Sigma-Aldrich) in 0.5×TBE. Samples were suspended in 1×DNA sample buffer (DNA Sample Buffer at 6× working concentration contained 50 mM Tris(hydroxymethyl) aminomethane (Tris-HCl, Melford Laboratories), 60% glycerol and 0.25% (w/v) bromophenol blue (Sigma-Aldrich) and subjected to electrophoresis at 80V using 0.5×TBE as running buffer.

The PPDK cDNA band of 2.6 kb and the PPDK genomic DNA band of 4.4 kb were purified using the QIAQuick PCR Purification Kit (Qiagen) according to the recommended protocol, and eluted using 30 µl molecular biology grade water (BDH Laboratory Supplies). PCR products were ligated (blunt-end) into the pCR4 Blunt-TOPO vector (Invitrogen) according to the recommended protocol. The cloning reaction (2 µl) was transformed into 50 µl sub-cloning efficiency DH5a *E. coli* (Invitrogen) following the recommended procedure. Transformed *E. coli* cells were grown at 37° C. overnight on Luria-Bertani (LB) agar (Luria Bertani Broth (LB broth) contained 10 gl$^{-1}$ Bacto-Tryptone (BD), 5 gl$^{-1}$ Bacto-Yeast Extract (Oxoid) and 85 mM sodium chloride (Fisher Scientific). The pH was adjusted to 7.0 with 10 M sodium hydroxide prior to autoclaving. LB agar was made by adding 1.5% (w/v) agar (BD) to LB broth containing 50 µg ml$^{-1}$ kanamycin (Melford Laboratories).

*E. coli* colonies were screened by PCR using 1×$NH_4$ buffer (Bioline), 2.5 mM $MgCl_2$ (Bioline), 0.5 mM dNTPs (Bioline), 0.3 µM each primer (AtCytFWD-AvrII and AtCytREV-BamHI), i.e. SEQ ID No's 1 & 2, and 0.5 units BioTaq NA Polymerase (Bioline). Thermal cycling was performed with an initial denaturation step of 95° C. for 5 minutes, followed by 30 cycles of 95° C. for 30 seconds, 55° C. for 30 seconds and 72° C. for 4 minutes 30 seconds, with a final extension step of 72° C. for 5 minutes. PCR products were examined using 1% (w/v) agarose gel electrophoresis as above. Colonies containing the desired insert were grown overnight in a shaking incubator at 37° C. in 5 ml LB broth containing 50 µg ml$^{-1}$ kanamycin. Plasmid DNA was extracted using the QIAPrep Spin Miniprep Kit (Qiagen) according to the recommended protocol. DNA was digested with 10 units BamHI (NEB1) in 1× BamHI Buffer at 37° C. for 1 hour. Digests were examined using 1% (w/v) agarose gel electrophoresis as above. Inserts in plasmids showing the correct restriction enzyme digest pattern were sequenced using the primers AtCytFWD-AvrII (SEQ ID No.1), AtPPDKSeqF1 (SEQ ID No. 3), AtPPDKSeqF2 (SEQ ID No. 4), AtPPDKSeqR1 (SEQ ID No. 5), AtPPDKSeqR2 (SEQ ID No. 6) and AtCytREV-BamHI (SEQ ID No.2), shown in Table 1, using a 3730 DNA Analyzer (Applied Biosystems). Sequences were analysed in BioEdit (Ibis Biosciences).

These constructs were named TOPO-PPDKcDNA and TOPO-PPDKgDNA, and are illustrated in FIGS. 2*a* and 2*b*.

Cloning of pBNP Constructs

PPDK was ligated into the BNP1380000001 binary vector under the control of the senescence-induced promoter SAG12. The SAG12-containing backbone plasmid, BNP1380000001, is based on pBINPLUS (F. A. van Engelen et al. Transgenic Research (1995) 4, 288-290), and is illustrated in FIG. 3*a*. First, *E. coli* colonies carrying TOPO-cDNA or TOPO-gDNA were used to inoculate 25 ml LB broth containing 50 µg ml$^{-1}$ kanamycin. These cultures were incubated overnight in a shaking 37° C. incubator and plasmid DNA was extracted using the Plasmid Midi Kit (Qiagen) according to the recommended protocol. The pBNP1380000001 vector was purified from a 100 ml culture containing 50 µml$^{-1}$ kanamycin using the Plasmid Midi Kit.

These plasmids were then subjected to digestion by the restriction enzymes AvrII and BamHI. Digest reactions were incubated overnight at 37° C. and contained either 2 µg DNA (BNP) or 4 µg DNA (TOPO-PPDKcDNA and TOPO-PPDKgDNA), 1×Buffer 2, 10 units AvrII and 10 units BamHI. Samples were separated by crystal violet agarose gel electrophoresis (Rand, 1996, Crystal violet can be used to visualize DNA bands during gel electrophoresis and to improve cloning efficiency. Elsevier Trends Journals Technical Tips Online.) using 0.8% (w/v) agarose, 0.5×TBE and 25 µM crystal violet (Hopkin and Williams) subjected to electrophoresis at 50V for approximately 2 hours using crystal violet sample buffer (250 µM crystal violet (Hopkin and Williams) and 30% (w/v) sucrose (Fisher Scientific)), and 0.5×TBE containing 25 µM crystal violet as running buffer. Gel band extraction using the QIAQuick Gel Extraction Kit (Qiagen)

according to the recommended protocol was used to extract the 14.4 kb BNP, 2.6 kb PPDK cDNA and 4.4 kb PPDK genomic DNA fragments. Fragments were inspected and quantified relative to HyperLadder I (Bioline) using 1% agarose gel electrophoresis using ethidium bromide.

Due to the similar sizes of the genomic DNA fragment (4.4 kb) and the TOPO backbone (3.9 kb), the gel-extracted genomic DNA fragment was phosphatase-treated to prevent ligation to any contaminating TOPO backbone. Shrimp Alkaline Phosphatase (SAP, 1 unit, Roche) was added to 1 µg gel-extracted genomic DNA fragment in 1× Dephosphorylation Buffer (Roche) and the reaction incubated at 37° C. for 30 minutes then inactivated at 65° C. for 10 minutes. Ligation reactions were performed using either the cDNA or the genomic DNA fragment with the digested BNP in a 10:1 molar ratio, 1× ligation buffer (NEB) and 1 unit T4 DNA ligase (NEB). Ligation reactions were incubated overnight at 16° C. and 2 µl used to transform library-efficiency DH5_E. coli (Invitrogen) according to the recommended protocol.

Transformed E. coli were transferred onto LB agar containing 50 µml$^{-1}$ kanamycin and incubated overnight at 37° C. E. coli colonies were screened by PCR using 1×NH$_4$ buffer, 2.5 mM MgCl$_2$, 0.5 mM dNTPs, 0.3 µM each primer (AtPPDKexon15FWD (SEQ ID No. 7) and BNPnostREV (SEQ ID No. 8), shown in Table 1, and 0.5 units BioTaq DNA Polymerase. Thermal cycling was performed with an initial denaturation step of 95° C. for 5 minutes, followed by 30 cycles of 95° C. for 30 seconds, 55° C. for 30 seconds and 72° C. for 3 minutes, with a final extension step of 72° C. for 5 minutes. PCR products were examined using 1% (w/v) agarose gel electrophoresis as above. Colonies containing the desired insert were grown overnight in a shaking incubator at 37° C. in 5 ml LB broth containing 50 µml$^{-1}$ kanamycin. Plasmid DNA was extracted using the QIAPrep Spin Miniprep Kit according to the recommended protocol. DNA was digested with 10 units BamHI and 10 units StuI in 1× BamHI Buffer and at 37° C. for 1 hour before being subjected to 1% (w/v) agarose gel electrophoresis as above. One colony each resulting from the cDNA and genomic DNA ligations showing the correct restriction enzyme digest pattern were selected and sequenced using the primer BNP-SAG12FWD (SEQ ID No. 9), shown in Table 1, as described above.

These constructs were named BNP-PPDKcDNA and BNP-PPDKgDNA, and are illustrated in FIGS. 3a and 3b.

Example 2

Transformation of *Arabidopsis thaliana* with BNP-PPDKcDNA and BNP-PPDKgDNA

*Agrobacterium tumefaciens* strain GV3101-R was transformed by electroporation using the following plasmids: BNP-PPDKcDNA, and BNP-PPDKgDNA, shown in FIG. 3, the preparation of which has been described in Example 1.

Electrocompetent *Agrobacterium* was made from cultures of LB broth containing 25 mg l$^{-1}$ rifampicin (Sigma-Aldrich), grown at 30° C. and with an optical density at 600 nm of 0.4 to 0.6, measured using an Eppendorf Biophotometer spectrophotometer. Cultures of 500 ml were centrifuged at 4000 g for 15 minutes, the supernatant discarded and the cells resuspended in 500 ml cold 10% glycerol (Fisher Scientific). Centrifugation and resuspension were repeated using 250 ml glycerol, followed by 10 ml and finally 2 ml glycerol. Cells were aliquoted into 50 µl aliquots, flash frozen in liquid nitrogen and stored at −80° C. Electroporation was performed using a BioRad Gene Pulser. Plasmid DNA (200 ng) was added to 50 µl *Agrobacterium* cells as above in a pre-chilled electroporation cuvette (Gene Pulser Cuvette, BioRad) and the cells were incubated on ice for 5 minutes. The cuvette was subjected to electroporation using a pulse of 2.5 mV, 400 ohm resistance and 25 µF capacitance and 1 ml SOC (Super Optimal Broth, Catabolite Repression contained 20 g/l Bacto-Tryptone, 5 g/l Bacto-Yeast Extract, 85 mM sodium chloride, and 250 mM potassium chloride. 10 M sodium hydroxide was used to adjust to pH 7.0 prior to autoclaving. Before use, sterile magnesium chloride was added to a final concentration of 10 mM and sterile glucose (Fisher Scientific) was added to a final concentration of 20 mM. The cells were incubated in a shaking incubator at 30° C. for 2 hours before being transferred onto LB agar containing 50 µg ml$^{-1}$ kanamycin and 50 µg ml$^{-1}$ rifampicin.

After incubation at 30° C. for 2 days, colonies were screened by PCR and then by restriction enzyme digestion. Colonies positive for the PCR screen and showing the expected restriction digest pattern were inoculated into 5 ml LB broth containing 50 µml$^{-1}$ kanamycin and 50 µml$^{-1}$ rifampicin and incubated in a shaking incubator at 30° C. overnight. The following day, 600 µl of this culture was used to inoculate 500 ml LB broth as above, and incubated in a shaking incubator at 30° C. for 30 hours before being used for floral dipping.

*Arabidopsis* plants were used for floral dipping at 4 weeks old. All constructs were transformed into wild-type ecotype Columbia 0. *Agrobacterium* cultures prepared as described above were centrifuged at 4° C. for 15 minutes at 5,000 g and the cell pellets resuspended in 250 ml sterile 5% sucrose (Fisher Scientific) solution (w/v) and 0.05 Silwett L-77 (OSi Specialties). Plants were immersed in the cell suspension for approximately 10 seconds with gentle agitation, before being covered in clingfilm and kept away from direct light for 24 hours. Following this, plants were returned to the normal growth regime and seed was harvested.

Selection of Transgenic *Arabidopsis thaliana*

Seed from transformed plants was selected on 50 µg ml$^{-1}$ kanamycin (Dufecha Biochemie) according to Harrison et al. (2006), Plant Methods, 2, 19. T1 plants showing antibiotic resistance were grown to seed and self-pollinated. The seed was selected as above and T2 lines showing a 3:1 resistant: non-resistant ratio were chosen as carrying a single copy of the transgene. These plants were again self-pollinated and selected as above. T2 lines that produced 100% resistant offspring (T3) were chosen as being homozygous and were used for all experiments. Mendelian genetics was used to select T2 generation plants that were homozygous for the transgene, and contained a single transgene copy. Five independent single-insert homozygous lines were selected each for plants transformed with SAG12-PPDKcDNA and SAG12-PPDKgDNA.

Example 3

Transformation of *Nicotiana tabacum* with BNP-PPDKcDNA and BNP—PPDKgDNA

Electrocompetent *Agrobacterium tumefaciens* strain LBA4404 was transformed by electroporation as described in Example 2 using the plasmids BNP, BNP-PPDKcDNA and BNPPPDKgDNA. Following electroporation, 1 ml LB broth was added to electroporated cells, which were then incubated in a shaking incubator at 28° C. for 2 hours before being transferred onto LB agar containing 50 µg ml$^{-1}$ kanamycin and 100 µg ml$^{-1}$ spectinomycin (Sigma-Aldrich). After incubation at 28° C. for 2 days one colony was used to inoculate 50 ml LB broth containing 50 µg ml$^{-1}$ kanamycin and 100

µml$^{-1}$ spectinomycin. This culture was incubated in a shaking incubator at 28° C. for 3 days. Plasmid DNA was extracted and analysed by restriction enzyme digest, and 50 µl culture was used to inoculate 50 ml LB broth containing 50 µml$^{-1}$ kanamycin and 100 µg ml$^{-1}$ spectinomycin. This culture was incubated in a shaking incubator at 28° C. overnight.

*Nicotiana tabacum* cultivars Burley 21 and K326 were grown from seed and the youngest leaves were excised from 8 week old plants and sterilised in 8% (v/v) Domestos thick bleach (Domestos) for 10 minutes before being rinsed in sterile distilled water. A number 6 cork borer was used to punch leaf discs, which were then placed into 25 ml of *Agrobacterium* culture for 2 minutes. Leaf discs were then placed underside down onto MS medium containing 2.2 µM 6-benzylaminopurine (BAP) and 0.27 µM a-naphthaleneacetic acid (NAA). These were placed in a growth room at 22° C. for two days. Leaf discs were then transferred to selective MS medium as above containing 500 µg ml$^{-1}$ clarofan (Roussel Laboratories) (non-cocultivated controls) or 500 µml$^{-1}$ clarofan and 100 µml$^{-1}$ kanamycin. Leaf discs were transferred to fresh selective MS medium as above every 14 days for 6 weeks. Callus and shoot clumps were then removed from discs and placed onto LS medium containing 0.5 µM BAP, 500 µg ml$^{-1}$ clarofan and 100 µml$^{-1}$ kanamycin. After 2 weeks shoots were transferred to 150 ml jars with LS medium containing 0.5 µM BAP, 500 µg ml$^{-1}$ clarofan and no kanamycin.

After a subsequent 3 weeks, the dominant shoot was transferred to LS medium containing 250 µg ml$^{-1}$ clarofan and no BAP or kanamycin. After another 3 weeks shoots were further cleaned by transferring the shoot tip to LS medium with no antibiotics or BAP. When sufficient roots had generated, plants were transferred to soil in greenhouses.

Selection of Transgenic *Nicotiana tabacum*

Quantitative PCR (Q-PCR) was used to quantify transgene copy number in T0 and T1 plants. Where possible, single insert T0 and homozygous T1 plants were chosen for analysis. For transgene detection, primers BNP-1271F (SEQ ID No. 10) and BNP-1334R (SEQ ID No. 11) were used, as shown in Table 1, and the Vic/TAMARA-labelled probe BNP1291TV (SEQ ID No. 12) was used, annealing to the nptII transgene. For internal quantitation, primers NtCyc-184F (SEQ ID No. 13) and NtCyc-316R (SEQ ID No. 14) were used, and the FAM/TAMARA-labelled probe NtCyc-267T (SEQ ID No. 15) was used, annealing to the endogenous gene encoding cyclophilin. Quantitation was by the Comparitive Ct method (ΔΔCt method, Bubner & Baldwin (2004), Plant Cell Reports, 23, 263-271). Reaction mixtures contained 1× Universal Master Mix (ABI), 0.9 µM each primer, 0.2 µM each probe (using separate reactions for BNP and NtCyc primers and probes) and approximately 500 ng genomic DNA template extracted from leaf tissue using the Dneasy Plant Mini Kit (Qiagen) according to the recommended protocol. Thermal cycling was performed in a 7900HT Fast Real-Time PCR System (Applied Biosystems) with an initial denaturation step of 95° C. for 10 minutes, followed by 40 cycles of 95° C. for 15 seconds and 60° C. for 1 minute. Data were analysed using the supplied SDS2.2 software (Applied Biosystems).

Following regeneration in tissue culture of transformed T0 generation K326 and Burley 21 tobacco, quantitative PCR (Q-PCR) was used to select plants carrying a single copy of the transgene. Single-insert plants were selected to reduce the possibility of transgene silencing. Q-PCR was performed using oligonucleotides complementary to the nptII transgene, encoding neomycin phosphotransferase. This gene was present between the left and right borders of the T-DNA transferred into the plant genome in constructs pBNP, BNP-PPDKcDNA and BNP-PPDKgDNA. Plants transformed with pBNP only served as empty vector controls, to ensure that regeneration through tissue culture was consistent between plants transformed with the empty vector and those transformed with the vectors containing PPDK coding sequence. Following regeneration and Q-PCR checks to confirm that successful transformation had occurred, these plants were discarded.

For each construct (SAG12-PPDKcDNA and SAG12-PPDKgDNA) and each cultivar (K326 and Burley 21), six plants were selected. It was not possible to select only single-insert plants, so where six single-insert plants were not available, plants with the lowest copy number possible were selected. These plants were self-pollinated and the seed was harvested.

For each selected T0 plant, 14 offspring were grown and Q-PCR was repeated to select homozygous plants. Use of homozygous plants should ensure stability of the transgene in future generations. For each T0 parent, four offspring carrying the transgene were selected. However, it was not always possible to select homozygous offspring for every T0 parent. Where parental copy number was higher than two, plants with lower copy numbers were selected to reduce the possibility of transgene silencing, and also to simplify the selection of homozygotes from the T2 generation, if necessary. In this way, for each construct and each cultivar four biological replicates (siblings) from five independent lines were selected with low transgene copy numbers for all further experiments.

Example 4

Detection and Quantification of PPDK Protein in Transformed *Arabidopsis* Plants Protein Extraction

*Arabidopsis* leaf tissue (100 mg) was ground under liquid nitrogen in a 1.5 ml microcentrifuge tube using a micropestle and 400 µl extraction buffer (Potassium Phosphate Buffer (plus Protease Inhibitor Cocktail (PIC, Sigma)) was added. Protein concentration was determined by Bradford assay (Jones et al., 1989, Journal of Chemical Ecology, 15, 979-992) using Bio-Rad Protein Assay Reagent (Bio-Rad) according to the recommended protocol.

Polyacrylamide Gel Electrophoresis

Proteins were separated by polyacrylamide gel electrophoresis (PAGE) in a resolving gel containing 10% (v/v) acrylamide (37.5:1 acryl:bis acryl, Severn Biotech Ltd), 50% (v/v) Immunoblot Resolving Buffer (see Section 2.10), 0.05% (w/v) ammonium peroxodisulphate (APS, AnalaR) and 0.05% (v/v) N,N,N'N' tetramethylethylenediamine (TEMED, Severn Biotech Ltd). The stacking gel contained 5% acrylamide as above, 50% (v/v) Immunoblot Stacking Buffer, 0.06% (w/v) APS and 0.1% (v/v) TEMED. Electrophoresis was performed on 20 µg total protein extracted using 1× Immunoblot Sample Buffer (66 mM Tris-HCl, 10% (v/v) glycerol, 0.7 mM SDS, 0.7 M β-mercaptoethanol (BDH Laboratory Supplies) and 0.05% (w/v) bromophenol blue and Immunoblot Running buffer (25 mM Tris-HCl, 0.29 mM glycine (Fisher Scientific) and 3.5 mM SDS at a current of 70 mA for 1 hour 30 minutes.

Duplicate gels were run simultaneously. One was used for immunoblot analysis (described hereinafter) and the second stained using GelCode Blue Safe Protein Stain (Thermo Scientific) according to the recommended protocol. Gel Drying Film (Promega) was used to dry stained gels.

Immunoblot Analysis

Proteins from the gel for immunoblot analysis were transferred onto a Protan BA83 Cellulose Nitrate Membrane (Schleicher and Schuell) using Protean Extra-Thick Blot Paper (Bio-Rad) and Immunoblot Transfer Buffer (48 mM Tris-HCl, 39 mM glycine, 1.3 mM SDS and 20% (v/v) methanol (Fisher Scientific)) in a Semi-Dry Blotter (Bio-Rad) at 15 V for 1 hour. Ponceau Stain (0.5% (w/v) Ponceau S (Fluka) and 1% (w/v) glacial acetic acid (Fisher Scientific)) was applied to the membrane after blotting to verify protein transfer, and the membrane was then rinsed in distilled water.

Blocking buffer for PPDK immunoblot analysis was made fresh each day using 1% (w/v) dried skimmed milk powder (Marvel) and 0.1% (v/v) polyoxyethylene sorbitan monolaurate (TWEEN 20, Sigma-Aldrich) in phosphate buffered saline (PBS: 1.5 mM potassium dihydrogen orthophosphate (KH2PO4, AnalaR), 8.1 mM disodium hydrogen orthophosphate, 2.7 mM potassium chloride and 137 mM sodium chloride. Hydrochloric acid was used to adjust to pH 7.4. Membranes were incubated in blocking buffer at room temperature on a shaker for 1 hour. Primary hybridisation was performed using a 1:10,000 dilution of rabbit anti-PPDK antibody (Chris Chastain, Minnesota State University) followed by 3 washes of 5 minutes each in blocking buffer. Secondary hybridisation was performed using a 1:1000 dilution of Donkey Anti-Rabbit Biotinylated Whole Antibody (GE Healthcare) followed by 3 washes as above. Tertiary hybridisation was performed using a 1:1000 dilution dilution of Streptavidin-Biotinylated Horse Radish Peroxidase Complex (GE Healthcare) followed by 3 washes of 5 minutes each in PBS containing 0.1% (v/v) TWEEN 20.

Membranes were then rinsed 3 times in distilled water. Detection was performed using Western Lightning Chemiluminescence Reagent (Enhanced Luminol, Perkin Elmer) according to the recommended protocol.

Referring to FIG. 4, there is shown the selection of transgenic SAG12-PPDK *Arabidopsis thaliana* cell lines by Western blot. Protein was extracted from leaf tissue of eight week old *Arabidopsis* wild-type, ΔPPDK SAG12-PPDKcDNA and SAG12-PPDKgDNA plants, and subjected to immunoblot analysis to select lines expressing higher levels of PPDK. Recombinant maize PPDK (30 μg) was used as a positive control. PPDK was not detected in wild-type or PPDK mutant plants (ΔPPDK). SAG12-PPDKgDNA plants were expressing higher levels of PPDK than SAG12-PPDKcDNA. All subsequent analysis was performed on the five SAG12-PPDKgDNA lines.

PPDK was undetectable in wild-type and ΔPPDK plants, was detectable at low levels in some SAG12-PPDKcDNA plants, and was detectable in all SAG12-PPDKgDNA lines. In three of these lines, much higher amounts of PPDK were detected compared to wild-type or SAG12-PPDKcDNA lines. Therefore, the presence of introns appears to have a positive effect on PPDK expression levels, and the SAG12-PPDKgDNA lines were selected for use in all further experiments.

Immunoblots against PPDK were performed on wild-type, ΔPPDK and SAG12-PPDKgDNA plants in order to determine the onset and extent of PPDK accumulation in SAG12-PPDKgDNA plants.

Referring to FIG. 5, there is shown the quantification of PPDK abundance in wild-type, ΔPPDK and five independent SAG12-PPDKgDNA lines from week five onwards. PPDK abundance was calculated as a percentage of wild-type for each time-point from weeks five to nine. Data are shown as mean of these five time-points. Error bars show one SEM. SAG12-PPDKgDNA lines are arranged in order of increasing PPDK abundance. The differences between genotypes were tested using ANOVA (F=4.775, df=6, p=0.001). Lines significantly different to wild-type were G12.3 (p=0.005) and G16.1 (p=0.004).

Proteins were extracted from leaf tissue harvested at weekly intervals from three weeks to nine weeks after sowing. PPDK was detected in low amounts in wild-type plants from week five onwards, confirming that the observed increase in transcripts results in an increase in protein abundance. In SAG12-PPDKgDNA plants, onset of PPDK accumulation was also observed at week five, but PPDK abundance is higher than in the wild-type. No PPDK protein was detected at any stage in ΔPPDK plants.

A method to allow quantification of PPDK in leaf protein extracts was also optimized. Different amounts of recombinant maize PPDK protein were subjected to SDS-PAGE and immunoblot analysis. Band intensity was calculated using AlphaEase imaging software and a standard curve constructed. The regression line was calculated using SigmaPlot software which was subsequently used to calculate PPDK amounts in plant leaf samples. Since immunoblot detection levels can vary, it was necessary to include at least three standards on every immunoblot to allow true comparison between different immunoblots. This technique for quantification of PPDK abundance in different extracts was used to select and compare different transgenic lines.

PPDK protein abundance was calculated by reference to the known standards of recombinant maize PPDK protein for at least four biological replicates for each line at each time-point. The analysis showed that PPDK abundance in SAG12-PPDKgDNA was higher than in wild-type from week five onwards. PPDK abundance was calculated as a percentage of wild-type at each time-point from week five onwards for each SAG12-PPDKgDNA line, and the mean taken of these values to quantify PPDK accumulation over the senescence period in each SAG12-PPDKgDNA line. This allowed the SAG12-PPDKgDNA lines to be ordered according to increasing PPDK abundance, as shown in FIG. 5.

Since proteins which accumulate in high amounts in transgenic plants may be subjected to inactivation, the increased protein abundance does not necessarily imply increased enzyme activity. PPDK is reversibly phosphorylated in the dark, resulting in its inactivation. An antibody has been raised against the phosphorylated version of PPDK (Phospho-PPDK), allowing specific detection of the inactive form of PPDK, whereas the antibody used previously (anti-PPDK) detects PPDK regardless of phosphorylation state (Chastain et al., 2002, Plant Physiology, 128, 1368-1378). The anti-PhosphoPPDK antibody was used to detect inactivated PPDK over a time-course from three weeks to nine weeks after sowing, on immunoblots probed initially with anti-PPDK antibody and then stripped and reprobed.

Surprisingly, inactivated PPDK (phosphorylated) was detectable only at very low levels in wild-type plants in a number of immunoblots, and only during the later stages of senescence. In SAG12-PPDKgDNA plants, depending on the time-point inactivated, PPDK was detected at higher levels. However, at time-points soon after onset of increased PPDK abundance, very little or no inactivated PPDK was detected despite high abundance of total PPDK. These results suggest that while some PPDK inactivation could occur in SAG12-PPDKgDNA plants, increased abundance of enzymatically active PPDK is present in SAG12-PPDK plants at least during early stages of senescence.

Example 5

Detection and Quantification of PPDK Protein in Transformed *N. Tabacum* Plants

*N. tabacum* leaf tissue (100 mg) was ground under liquid nitrogen in a 1.5 ml microcentrifuge tube using a micropestle and 400 µl extraction buffer (Overcoat Buffer (PIC)) was added. Protein concentration was determined by Bradford assay (Jones et al., 1989) using Bio-Rad Protein Assay Reagent (Bio-Rad) according to the recommended protocol. Proteins were separated by polyacrylamide gel electrophoresis (PAGE) as described in Example 4. Proteins were analysed and PPDK protein quantified by immunoblot as described for Example 4.

Immunoblots against PPDK were performed on leaf protein extracted from K326 and Burley 21 T1 generation tobacco leaves induced to senesce by detachment and incubation in the dark at 30° C. Senescence was induced in this way so that transgenic lines with highest PPDK abundance could be identified, and other lines discarded, before plants reached maturity. In K326 plants, PPDK was detected in high abundance in three SAG12-PPDKgDNA lines (G4, G8 and G10) and in one SAG12-PPDKcDNA line (C10). In Burley 21 plants, PPDK was abundant in four SAG12-PPDKgDNA lines (G3, G7, G15 and G23), but was not present in as high abundance as in K326 lines. The four lines each for K326 and Burley 21 that had highest PPDK abundance were used for all further analysis. Since highest PPDK abundance was observed almost exclusively in SAG12-PPDKgDNA lines, it appears that introns have a positive effect on PPDK expression.

Referring to FIG. 6, there is shown the selection of SAG12-PPDK K326 and Burley 21 tobacco lines, as follows:

(b) PPDK immunoblot to select transgenic K326 lines. Senescence was induced in green leaves of six week old plants by detachment and dark incubation at 30 C. for three days. Protein was extracted and subjected to immunoblot analysis to select lines expressing higher levels of PPDK. Recombinant maize PPDK (50 µg) was used as a positive control. One representative immunoblot is shown, with one offspring from each parental T0 plant. Plants from parental lines SAG12-PPDKgDNA G4, G8 and G10 and from SAG12-PPDKcDNA line C10 were used for all subsequent analysis. (c) PPDK immunoblot to select transgenic Burley 21 lines, as for K326 in section (b). Plants from parental lines SAG12-PPDKgDNA G3, G7, G15 and G23 were used for all subsequent analysis.

Immunoblots against PPDK were performed on wild-type, zero copy (negative segregant), SAG12-PPDKgDNA K326 SAG12-PPDKcDNA K326 and SAG12-PPDKgDNA Burley 21 tobacco to determine the onset of expression of PPDK and to quantify the degree of PPDK overexpression in the transformed plants. Proteins were extracted from K326 wild-type and transformed plant leaves one (oldest) to eight (young) of three month old plants and immunoblots against PPDK were performed.

Referring to FIG. 7, there is shown the overexpression of PPDK in ripe leaves of K326 tobacco. PPDK abundance was calculated from immunoblots. Data are shown as mean of 10 biological replicates for zero copy plants, and four biological replicates for each SAG12-PPDK line. Error bars show one SEM. SAG12-PPDK lines are arranged in order of increasing PPDK abundance. The difference between genotypes were tested using ANOVA ($F=6.995$, $df=4$, $p=0.001$). Lines significantly different to zero copy plants were G10 ($p=0.006$), G8 ($p=0.003$) and C10 ($p=0.000$).

PPDK abundance was higher in older leaves of wild-type plants, indicating that PPDK is naturally upregulated during senescence in tobacco as well as in *Arabidopsis*. In the transformed K326 plants, PPDK abundance was also higher in older leaves, and was much higher than in wild-type plants. There was also higher abundance of PPDK in younger leaves of transformed lines with highest PPDK abundance. Immunoblots were performed on protein extracted from 'ripe' leaves of zero copy plants (negative segregants) and transformed plants. Ripe leaves are those at a harvestable stage, and are in the later stages of senescence. PPDK abundance was quantified. PPDK abundance was higher in ripe leaves of all four independent transformed lines compared to zero copy plants. Overexpression of PPDK during senescence using the SAG12 promoter was successful for K326 tobacco.

Example 6

Phenotypic Analysis of Transformed *Arabidopsis* Plants

Analysis of *Arabidopsis* Plant Growth

Referring to FIG. 8, it is clearly shown that the overexpression of PPDKgDNA in *Arabidopsis thaliana* generates plants with larger rosettes. Wild-type, ΔPPDK and SAG12-PPDKgDNA plants were photographed at three, five, seven and nine weeks after sowing. SAG12-PPDKgDNA plants were larger than wild-type. There was no discernable difference between PPDK plants and wild-type plants.

Fresh masses of rosette and reproductive tissue were determined using a Mettler Toledo AB104-S balance to the nearest 0.1 mg. Dry mass of rosette tissue was determined from samples freeze dried overnight using an Edwards Super Modulyo Freeze Dryer to the nearest 0.1 mg.

Referring to FIG. 9, there is shown the reproductive tissue mass at week nine. A dose response to PPDK was observed, with lines with higher PPDK abundance having higher reproductive tissue mass. Total reproductive tissue (stems, cauline leaves, flowers and siliques) was weighed. Values are means of three biological replicates. Error bars show one SEM. Transgenic SAG12-PPDKgDNA lines are arranged in order of increasing PPDK abundance. Difference between genotypes was tested using ANOVA ($F=8.062$, $df=6$, $p=0.001$). All SAG12-PPDKgDNA lines were significantly different to wild type (G9.4 $p=0.031$, G5.4 $p=0.000$, G19.2 $p=0.000$, G12.3 $p=0.001$, G16.1 $p=0.001$). While the trend is not absolute, lines with higher PPDK abundance tended to have higher reproductive tissue mass. Reproductive tissue as percentage of total plant fresh mass was also calculated, but was not significantly different for wild-type, ΔPPDK or SAG12-PPDKgDNA plants when tested using ANOVA ($F=0.544$, $df=6$, $p=0.767$, data not shown).

However, the proportion of reproductive tissue as a percentage of total plant mass was unchanged, suggesting that the plant as a whole was bigger and that resource allocation between vegetative and reproductive tissue was unchanged. Total plant fresh mass and reproductive tissue mass were also measured in ΔPPDK plants, and were not significantly different to wild-type. Rosette dry mass was also measured, and as for total plant fresh mass and reproductive tissue mass, SAG12-PPDKgDNA plants were found to have significantly higher mass than wild-type.

Referring to FIG. 10, there is shown total plant fresh mass (rosette plus reproductive tissue) of wild-type and SAG12-PPDgDNA plants from weeks three to nine after sowing. Data are shown as mean of three biological replicates for wild-type, and 15 biological replicates (three plants each for five independent lines) for SAG12-PPDKgDNA. Error bars show one SEM. Wild-type and SAG12-PPDKgDNA total plant masses were compared using a student's t-test at each timepoint. Rosette mass was significantly higher in SAG12-PPDKgDNA plants at week nine (p=0.032).

The difference was not significant prior to onset of PPDK overexpression due to the SAG12 promoter at week five. All five independent SAG12-PPDKgDNA lines had increased rosette dry mass. A dose response to PPDK abundance was observed as for reproductive tissue mass, with lines with higher PPDK content having higher mass. Rosette dry mass was also measured in ΔPPDK plants, and was not significantly different to wild-type plants.

Determination of *Arabidopsis* Leaf Surface Area

Surface area of the rosette was determined by sampling a single mature leaf, usually leaf 10, determining the mass of the leaf and of the whole rosette as above and photographing the leaf alongside a ruler. The surface area of the leaf was measured using ImageJ software (National Institutes of Health), and the surface area of the whole rosette calculated from this.

Rosette surface area was increased in SAG12-PPDKgDNA plants following onset of PPDK overexpression. While surface area was significantly larger in SAG12-PPDKgDNA plants at weeks six and seven, by weeks eight and nine surface area was not significantly different from wild-type. This large decrease in surface area could be due to increased remobilisation of nutrients in SAG12-PPDKgDNA plants compared to wild-type. Surface area in ΔPPDK plants was not significantly different to wild-type plants.

Determination of Chlorophyll Concentration

Chlorophyll content was measured in relative units using a CCM-200 hand-held chlorophyll meter (Opti-Sciences).

Fluorescence Measurement of *Arabidopsis*

The FV/FM ratio was measured using a Hansatech FMS2 fluorometer. Leaves were dark adapted using leaf clips, provided by the manufacturer, overnight prior to measurement. To determine whether onset of senescence was altered in SAG12-PPDKgDNA or ΔPPDK plants relative to wild-type plants, FV/FM ratios were measured. FV/FM is an estimate of the quantum efficiency of Photosystem II, and declines when photoinhibition occurs. It is a useful measure of the onset of senescence, since decline in photosynthesis occurs early in senescence, before a decline in chlorophyll content is detected. FV/FM was measured over a timecourse from four weeks (when leaves become large enough to measure FV/FM) to nine weeks after sowing. In wild-type, SAG12-PPDKgDNA and ΔPPDK plants, FV/FM was maximal at week seven and subsequently declined, indicating that timing of onset of senescence was the same in all three genotypes. However, in SAG12-PPDKgDNA plants FV/FM was significantly higher than wild-type at week eight, indicating prolonged photosynthetic activity in the later stages of senescence.

Nitrogen Content

Tissue for nitrogen analysis was freeze dried using an Edwards Super Modulyo Freeze Dryer. *Arabidopsis* leaf tissue (25 mg) or tobacco leaf tissue (100 mg) was packaged in nitrogen-free weighing paper (Elementar Analysensysteme GmbH). A Rapid N III Nitrogen Analyzer (Elementar Analysensysteme GmbH) was used to measure nitrogen content as a percentage of dry weight, using the recommended settings. Aspartic acid (Sigma-Aldrich) was used as a standard. Leaf nitrogen content was measured in *Arabidopsis* wild-type, SAG12-PPDKgDNA and ΔPPDK plants over a timecourse from three to nine weeks after sowing.

Referring to FIG. 11, there is shown the nitrogen content in leaves of wild-type, ΔPPDK and SAG12-PPDKgDNA plants at week seven. Data are shown as mean of eight biological replicates for wild-type and ΔPPDK and four biological replicates for each SAG12-PPDKgDNA line. Error bars are one SEM. SAG12-PPDKgDNA lines are arranged in order of increasing PPDK abundance. The difference between genotypes was tested using ANOVA (F=6.047, df=6, p=0.000). ΔPPDK plants and all SAG12-PPDKgDNA lines were significantly different to wild type (ΔPPDK p=0.004, G9.4 p=0.000, G5.4 p=0.000, G19.2 p=0.001, G12.3 p=0.007, G16.1 p=0.006).

Leaf nitrogen was significantly lower in all five independent SAG12-PPDKgDNA lines compared to wild-type from week seven onwards, supporting the hypothesis that increasing PPDK abundance during senescence could enhance efficiency of nitrogen remobilization. PPDK expression and activity peaked at week six in SAG12-PPDKgDNA plants, which suggests that a time delay occurred between increased PPDK abundance and a measurable decrease in leaf nitrogen, which could be attributed to the time taken to convert protein amino acids to transport amino acids (asparagine and glutamine) and transport them out of the leaf.

Analysis of *Arabidopsis* Seed

Individual seed mass and nitrogen content were measured in seed of wild-type, SAG12-PPDKgDNA and ΔPPDK *A. thaliana* plants.

Referring to FIG. 12, there is shown the nitrogen content of individual seed of wild-type, ΔPPDK and SAG12-PPDK plants. There were significant increases in seed nitrogen content of the SAG12-PPDKgDNA plants. Data are shown as mean of eight biological replicates for wild-type and ΔPPDK and four biological replicates for each SAG12-PPDKgDNA line. Error bars are one SEM. SAG12-PPDKgDNA lines are arranged in order of increasing PPDK abundance. Difference between genotypes was tested using ANOVA (F=6.704, df=6, p=0.000). Lines significantly different to wild-type were G19.2 (p=0.000), G12.3 (p=0.005) and G16.1 (p=0.002). Lines with higher PPDK abundance tend to have higher seed nitrogen mass. Hence, individual seed mass was increased in all five independent SAG12-PPDKgDNA lines relative to the wild-type, and a dose response to PPDK abundance was observed, with plants with higher PPDK abundance having higher seed mass. Total seed harvested from each plant was also weighed, and there was no significant difference between wild-type and SAG12-PPDKgDNA plants, so increased seed size in SAG12-PPDK plants did not compromise total seed harvest.

Free Amino Acid Content of *Arabidopsis* Leaf Tissue

Leaf tissue (100 mg) was ground under liquid nitrogen in a 1.5 ml microcentrifuge tube using a micropestle (Eppendorf) and 300 μl sterile deionised water was added. Samples were subjected to centrifugation at 13,000 rpm at 4° C. for 5 minutes. Protein concentration was determined by Bradford assay (Jones et al., 1989) using Bio-Rad Protein Assay Reagent (Bio-Rad) according to the recommended protocol. Samples were prepared for amino acid analysis using the EZfaast Amino Acid Sample Testing Kit (Phenomenex) according to the recommended protocol. Samples were resuspended in 10 mM ammonium formate (BDH laboratory supplies) in 50% sterile distilled water and 50% ultra grade methanol (Romil).

Samples were then subjected to liquid chromatography-mass spectrometry (LC-MS) using a Q Trap LC/MS/MS (Applied Biosystems/MDS SCIEX) with an EZfaast 250×3.0 mm AAA-MS column (Phenomenex) and 10 mM ammonium formate in 50% (v/v) sterile distilled water and 50% (v/v)

ultra grade methanol as the mobile phase. The mass spectrometer was used in positive ion mode with conditions as recommended in the EZfaast Kit (Phemonenex). Results were analysed in the supplied Analyst software (Applied Biosystems/MDS SCIEX).

Total free amino acid content was measured in leaves of wild-type, SAG12-PPDKgDNA and ΔPPDK *Arabidopsis* plants over a timecourse from weeks three to nine after sowing.

Referring to FIG. 13, there is shown the total free amino acid content is increased in leaves of *Arabidopsis* overexpressing PPDK. Data are shown as mean of six biological replicates for wild-type and ΔPPDK and four biological replicates for each SAG12-PPDKgDNA line. Error bars are one SEM. SAG12-PPDKgDNA lines are arranged in order of increasing PPDK abundance. All five SAG12-PPDKgDNA lines have higher total amino acid content than the wild-type, but variation is high and the difference was not significant when tested using ANOVA (F=1.314, df=6, p=0.289).

In SAG12-PPDKgDNA plants, total free amino acid content was significantly higher than in wild-type plants at week seven, the same time at which leaf nitrogen content becomes significantly lower than wild-type, and one week after maximum PPDK abundance in leaves of SAG12-PPDKgDNA plants. The increase occurred in all five independent SAG12-PPDKgDNA lines, although variation was high and the differences between individual lines and the wild-type were not significant. This increase suggests that at this time-point amino acid production occurs at a greater rate than amino acid export can occur, and so amino acids accumulate during the leaf. Total free amino acids were not significantly different in ΔPPDK plants compared to wild-type.

Transport amino acids (glutamine and asparagine) were also measured and expressed as a percentage of total free amino acids. In SAG12-PPDKgDNA plants, transport amino acid content was significantly higher than in wild-type plants at weeks seven and eight. The increase occurred in all five independent SAG12-PPDKgDNA lines, although variation was high and the differences between individual lines and the wild-type were not significant. Therefore, in addition to an increase in total free amino acid content in SAG12-PPDKgDNA plants, the content of transport amino acids increases as a proportion of the total. Again, this suggests that glutamine and asparagine production exceed the export capacity of the leaf at these timepoints, supporting the hypothesis that increased PPDK abundance during senescence increases the efficiency of amino acid inter-conversions leading to the formation of transport amino acids. In ΔPPDK plants, no significant difference to the wild-type was observed.

Example 7

Phenotypic Analysis of Transformed Tobacco Plants

Analysis of Tobacco Leaf Nitrogen Content

Leaf nitrogen content was measured in ripe leaves of negative segregant and SAG12-PPDK K326 tobacco. Ripe leaves are those ready for harvesting for tobacco production. Leaf nitrogen content of SAG12-PPDK plants was lower than that of negative segregant plants, for some of the four independent SAG12-PPDK lines.

Ripe leaves were used to measure leaf nitrogen content since these leaves are at the stage at which they would be harvested for tobacco production. However, the fact that there was little difference in leaf nitrogen content in ripe leaves does not necessarily imply that nitrogen remobilisation was not increased. In time-courses of senescing SAG12-PPDKgDNA *Arabidopsis* plants, leaf nitrogen content was significantly lower than wild-type, but by late senescence the difference was much smaller. It is therefore possible that a difference in leaf nitrogen content in tobacco occurs earlier in senescence, and that the difference decreases by the time leaf nitrogen content was measured.

Analysis of Tobacco Leaf Amino Acid Content

Amino acid content was measured in mature leaves of K326 tobacco, induced to senesce by detachment and incubation in darkness at 30° C. for three days. This allowed comparisons to be made between the same leaves before and after induction of senescence. Induction of senescence by leaf detachment and dark incubation shows greatest overlap of gene expression patterns with age-related senescence.

In K326 tobacco, total amino acid content increased following induction of senescence in negative segregant plants and in SAG12-PPDK plants. The increase was calculated as a percentage of total amino acid content before induction of senescence. For SAG12-PPDK line C10, the increase was significantly smaller than that in negative segregant plants, but no other SAG12-PPDK line showed a significant difference to negative segregant plants. Overexpression of PPDK during senescence therefore appeared to have little effect on total amino acid content following induction of dark-induced senescence. Transport amino acid (glutamine and asparagine) content also increased in K326 tobacco following induction of senescence, but the increase occurred in both negative segregant and SAG12-PPDK lines, and there was no significant difference between genotypes in the degree of increase following induction of senescence.

Analysis of Tobacco Seed

Individual seed mass was measured in K326 tobacco, and was significantly higher in SAG12-PPDKgDNA and SAG12-PPDKcDNA plants compared to negative segregant plants, for all four independent transgenic lines. Mass of seed per seed pod was also measured, and was significantly higher in SAG12-PPDKgDNA and SAG12-PPDKcDNA plants.

Referring to FIG. 14, there is shown that the seed size is increased in SAG12-PPDK K326 tobacco. Individual seed mass in K326 zero copy (plants which are negative segregants for the SAG12-PPDK insert) and SAG12-PPDK plants, was calculated by photographing, counting and weighing approximately 1000 seed. Data are shown as mean of 10 biological replicates for zero copy plants, and four biological replicates for each SAG12-PPDK line. Error bars are one SEM. SAG12-PPDK lines are arranged in order of increasing PPDK abundance in ripe leaves. Seed mass is higher in SAG12-PPDK plants. The difference between genotypes were tested using ANOVA (F=4.870, df=4, p=0.006). Lines significantly different to zero copy plants were G8 (p=0.005) and C10 (p=0.002).

The percentage nitrogen content of seed was higher for all four independent SAG12-PPDKgDNA and SAG12-PPDKcDNA lines, but the difference was not significant. However, mass of nitrogen per seed was significantly higher in SAG12-PPDKgDNA and SAG12-PPDKcDNA plants.

Referring to FIG. 15, it is clearly shown that seed nitrogen content is increased in SAG12-PPDK K326 tobacco. The mass of nitrogen in individual seed of K326 zero copy and SAG12-PPDK plants, was calculated from seed mass and seed nitrogen content data. Data are shown as mean of 10 biological replicates for zero copy plants, and four biological replicates for each SAG12-PPDK line. Error bars are one SEM. SAG12-PPDK lines are arranged in order of increasing PPDK abundance in ripe leaves. Mass of nitrogen in individual seed is higher in SAG12-PPDK plants. The differences between genotypes were tested using ANOVA (F=7.807, df=4, p=0.001). Lines significantly different to zero copy plants were G8 (p=0.000) and C10 (p=0.000).

This suggests that nitrogen supply to seeds was increased in SAG12-PPDKgDNA and SAG12-PPDKcDNA K326 tobacco plants. In K326 plants, a dose response to PPDK was observed. Plants with higher PPDK abundance in ripe leaves had larger seed individual seed mass, higher mass of seed per seed pod, and increased mass of nitrogen in individual seed. This strongly supports a role for PPDK in nitrogen remobilisation, since increased PPDK content appears to be connected with increased nitrogen supply to seed.

In summary, in SAG12-PPDK K326 tobacco individual seed mass (FIG. 14) and nitrogen mass per seed (FIG. 15) were both increased, suggesting that nitrogen remobilisation was increased by overexpression of PPDK. An increase in transport amino acid content of senescing leaves would therefore be expected, as for *Arabidopsis* SAG12-PPDKgDNA plants. However, in *Arabidopsis* amino acid content was measured in naturally senescent leaves, whereas in tobacco, senescence was induced by leaf detachment and incubation in darkness. Since the processes that occur in dark-induced and age-related senescence differ, the processes occurring in the tobacco leaves were unlikely to be analagous to those in the *Arabidopsis* leaves.

Example 8

Generation of *Arabidopsis* Plants Over-Expressing PCK and PPDK

Over-expression of *Arabidopsis* PCK (At4g37870.1) during senescence was achieved by fusing the coding region and genomic clone of PCK to the senescence-associated gene 12 (SAG12) promoter within the BNP1380000001 binary vector, which was transformed into *Arabidopsis thaliana*, as described in Examples 1 and 2.

The At PCK coding sequence was first isolated from *Arabidopsis* cDNA, and the genomic sequence was isolated from *Arabidopsis* genomic DNA using PCR, as described in Example 1 in relation to PPDK. However, PCR primers were designed including the start and stop codons of the *Arabidopsis thaliana* (At) PCK gene, and also included an XbaI restriction site in the forward primer, AtPCK-Xba IFOR (SEQ ID No.25), and a SacI restriction site in the reverse primer, AtPCK-Sac IREV (SEQ ID No.26), as shown in Table 1, in order to facilitate the subsequent ligation of the gene into the BNP1380000001 vector, which is illustrated in FIG. 3a.

The cDNA and genomic DNA templates used for each PCR reaction were prepared according to Example 1. The PCR reaction mixture contained 1×HF buffer (NEB), 2 mM magnesium chloride (NEB), 0.5 mM dNTPs (Bioline), 100 ng of template (cDNA or genomic DNA), 0.5 µM each primer and 1 unit Phusion High-Fidelity DNA Polymerase (NEB). Thermal cycling was performed using a Techne Thermal Cycler with an initial denaturation step of 98° C. for 30 s, followed by 35 cycles of 98° C. for 10 s, 60° C. for 30 s and an extension time of 72° C. for 2 min 30 s for the coding region and 4 min 30 s for the genomic clone. The last step involved a final extension at 72° C. for 10 min.

These PCR products resulted in a 2 kb band for the coding sequence (cDNA) and a 3.5 kb band for the genomic sequence of PCK, and were PEG-precipitated. The amplified DNA was ligated (blunt-end) into the pCR4 Blunt-TOPO vector (Invitrogen) according to the recommended protocol, as for PPDK described in Example 1. The plasmid was then transformed into Library Efficiency DH5α *E. coli* cells. Kanamycin (50 µg ml$^{-1}$) was used as the selective antibiotic. Positive colonies were selected by colony PCR using the primers AtPCK-Xba IFOR (SEQ ID No.25) and AtPCK-Sac IREV (SEQ ID No.26) for both the coding region and the genomic clone. Positive colonies were grown overnight in a shaking incubator at 37° C. in 5 ml of LB broth containing 50 µg ml$^{-1}$ kanamycin.

Plasmid DNA was isolated using the QIAprep Spin Miniprep kit (Qiagen Ltd) and insert sizes were analysed by a sequential enzyme restriction digest. This was carried out by digesting 1 µg of DNA with 10 units of XbaI and 1× XbaI buffer at 37° C. for 2 h and then adding 10 units of SacI and 1× SacI Buffer at 37° C. overnight. Plasmid DNA containing the correct inserts was sequenced using AtPCK-Xba IFOR/AtPCK-Sac IREV. Sequence was analyzed using BioEdit and the amplified AtPCK coding sequence and genomic sequence were verified using BLASTX.

In order to ligate the AtPCK coding region and genomic clone into the pBNP vector shown in FIG. 3a, *E. coli* colonies representing each of the two plasmids were used to inoculate 25 ml of LB broth containing 50 µml$^{-1}$ kanamycin. The cultures were left shaking overnight at 37° C. and the plasmid DNA was purified using the QIAfilter plasmid midi kit (Qiagen Ltd). The pBNP vector was purified in an identical fashion but from 100 ml of culture containing 50 µg ml$^{-1}$ kanamycin. The same sequential enzyme digest as described above was performed on all purified plasmid DNA. 3 µg of DNA was digested for the plasmids containing the coding region and genomic clone and 1 µg of DNA for the pBNP vector. Samples were separated by crystal violet gel electrophoresis and the products were purified using the Qiaquick Gel Extraction kit (Qiagen Ltd). The 14.4 kb pBNP vector product was treated with alkaline phosphatase to prevent self-ligation and the coding region and genomic clone inserts were ligated into the pBNP vector using XbaI/SacI digests. Library efficiency DH5α *E. coli* cells were transformed with 2 µl of the ligation reaction and positive colonies were screened by PCR using AtPCK-Xba IFOR and AtPCK-Sac IREV.

Plasmid DNA was extracted from the colonies containing the desired insert using the QIAprep Spin Miniprep kit (Qiagen Ltd) and DNA was subsequently digested with 10 units of XbaI, 15 units of SacI and 1× XbaI Buffer at 37° C. for 2 h. Two separate colonies each of the coding sequence and the genomic sequence insert in the pBNP vector, which showed the correct expected restriction enzyme digest pattern, were selected and sequenced using the BNP-SAG12FWD primer (SEQ ID No.9). The sequence was analyzed using the BioEdit program. The constructs generated were named pALBNP1 (coding sequence) and pALBNP2 (genomic sequence), as shown in FIG. 3b.

Five homozygous single insert lines were generated and over-expression of PCK was verified through immunoblotting as described in Example 3, using a PCK specific antibody. A polyclonal antiserum was raised in rabbit using synthetic peptides designed against the PCK amino acid sequence. The sequences were (i) DEHCWTETGVSNIEG (SEQ ID No.27), and (ii) CVDLSREKEPDIWNA (SEQ ID No.28), which were chemically synthesised and then coupled to keyhole limpet haemocyanin before being co-injected into rabbits. The results obtained using the antibody are illustrated in FIG. 16, which shows that transformed plants had elevated levels of PCK protein.

SAG12-PCK-PPDK cell lines were generated by crossing single SAG12-PCK transformants (3)1 and (19)4 with a strong SAG12-PPDK over-expressing line. Analysis of the plants having elevated levels of both PCK and PPDK showed increased rosette mass, as shown in FIG. 17.

Finally, although the inventors do not wish to be bound by hypothesis, FIG. 18 shows a speculative biochemical pathway illustrating how PCK and PPDK may affect Nitrogen remobilisation.

PCK/PPDK Double Constructs

The inventors observed that, when transformed into a plant, the PCK and PPDK single constructs shown in FIG. 3 resulted in increased rates of nitrogen remobilisation from senescent leaves, and also an increase in the amount of vegetative plant growth (which corresponds to an increase in crop yield), when these enzymes were over-expressed in senescent leaves. The inventors therefore decided to produce two double constructs in which the genes encoding PCK and PPDK were both inserted into pBNP130000001 under the control of the SAG12 promoter.

The first double construct was made by ligating the gDNA encoding PCK downstream (i.e. the 3' end) of the PPDK-encoding gDNA fragment of BNP-PPDKgDNA using an XbaI/SacI digestion. Thus, the SAG12 promoter in the plasmid was responsible for expression of both the PPDK gene and the PCK gene.

The second double construct was made by ligating the gDNA encoding PPDK immediately downstream of the PCK-encoding gDNA fragment of pALBNP2 using an AvrII/BamHI digest. Again, the SAG12 was responsible for expression of both the PPDK gene and the PCK gene.

The invention claimed is:

1. A genetic construct comprising a promoter operably linked to at least one coding sequence, which encodes at least one polypeptide having cytosolic pyruvate orthophosphate dikinase (PPDK) activity,
wherein the promoter is a senescence-specific promoter, and wherein the coding sequence, which encodes the polypeptide having cytosolic PPDK activity, comprises a nucleic acid sequence as set out in SEQ ID No. 20, SEQ ID No. 21, or a functional variant or fragment thereof, the variant or fragment encoding the polypeptide having cytosolic PPDK activity and having at least 95% sequence with SEQ ID No. 20 or SEQ ID No. 21, or wherein the polypeptide having cytosolic PPDK activity comprises an amino acid sequence as set out in SEQ ID No. 23, or a functional variant or fragment thereof, the variant or fragment comprising the polypeptide having cytosolic PPDK activity and having at least 95% sequence identity with SEQ ID No. 23.

2. The genetic construct according to claim 1, wherein the construct encodes cytosolic PPDK or a functional variant or fragment thereof, and not phosphoenolpyruvate carboxykinase PCK, wherein the variant or fragment comprises the polypeptide having cytosolic PPDK activity and having at least 95% sequence identity with SEQ ID No. 23.

3. A recombinant vector comprising the genetic construct according to claim 1.

4. A method of decreasing the concentration of nitrogen in leaves of a test plant to below that of the corresponding concentration of nitrogen in a wild-type plant cultured under the same conditions, the method comprising altering plant metabolism in the test plant to achieve increased levels of cytosolic PPDK in plant leaves after initiation of leaf senescence, wherein the method comprises transforming the test plant with a genetic construct comprising a senescence-specific promoter operably linked to at least one coding sequence which encodes at least one polypeptide having cytosolic pyruvate orthophosphate dikinase (PPDK) activity.

5. A method of increasing the growth rate of a test plant compared to the corresponding growth rate of a wild-type plant cultured under the same conditions, the method comprising altering plant metabolism in the test plant to achieve increased levels of cytosolic PPDK in plant leaves after initiation of leaf senescence, wherein the method comprises transforming the test plant with a genetic construct comprising a senescence-specific promoter operably linked to at least one coding sequence, which encodes at least one polypeptide having cytosolic pyruvate orthophosphate dikinase (PPDK) activity.

6. A cell comprising the genetic construct according to claim 1.

7. A transgenic plant comprising the genetic construct according to claim 1.

8. The transgenic plant according to claim 7, wherein the plant is from the Brassicaceae, Poales or Solanaceae family.

9. A plant propagation product obtained from the transgenic plant according to claim 7 and comprising the genetic construct that comprises a senescence-specific promoter operably linked to at least one coding sequence, which encodes at least one polypeptide having cytosolic pyruvate orthophosphate dikinase (PPDK) activity.

10. The plant propagation product according to claim 9, wherein the plant propagation product is a seed.

11. A method of producing a transgenic plant which remobilizes nitrogen at a higher rate than a corresponding wild-type plant cultured under the same conditions, the method comprising: transforming a plant cell with a genetic construct that comprises a senescence-specific promoter operably linked to at least one coding sequence, which encodes at least one polypeptide having cytosolic pyruvate orthophosphate dikinase (PPDK) activity; and regenerating a plant from the transformed cell.

12. A method of producing a transgenic plant having a higher growth rate than a corresponding wild-type plant cultured under the same conditions, the method comprising:
    transforming a plant cell with a genetic construct that comprises a senescence-specific promoter operably linked to at least one coding sequence, which encodes at least one polypeptide having cytosolic pyruvate orthophosphate dikinase (PPDK) activity; and regenerating a plant from the transformed cell.

13. A harvested leaf containing a lower level of nitrogen than the corresponding level of nitrogen in a harvested leaf taken from a wild-type plant cultured under the same conditions, wherein the leaf is harvested from the transgenic plant according to claim 7.

\* \* \* \* \*